United States Patent
Arora et al.

(10) Patent No.: US 9,376,469 B2
(45) Date of Patent: Jun. 28, 2016

(54) PROTEOLYTICALLY RESISTANT HYDROGEN BOND SURROGATE HELICES

(71) Applicant: New York University, New York, NY (US)

(72) Inventors: Paramjit S. Arora, Huntington, NY (US); Anupam Patgiri, New York, NY (US); Stephen Joy, New York, NY (US)

(73) Assignee: New York University, New York, NY (US)

( * ) Notice: Subject to any disclaimer, the term of this patent is extended or adjusted under 35 U.S.C. 154(b) by 29 days.

(21) Appl. No.: 13/724,887

(22) Filed: Dec. 21, 2012

(65) Prior Publication Data

US 2013/0210144 A1 Aug. 15, 2013

Related U.S. Application Data

(60) Provisional application No. 61/578,646, filed on Dec. 21, 2011, provisional application No. 61/578,652, filed on Dec. 21, 2011.

(51) Int. Cl.
| | |
|---|---|
| *C07K 7/56* | (2006.01) |
| *C07K 2/00* | (2006.01) |
| *C07K 4/00* | (2006.01) |
| *C07K 7/50* | (2006.01) |
| *C07K 7/54* | (2006.01) |
| *A61K 38/02* | (2006.01) |
| *A61K 38/31* | (2006.01) |

(52) U.S. Cl.
CPC . *C07K 7/56* (2013.01); *A61K 38/02* (2013.01); *C07K 2/00* (2013.01); *C07K 4/00* (2013.01); *C07K 7/50* (2013.01); *C07K 7/54* (2013.01); *A61K 38/31* (2013.01)

(58) Field of Classification Search
None
See application file for complete search history.

(56) References Cited

U.S. PATENT DOCUMENTS

| | | | |
|---|---|---|---|
| 7,202,332 | B2 | 4/2007 | Arora et al. |
| 7,705,118 | B2 | 4/2010 | Arora et al. |
| 8,071,541 | B2 | 12/2011 | Arora et al. |
| 2006/0014675 | A1 | 1/2006 | Arora et al. |
| 2007/0197772 | A1 | 8/2007 | Arora et al. |
| 2010/0228004 | A1 | 9/2010 | Prabhakaran |
| 2010/0234563 | A1 | 9/2010 | Arora et al. |
| 2011/0059161 | A1 | 3/2011 | Templeton |
| 2013/0005943 | A1 | 1/2013 | Arora et al. |
| 2013/0123196 | A1 | 5/2013 | Arora et al. |
| 2014/0051828 | A1 | 2/2014 | Arora et al. |

FOREIGN PATENT DOCUMENTS

| | | |
|---|---|---|
| WO | 2005/118620 A2 | 12/2005 |
| WO | 2008/121767 A2 | 10/2008 |
| WO | 2010/033879 A2 | 3/2010 |
| WO | 2010/034031 A1 | 3/2010 |
| WO | 2012/122059 A1 | 9/2012 |
| WO | 2013/033645 A1 | 3/2013 |

OTHER PUBLICATIONS

Patgiri et al., Nature Protocols (2010) 5 (11), 1857-1865.*
Chapman et al., "A Highly Stable Short Alpha-Helix Constrained by a Main-Chain Hydrogen-Bond Surrogate," J. Am. Chem. Soc. 126:12252-53 (2004).
Chapman et al., "Trapping a Folding Intermediate of the Alpha-Helix: Stabilization of the Pi-Helix," Biochemistry 47:4189-95 (2008).
Chène, "Inhibiting the p53-MDM2 Interaction: An Important Target for Cancer Therapy," Nat. Rev. Cancer 3:102-09 (2003).
Frackenpohl et al., "The Outstanding Biological Stability of Beta- and Gamma-Peptides Toward Proteolytic Enzymes: An In Vitro Investigation With Fifteen Peptidases," ChemBioChem 2:445-55 (2001).
Henchey et al., "High Specificity in Protein Recognition by Hydrogen-Bond-Surrogate Alpha-Helices: Selective Inhibition of the p53/MDM2 Complex," ChemBioChem 11:2104-07 (2010).
Henchey et al., "Inhibition of Hypoxia Inducible Factor 1—Transcription Coactivator Interaction by a Hydrogen Bond Surrogate Alpha-Helix," J. Am. Chem. Soc. 132:941-43 (2010).
Horne & Gellman, "Foldamers With Heterogeneous Backbones," Acc. Chem. Res. 41(10):1399-408 (2008).
Horne et al., "Interplay Among Side Chain Sequence, Backbone Composition, and Residue Rigidification in Polypeptide Folding and Assembly," Proc. Nat'l Acad. Sci. 105(27):9151-56 (2008).
Horne et al., "Structural and Biological Mimicry of Protein Surface Recognition by Alpha/Beta-Peptide Foldamers," Proc. Nat'l Acad. Sci. 106(35):14751-56 (2009).
Kussie et al., "Structure of the MDM2 Oncoprotein Bound to the p53 Tumor Suppressor Transactivation Domain," Science 274:948-53 (1996).
Liu et al., "Atomic Structure of a Short Alpha-Helix Stabilized by a Main Chain Hydrogen-Bond Surrogate," J. Am. Chem. Soc. 130:4334-37 (2008).
Patgiri et al., "A Hydrogen Bond Surrogate Approach for Stabilization of Short Peptide Sequences in Alpha-Helical Conformation," Acc. Chem. Res. 41(10):1289-300 (2008).
Patgiri et al., "An Orthosteric Inhibitor of the Ras-Sos Interaction," Nat. Chem. Biol. 7:585-87 (2011).
Seebach & Gardiner, "Beta-Peptidic Peptidomimetics," Acc. Chem. Res. 41(10):1366-75 (2008).
Vaz et al., "Comparison of Design Strategies for Promotion of Beta-Peptide 14-Helix Stability in Water," ChemBioChem 9:2254-59 (2008).
Wang et al., "Enhanced Metabolic Stability and Protein-Binding Properties of Artificial Alpha Helices Derived from a Hydrogen-Bond Surrogate: Application to Bcl-xL," Angew. Chem. Int. Ed. 44:6525-29 (2005).

(Continued)

*Primary Examiner* — Marcela M Cordero Garcia
*Assistant Examiner* — Catherine Mader
(74) *Attorney, Agent, or Firm* — LeClairRyan, a Professional Corporation

(57) ABSTRACT

The present invention relates to peptidomimetics having a stable, internally constrained protein secondary structure, where the peptidomimetics contain a hydrogen bond surrogate in the internal constraint, and at least one beta amino acid. Methods for promoting cell death using peptidomimetics that inhibit p53/hDM2 are also disclosed.

27 Claims, 24 Drawing Sheets

(56) References Cited

OTHER PUBLICATIONS

Wang et al., "Evaluation of Biologically Relevant Short Alpha-Helices Stabilized by a Main-Chain Hydrogen-Bond Surrogate," J. Am. Chem. Soc. 128:9248-56 (2006).

Wang et al., "Inhibition of HIV-1 Fusion by Hydrogen-Bond-Surrogate-Based Alpha Helices," Angew. Chem. Int. Ed. 47:1879-82 (2008).

International Preliminary Report on Patentability for corresponding PCT/US2012/071223 (Jul. 3, 2014).

International Search Report and Written Opinion for corresponding PCT/US2012/071223 (May 3, 2013).

Bergman et al., "Synthesis of Stapled β3-Peptides Through Ring-Closing Metathesis," Org. Lett. 11(19):4438-40 (2009).

Chapman & Arora, "Optimized Synthesis of Hydrogen-Bond Surrogate Helices: Surprising Effects of Microwave Heating on the Activity of Grubbs Catalysts," Org. Lett. 8(25):5825-28 (2006).

Dimartino et al., "Solid-Phase Synthesis of Hydrogen-Bond Surrogate-Derived α-Helices," Org. Lett. 7(12):2389-92 (2005).

Extended European Search Report (Jun. 2, 2015) for corresponding European Patent Application No. 12859663.2.

Gentilucci et al., "Chemical Modifications Designed to Improve Peptide Stability: Incorporation of Non-Natural Amino Acids, Pseudo-Peptide Bonds, and Cyclization," Curr. Pharm. Design 16(28):3185-203 (2010).

Guarracino & Arora, "Making Strides in Peptide-Based Therapeutics," Chem. Biol. 16:919-20 (2009).

Mahon & Arora, "Design, Synthesis and Protein-Targeting Properties of Thioether-Linked Hydrogen Bond Surrogate Helices," Chem. Commun. 48:1416-18 (2012).

Patgiri et al., "Nucleation Effects in Peptide Foldamers," J. Am. Chem. Soc. 134:11495-502 (2012).

Patgiri et al., "Solid Phase Synthesis of Hydrogen Bond Surrogate Derived α-Helices: Resolving the Case of a Difficult Amide Coupling," Org. Biomol. Chem. 8:1773-76 (2010).

Wang et al., "Nucleation and Stability of Hydrogen-Bond Surrogate-Based α-Helices," Org. Biomol. Chem. 4(22):4074-81 (2006).

* cited by examiner

SEQUENCE LISTING

<160> NUMBER OF SEQ ID NOS: 16

<210> SEQ ID NO 1
<211> LENGTH: 29
<212> TYPE: PRT
<213> ORGANISM: Artificial
<220> FEATURE:
<223> OTHER INFORMATION: Signal peptide for the endoplasmic reticulum

<400> SEQUENCE: 1

Met Met Ser Phe Val Ser Leu Leu Leu Val Gly Ile Leu Phe Tyr Ala
1               5                   10                  15

Thr Glu Ala Glu Gln Leu Thr Lys Cys Glu Val Phe Gln
            20                  25

<210> SEQ ID NO 2
<211> LENGTH: 4
<212> TYPE: PRT
<213> ORGANISM: Artificial
<220> FEATURE:
<223> OTHER INFORMATION: Endoplasmic reticulum retention signal

<400> SEQUENCE: 2

Lys Glu Asp Leu
1

<210> SEQ ID NO 3
<211> LENGTH: 8
<212> TYPE: PRT
<213> ORGANISM: Artificial
<220> FEATURE:
<223> OTHER INFORMATION: Nuclear transport peptide

<400> SEQUENCE: 3

Pro Pro Lys Lys Lys Arg Lys Val
1               5

<210> SEQ ID NO 4
<211> LENGTH: 25
<212> TYPE: PRT
<213> ORGANISM: Artificial
<220> FEATURE:
<223> OTHER INFORMATION: Transport peptide for mitochondria

<400> SEQUENCE: 4

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 5
<211> LENGTH: 13
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (3)..(3)
<223> OTHER INFORMATION: Xaa at position 3 is beta glutamic acid
<220> FEATURE:
<221> NAME/KEY: MISC_FEATURE
<222> LOCATION: (4)..(4)
<223> OTHER INFORMATION: Xaa at position 4 is N-allylglycine

```
<220> FEATURE:
<221> NAME/KEY: MISC_FEATURE
<222> LOCATION: (7)..(7)
<223> OTHER INFORMATION: Xaa at position 7 is beta aspartic acid
<220> FEATURE:
<221> NAME/KEY: MISC_FEATURE
<222> LOCATION: (11)..(11)
<223> OTHER INFORMATION: Xaa at position 11 is beta leucine

<400> SEQUENCE: 5

Xaa Gln Xaa Xaa Phe Ser Xaa Leu Trp Lys Xaa Leu Ser
1               5                   10

<210> SEQ ID NO 6
<211> LENGTH: 13
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allylglycine

<400> SEQUENCE: 6

Xaa Gln Glu Xaa Phe Ser Asp Leu Trp Lys Leu Leu Ser
1               5                   10

<210> SEQ ID NO 7
<211> LENGTH: 12
<212> TYPE: PRT
<213> ORGANISM: Artificial
<220> FEATURE:
<223> OTHER INFORMATION: Oligopeptide derived from p53
<220> FEATURE:
<221> NAME/KEY: MISC_FEATURE
<222> LOCATION: (1)..(1)
<223> OTHER INFORMATION: Position 1 is acetylated
<220> FEATURE:
<221> NAME/KEY: MISC_FEATURE
<222> LOCATION: (2)..(2)
<223> OTHER INFORMATION: Xaa at position 2 is beta glutamic acid
<220> FEATURE:
<221> NAME/KEY: MISC_FEATURE
<222> LOCATION: (6)..(6)
<223> OTHER INFORMATION: Xaa at position 6 is beta aspartic acid
<220> FEATURE:
<221> NAME/KEY: MISC_FEATURE
<222> LOCATION: (10)..(10)
<223> OTHER INFORMATION: Xaa at position 10 is beta leucine

<400> SEQUENCE: 7

Gln Xaa Gly Phe Ser Xaa Leu Trp Lys Xaa Leu Ser
1               5                   10

<210> SEQ ID NO 8
<211> LENGTH: 12
<212> TYPE: PRT
<213> ORGANISM: Artificial
<220> FEATURE:
<223> OTHER INFORMATION: Oligopeptide derived from p53
<220> FEATURE:
<221> NAME/KEY: MISC_FEATURE
<222> LOCATION: (1)..(1)
<223> OTHER INFORMATION: Position 1 is acetylated
<220> FEATURE:
<221> NAME/KEY: MISC_FEATURE
<222> LOCATION: (2)..(2)
<223> OTHER INFORMATION: Xaa at position 2 is cyclic beta residue
```

-continued

```
      (1S,2S)-2-aminocyclopentane carboxylic acid
<220> FEATURE:
<221> NAME/KEY: MISC_FEATURE
<222> LOCATION: (6)..(6)
<223> OTHER INFORMATION: Xaa at position 6 is cyclic beta residue
      (1S,2S)-2-aminocyclopentane carboxylic acid
<220> FEATURE:
<221> NAME/KEY: MISC_FEATURE
<222> LOCATION: (10)..(10)
<223> OTHER INFORMATION: Xaa at position 10 is cyclic beta residue
      (1S,2S)-2-aminocyclopentane carboxylic acid

<400> SEQUENCE: 8

Gln Xaa Gly Phe Ser Xaa Leu Trp Lys Xaa Leu Ser
1               5                   10

<210> SEQ ID NO 9
<211> LENGTH: 13
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (3)..(3)
<223> OTHER INFORMATION: Xaa at position 3 is beta glutamic acid
<220> FEATURE:
<221> NAME/KEY: MISC_FEATURE
<222> LOCATION: (4)..(4)
<223> OTHER INFORMATION: Xaa at position 4 is N-allylglycine
<220> FEATURE:
<221> NAME/KEY: MISC_FEATURE
<222> LOCATION: (7)..(7)
<223> OTHER INFORMATION: Xaa at position 7 is beta aspartic acid
<220> FEATURE:
<221> NAME/KEY: MISC_FEATURE
<222> LOCATION: (11)..(11)
<223> OTHER INFORMATION: Xaa at position 11 is beta leucine

<400> SEQUENCE: 9

Xaa Gln Xaa Xaa Ala Ser Xaa Leu Trp Lys Xaa Ala Ser
1               5                   10

<210> SEQ ID NO 10
<211> LENGTH: 12
<212> TYPE: PRT
<213> ORGANISM: Artificial
<220> FEATURE:
<223> OTHER INFORMATION: Oligopeptide derived from p53
<220> FEATURE:
<221> NAME/KEY: MISC_FEATURE
<222> LOCATION: (1)..(1)
<223> OTHER INFORMATION: Position 1 is acetylated

<400> SEQUENCE: 10

Gln Glu Gly Phe Ser Asp Leu Trp Lys Leu Leu Ser
1               5                   10

<210> SEQ ID NO 11
<211> LENGTH: 14
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
```

```
<221> NAME/KEY: MISC_FEATURE
<222> LOCATION: (3)..(3)
<223> OTHER INFORMATION: Xaa at position 3 is beta glutamic acid
<220> FEATURE:
<221> NAME/KEY: MISC_FEATURE
<222> LOCATION: (4)..(4)
<223> OTHER INFORMATION: Xaa at position 4 is N-allylglycine
<220> FEATURE:
<221> NAME/KEY: MISC_FEATURE
<222> LOCATION: (7)..(7)
<223> OTHER INFORMATION: Xaa at position 7 is beta aspartic acid
<220> FEATURE:
<221> NAME/KEY: MISC_FEATURE
<222> LOCATION: (11)..(11)
<223> OTHER INFORMATION: Xaa at position 11 is beta leucine
<220> FEATURE:
<221> NAME/KEY: MISC_FEATURE
<222> LOCATION: (14)..(14)
<223> OTHER INFORMATION: Position 14 is labeled with
      5-acetamidofluorescein

<400> SEQUENCE: 11

Xaa Gln Xaa Xaa Phe Ser Xaa Leu Trp Lys Xaa Leu Ser Cys
1               5                   10

<210> SEQ ID NO 12
<211> LENGTH: 13
<212> TYPE: PRT
<213> ORGANISM: Artificial
<220> FEATURE:
<223> OTHER INFORMATION: Oligopeptide derived from p53
<220> FEATURE:
<221> NAME/KEY: MISC_FEATURE
<222> LOCATION: (1)..(1)
<223> OTHER INFORMATION: Position 1 is acetylated
<220> FEATURE:
<221> NAME/KEY: MISC_FEATURE
<222> LOCATION: (2)..(2)
<223> OTHER INFORMATION: Xaa at position 2 is beta glutamic acid
<220> FEATURE:
<221> NAME/KEY: MISC_FEATURE
<222> LOCATION: (6)..(6)
<223> OTHER INFORMATION: Xaa at position 6 is beta aspartic acid
<220> FEATURE:
<221> NAME/KEY: MISC_FEATURE
<222> LOCATION: (10)..(10)
<223> OTHER INFORMATION: Xaa at position 10 is beta leucine
<220> FEATURE:
<221> NAME/KEY: MISC_FEATURE
<222> LOCATION: (13)..(13)
<223> OTHER INFORMATION: Position 13 is labeled with
      5-acetamidofluorescein

<400> SEQUENCE: 12

Gln Xaa Gly Phe Ser Xaa Leu Trp Lys Xaa Leu Ser Cys
1               5                   10

<210> SEQ ID NO 13
<211> LENGTH: 16
<212> TYPE: PRT
<213> ORGANISM: Artificial
<220> FEATURE:
<223> OTHER INFORMATION: Oligopeptide derived from p53
<220> FEATURE:
<221> NAME/KEY: MISC_FEATURE
<222> LOCATION: (1)..(1)
<223> OTHER INFORMATION: Position 1 is acetylated
<220> FEATURE:
<221> NAME/KEY: MISC_FEATURE
<222> LOCATION: (16)..(16)
<223> OTHER INFORMATION: Position 16 is labeled with
      5-acetamidofluorescein

<400> SEQUENCE: 13
```

```
Glu Ala Phe Ser Asp Leu Trp Lys Leu Leu Pro Glu Asn Asn Val Cys
1               5                   10                  15

<210> SEQ ID NO 14
<211> LENGTH: 13
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allyl beta glycine
<220> FEATURE:
<221> NAME/KEY: MISC_FEATURE
<222> LOCATION: (8)..(8)
<223> OTHER INFORMATION: Xaa at position 8 is beta leucine
<220> FEATURE:
<221> NAME/KEY: MISC_FEATURE
<222> LOCATION: (12)..(12)
<223> OTHER INFORMATION: Xaa at position 12 is beta leucine

<400> SEQUENCE: 14

Xaa Gln Glu Xaa Phe Ser Asp Xaa Trp Lys Leu Xaa Ser
1               5                   10

<210> SEQ ID NO 15
<211> LENGTH: 12
<212> TYPE: PRT
<213> ORGANISM: Artificial
<220> FEATURE:
<223> OTHER INFORMATION: Oligopeptide derived from p53
<220> FEATURE:
<221> NAME/KEY: MISC_FEATURE
<222> LOCATION: (1)..(1)
<223> OTHER INFORMATION: Position 1 is acetylated
<220> FEATURE:
<221> NAME/KEY: MISC_FEATURE
<222> LOCATION: (3)..(3)
<223> OTHER INFORMATION: 'Xaa at position 3 is N-allyl beta glycine
<220> FEATURE:
<221> NAME/KEY: MISC_FEATURE
<222> LOCATION: (7)..(7)
<223> OTHER INFORMATION: 'Xaa at position 7 is beta leucine
<220> FEATURE:
<221> NAME/KEY: MISC_FEATURE
<222> LOCATION: (11)..(11)
<223> OTHER INFORMATION: Xaa at position 11 is beta leucine

<400> SEQUENCE: 15

Gln Glu Xaa Phe Ser Asp Xaa Trp Lys Leu Xaa Ser
1               5                   10

<210> SEQ ID NO 16
<211> LENGTH: 13
<212> TYPE: PRT
<213> ORGANISM: Artificial
<220> FEATURE:
<223> OTHER INFORMATION: Hydrogen bond surrogate helix
<220> FEATURE:
<221> NAME/KEY: MISC_FEATURE
<222> LOCATION: (1)..(1)
<223> OTHER INFORMATION: Xaa at position 1 is pentenoic acid
<220> FEATURE:
<221> NAME/KEY: MISC_FEATURE
<222> LOCATION: (4)..(4)
<223> OTHER INFORMATION: Xaa at position 4 is N-allyl beta glycine
<220> FEATURE:
<221> NAME/KEY: MISC_FEATURE
<222> LOCATION: (8)..(8)
```

```
<223> OTHER INFORMATION: Xaa at position 8 is beta leucine
<220> FEATURE:
<221> NAME/KEY: MISC_FEATURE
<222> LOCATION: (12)..(12)
<223> OTHER INFORMATION: Xaa at position 12 is beta alanine

<400> SEQUENCE: 16

Xaa Gln Glu Xaa Ala Ser Asp Xaa Trp Lys Leu Xaa Ser
1               5                   10
```

PROTEOLYTICALLY RESISTANT HYDROGEN BOND SURROGATE HELICES

This application claims the benefit of U.S. Provisional Patent Application Ser. Nos. 61/578,646, filed Dec. 21, 2011, and 61/578,652, filed Dec. 21, 2011, each of which is hereby incorporated by reference in its entirety.

This invention was made with government support under grant number GM073943 awarded by National Institutes of Health. The government has certain rights in this invention.

FIELD OF THE INVENTION

This invention is directed generally to peptidomimetics having a stable, internally constrained protein secondary structure, where the peptidomimetic contains a hydrogen bond surrogate in the internal constraint, and at least one beta amino acid.

BACKGROUND OF THE INVENTION

The in vivo efficacy of peptides is often compromised by their conformational and proteolytic instabilities in addition to their low cellular permeation. Modified peptides have been shown to overcome some or all of these limitations (Moellering et al., *Nature* 462:182 (2009); Horne et al., *Proc. Nat'l Acad. Sci. USA* 106:14751 (2009)). A synthetic method for stabilizing peptides in the desired helical conformation has been introduced (Patgiri et al., *Acc. Chem. Res.* 41:1289 (2008); Liu et al., *J. Am. Chem. Soc'y* 130:4334-37 (2008); Chapman et al., *Biochemistry* 47:4189-95 (2008)). In this strategy—termed the hydrogen bond surrogate (HBS) approach—a main chain hydrogen bond is replaced with a covalent bond to stabilize the helical conformation, as shown in FIG. 1. HBS α-helices have been shown to target their cognate protein receptors with high affinity and specificity (Patgiri et al., *Nat. Chem. Biol.* 7:585 (2011); Henchey et al., *J. Am. Chem. Soc'y* 132:941 (2010); Henchey et al., *ChemBioChem* 11:2104 (2010); Wang et al., *Angew. Chem. Int'l Ed.* 47:1879 (2008); Wang et al., *Angew. Chem. Int'l Ed.* 44:6525 (2005)). The stabilized α-helices can modulate chosen intracellular protein—protein interactions while their unconstrained counterparts remain ineffective (Patgiri et al., *Nat. Chem. Biol.* 7:585 (2011); Henchey et al., *J. Am. Chem. Soc'y* 132:941 (2010)).

The proteolytic stability of HBS α-helices composed of α-amino acids was investigated earlier, and it was found that there is a direct correlation between helicity and proteolytic stability, because proteases bind and cleave peptides in the extended conformation (Wang et al., *Angew. Chem. Int'l Ed.* 44:6525 (2005); Tyndall et al., *Chem. Rev.* 105:973 (2005)). However, the extent of proteolytic stability of HBS α-helices was found to be sequence dependent.

β-peptides and chimeric α/β-peptides have been known to resist degradation (Hook et al., *Chem. Biodivers.* 2:591 (2005); Seebach & Gardiner, *Acc. Chem. Res.* 41:1366 (2008); Horne & Gellman, *Acc. Chem. Res.* 41:1399 (2008); Sadowsky et al., *ChemBioChem* 8:903 (2007)). Oligomers composed of β³- and mixtures of α- and β³-residues are typically preorganized through side chain-to-side chain contacts (Arvidsson et al., *Chem. Commun.* 649 (2001); Kritzer et al., *J. Am. Chem. Soc'y* 127:167 (2005); Hart et al., *J. Am. Chem. Soc'y* 125:4022 (2003); Cheng & DeGrado, *J. Am. Chem. Soc'y* 123:5162 (2001)) or use of cyclic amino acid analogs with predefined φ, ψ-dihedral angles (Horne & Gellman, *Acc. Chem. Res.* 41:1399 (2008); (Appella et al., *Nature* 387:381 (1997); Vaz et al., *ChemBioChem* 9:2254 (2008)). It was unknown whether insertion of β³-residues within the macrocycle of HBS helices could lead to more stable HBS helices that also retain their functional properties, nor whether the stability of HBS helices containing attached peptides could be improved by replacing α-amino acid residues in the attached peptide with β³-residues without comprising the functional properties of the HBS helix.

The present invention is directed to overcoming these and other deficiencies in the art.

SUMMARY OF THE INVENTION

One aspect of the present invention relates to a peptidomimetic having a stable, internally constrained protein secondary structure, wherein the peptidomimetic is a compound of Formula I:

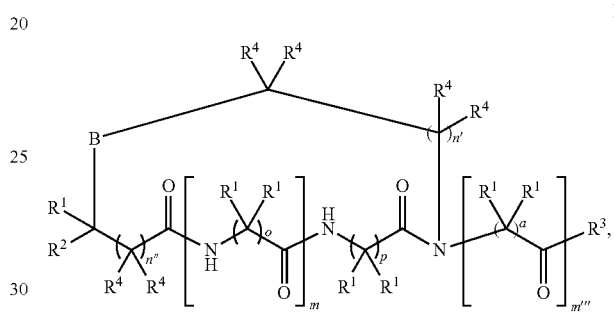

wherein:
B is $C(R^1)_2$, O, S, or $NR^1$;
each $R^1$ is independently hydrogen, an amino acid side chain, an alkyl, an alkenyl, an alkynyl, a cycloalkyl, a heterocyclyl, an aryl, a heteroaryl, or an arylalkyl;
$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

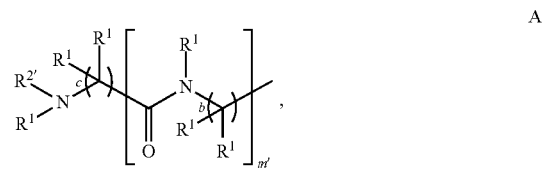

wherein:
$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m' is zero or any number;
each b is independently one or two; and
c is one or two;

$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

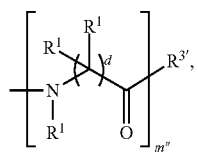

B wherein:
$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m" is zero or any number; and
each d is independently one or two;
each $R^4$ is independently hydrogen, an alkyl, an alkenyl, an alkynyl, a cycloalkyl, a heterocyclyl, an aryl, a heteroaryl, or an arylalkyl;
m, n', and n" are each independently zero, one, two, three, or four, wherein the sum of m, n', and n" is from two to six;
m'" is zero or one;
a is one or two;
each o is independently one or two;
p is one or two; and
wherein at least one of the following conditions is met
(i) m is one, two, three, or four and at least one o is two;
(ii) p is two;
(iii) m'" is one and a is two;
(iv) $R^2$ is a beta amino acid;
(v) $R^2$ is a moiety of Formula A wherein m' is at least one and at least one b is two;
(vi) $R^2$ is a moiety of Formula A wherein c is two;
(vii) $R^2$ is a moiety of Formula A wherein $R^{2'}$ is a beta amino acid;
(viii) $R^3$ is a beta amino acid;
(ix) $R^3$ is a moiety of Formula B wherein m" is at least one and at least one d is two; and
(x) $R^3$ is a moiety of Formula B wherein $R^{3'}$ is a beta amino acid.

Another aspect of the present invention relates to a peptidomimetic having a stable, internally constrained protein secondary structure, wherein the peptidomimetic is a compound of Formula IIA:

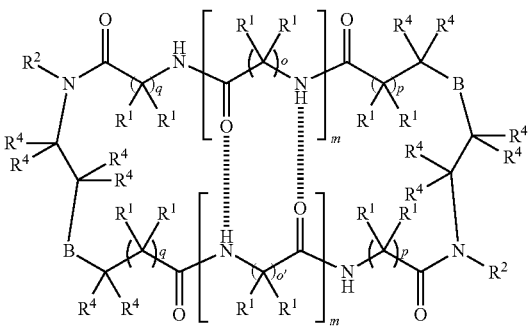

IIA wherein:
each B is independently $C(R^1)_2$, O, S, or $NR^1$;
each $R^1$ is independently hydrogen, an amino acid side chain, an alkyl, an alkenyl, an alkynyl, a cycloalkyl, a heterocyclyl, an aryl, a heteroaryl, or an arylalkyl;
each $R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

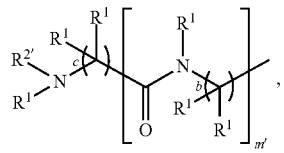

A wherein:
$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m' is zero or any number;
each b is independently one or two; and
c is one or two;
each $R^4$ is independently hydrogen, an alkyl, an alkenyl, an alkynyl, a cycloalkyl, a heterocyclyl, an aryl, a heteroaryl, or an arylalkyl;

m is one, two, three, or four;
each o and each o' are independently one or two, with the proviso that each corresponding o and o' are the same;
p is one or two;
q is one or two; and
wherein at least one of the following conditions is met
  (i) m is one, two, three, or four; at least one o is two; and at least one o' is two;
  (ii) p is two;
  (iii) q is two;
  (iv) at least one $R^2$ is a beta amino acid;
  (v) at least one $R^2$ is a moiety of Formula A wherein m' is at least one and at least one b is two;
  (vi) at least one $R^2$ is a moiety of Formula A wherein c is two; and
  (vii) at least one $R^2$ is a moiety of Formula A wherein $R^{2'}$ is a beta amino acid.

Another aspect of the present invention relates to a peptidomimetic having a stable, internally constrained protein secondary structure, wherein the peptidomimetic is a compound of Formula IIB:

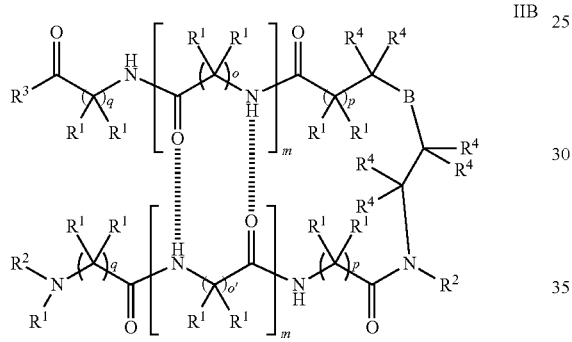

IIB wherein:
  each B is independently $C(R^1)_2$, O, S, or $NR^1$;
  each $R^1$ is independently hydrogen, an amino acid side chain, an alkyl, an alkenyl, an alkynyl, a cycloalkyl, a heterocyclyl, an aryl, a heteroaryl, or an arylalkyl;
  each $R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

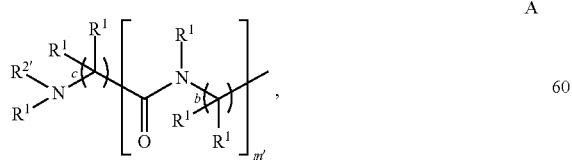

A wherein:
  $R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
  m' is zero or any number;
  each b is independently one or two; and
  c is one or two;
$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

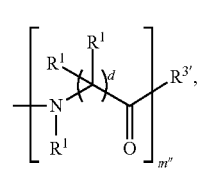

B wherein:
  $R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein alkenyl, an alkynyl, a cycloalkyl, a heterocyclyl, an aryl, a heteroaryl, an arylalkyl, an acyl, a peptide, a targeting moiety, or a tag;
  m'' is zero or any number; and
  each d is independently one or two;
each $R^4$ is independently hydrogen, an alkyl, an alkenyl, an alkynyl, a cycloalkyl, a heterocyclyl, an aryl, a heteroaryl, or an arylalkyl;
m is one, two, three, or four;
each o and each o' are independently one or two, with the proviso that each corresponding o and o' are the same;
p is one or two;
q is one or two; and
wherein at least one of the following conditions is met
  (i) m is one, two, three, or four; at least one o is two; and at least one o' is two;
  (ii) p is two;
  (iii) q is two;
  (iv) at least one $R^2$ is a beta amino acid;
  (v) at least one $R^2$ is a moiety of Formula A wherein m' is at least one and at least one b is two;
  (vi) at least one $R^2$ is a moiety of Formula A wherein c is two;

(vii) at least one $R^2$ is a moiety of Formula A wherein $R^{2'}$ is a beta amino acid;
(viii) $R^3$ is a beta amino acid;
(ix) $R^3$ is a moiety of Formula B wherein m" is at least one and at least one d is two; and
(x) $R^3$ is a moiety of Formula B wherein $R^{3'}$ is a beta amino acid.

Yet another aspect of the present invention relates to a method for promoting cell death. This method involves contacting a cell with one or more compounds of Formula I that inhibit p53/hDM2, under conditions effective for the one or more compounds to promote cell death.

Hydrogen bond surrogate helices have been previously shown to target intracellular protein—protein interactions with high affinity and specificity. Outlined herein is the design of HBS helices with enhanced resistance to proteolytic degradation. It has been found that judicious insertion of $\beta^3$-amino acid residues in constrained $\alpha$-peptide helices provides the desired proteolytic stability without impairing cell permeability properties of HBS sequences or their capacity to target protein receptors with high affinity. Significantly, this shows that the HBS approach can preorganize helical conformations in heterogeneous sequences. Judicious insertion of $\beta^3$-amino acid residues in the attached peptide of constrained $\alpha$-peptide helices has also been found to provide the desired proteolytic stability. It is expected that this can be done without impairing cell permeability properties of HBS sequences or their capacity to target protein receptors with high affinity.

BRIEF DESCRIPTION OF THE DRAWINGS

FIG. 2A shows overlays of energy minimized $\alpha 2/\beta$-peptide (left) and $\alpha 3/\beta$-peptide (right) structures and canonical $\alpha$-helices. Molecular modeling studies were performed with the Amber force-field within Macromodel (Mohamadi et al., *J. Comp. Chem.* 11:440 (1990), which is hereby incorporated by reference in its entirety). $\beta^3$-residues are shown in yellow. A comparison of the $\alpha$-HBS- and $\alpha 3/\beta$-HBS-constrained peptides is shown in FIG. 2B.

DETAILED DESCRIPTION OF THE INVENTION

Figure 1:
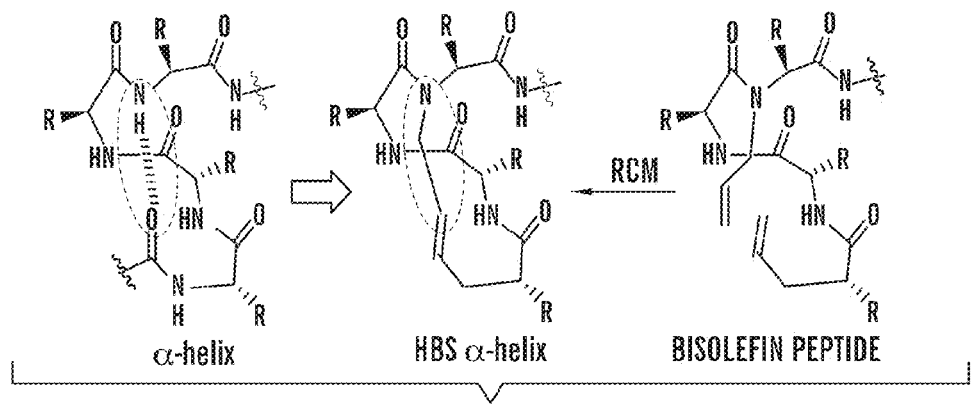
FIG. 1 is a schematic illustration of traditional HBS $\alpha$-helix design, showing the replacement of an N-terminal main-chain (i, i+4) H-bond with a carbon—carbon bond.

Protein secondary structures are defined by the hydrogen bonding patterns observed between the various main chain amide groups. Analyses of helix-coil transition in peptides emphasize the energetically demanding organization of three consecutive amino acids into the helical orientation as the slow step in helix formation (Qian & Schellman, *J. Chem. Phys.*, 96:3987-3994 (1992); Lifson & Roig, *J. Chem. Phys.*, 34:1963-1974 (1961); Zimm & Bragg, *J. Chem. Phys.*, 31:526-535 (1959), which are hereby incorporated by reference in their entirety). Preorganization of these amino acid residues is expected to overwhelm the intrinsic nucleation propensities and initiate helix formation (Austin et al., *J. Am. Chem. Soc.*, 119:6461-6472 (1997); Kemp et al., *J. Org. Chem.*, 56:6672-6682 (1991), which are hereby incorporated by reference in their entirety). In an α-helix, for example, a hydrogen bond between the C=O of the i$^{th}$ amino acid residue and the NH of the i+4$^{th}$ amino acid residue stabilizes and nucleates the helical structure. Similar interactions stabilize and nucleate other helices, β-sheet/β-hairpins, and other peptide secondary structures.

To mimic the C=O---H---N hydrogen bond, internally constrained peptidomimetics incorporating a covalent bond of the type C$_{1-5}$—B—C$_{1-5}$—N (termed HBS helices) have been previously developed (U.S. Pat. No. 7,202,332 to Arora & Chapman (HBS helices in which B is carbon); U.S. Provisional Patent Application No. 61/529,414 to Arora & Mahon (HBS helices in which B is sulfur, oxygen, or nitrogen), each of which is hereby incorporated in its entirety). The HBS approach provides a wide range of conformationally stable protein secondary structures, including α-helices, 3$_{10}$-helices, i-helices, gramicidin helices, β-turns, and β-sheet analogs (Chapman et al., *J. Am. Chem. Soc'y* 126:12252-53 (2004); Wang et al., *J. Am. Chem. Soc'y* 128:9248-56 (2006); Liu et al., *J. Am. Chem. Soc'y* 130:4334-37 (2008); Chapman et al., *Biochemistry* 47:4189-95 (2008), each of which is hereby incorporated by reference in its entirety). The internal placement of the crosslink allows the development of protein secondary structures such that none of the exposed surfaces are blocked by the constraining element—i.e., placement of the crosslink on the inside of the protein secondary structure does not alter side-chain functionality nor block solvent-exposed molecular recognition surfaces of the molecule (Wang et al., *Angew. Chem. Int'l Ed.* 44:6525 (2005); Sia et al., *Proc. Nat'l Acad. Sci. USA* 99:14664-14669 (2002), each of which is hereby incorporated by reference in its entirety). HBS helices can target their protein receptors with high affinity and specificity (Henchey et al., *ChemBioChem* 11:2104 (2010); Henchey et al., *J. Am. Chem. Soc'y* 132:941-43 (2010); Wang et al., *Angew. Chem. Int'l Ed.* 47:1879-82 (2008); Wang et al., *Angew. Chem. Int'l Ed.* 44:6525-29 (2005), each of which is hereby incorporated by reference in its entirety), and are cell permeable as compared to their unconstrained analogs (Henchey et al., *J. Am. Chem. Soc'y* 132:941-43 (2010), which is hereby incorporated by reference in its entirety). Moreover, even very short peptides (i.e., peptides less than 10 amino acid residues) may be constrained into highly stable protein secondary structures.

Figure 2A:
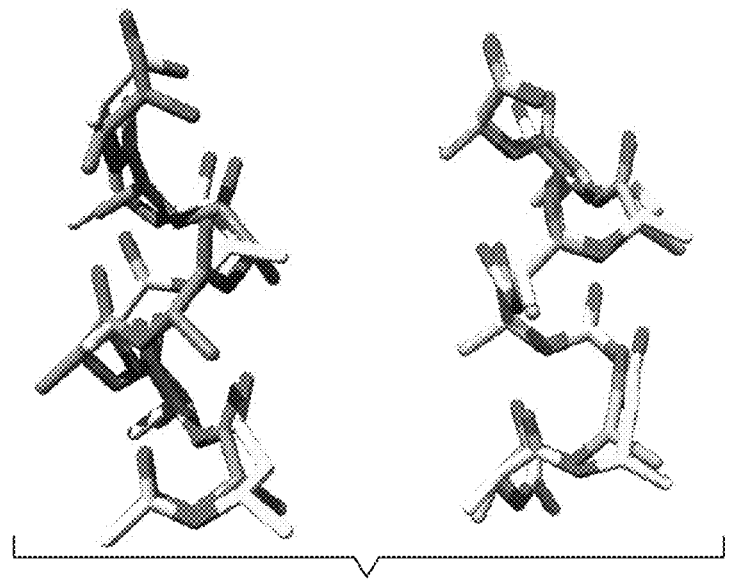
FIGS. 2A-B illustrate the $\alpha 3/\beta$ HBS approach to peptide mimic design.
Figure 2B:
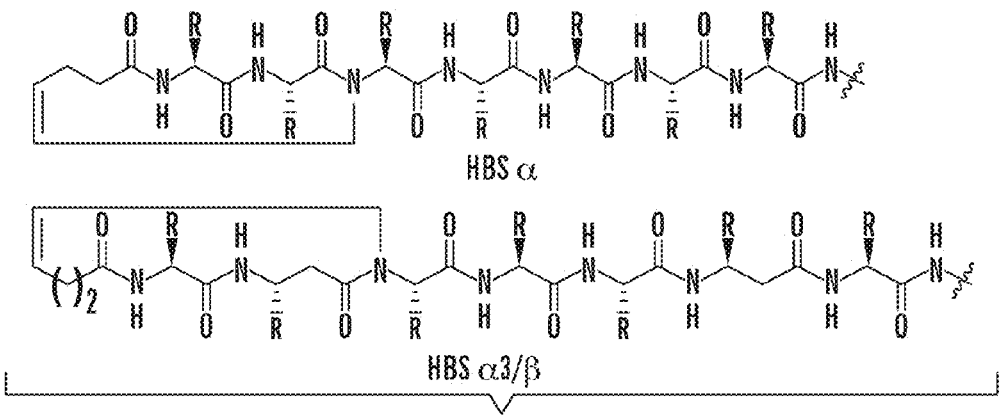

The design and evaluation of a new class of HBS helices (termed α/β HBS helices) that resist proteolytic degradation is described herein. Judicious insertion of beta amino acid residues into traditional HBS helices increases stability of synthetic helices against degradation without impairing their cell permeability or their capacity to target protein receptors with high affinity. It is expected that judicious insertion of beta amino acid residues into traditional HBS helices containing attached peptides increases stability of synthetic helices against degradation without impairing their cell permeability or their capacity to target protein receptors with high affinity. FIGS. 2A-B illustrate the α/β HBS approach to peptide mimic design, using α3/β1 peptides with beta amino acids in the macrocycle by way of example.

One aspect of the present invention relates to a peptidomimetic having a stable, internally constrained protein secondary structure, wherein the peptidomimetic is a compound of Formula I:

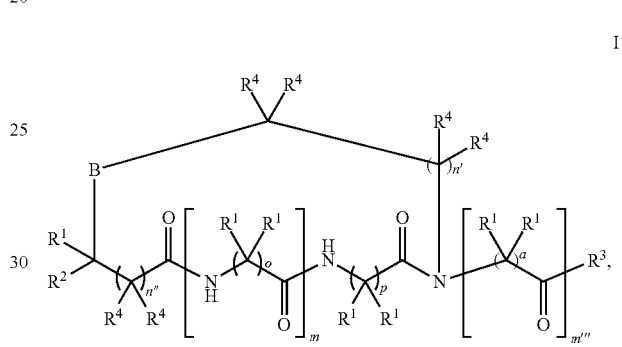

wherein:
B is C(R$^1$)$_2$, O, S, or NR$^1$;
each R$^1$ is independently hydrogen, an amino acid side chain, an alkyl, an alkenyl, an alkynyl, a cycloalkyl, a heterocyclyl, an aryl, a heteroaryl, or an arylalkyl;
R$^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

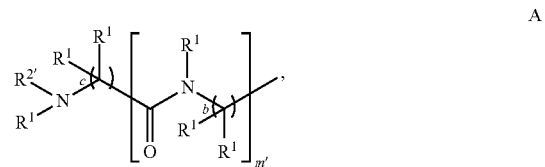

wherein:
R$^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;

each b is independently one or two; and c is one or two;

R$^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

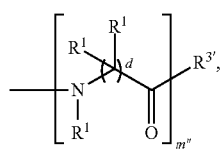

B wherein:

R$^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and each d is independently one or two;

each R$^4$ is independently hydrogen, an alkyl, an alkenyl, an alkynyl, a cycloalkyl, a heterocyclyl, an aryl, a heteroaryl, or an arylalkyl;

m, n', and n" are each independently zero, one, two, three, or four, wherein the sum of m, n', and n" is from two to six;

m''' is zero or one;

a is one or two;

each o is independently one or two;

p is one or two; and wherein at least one of the following conditions is met (i) m is one, two, three, or four and at least one o is two;
(ii) p is two;
(iii) m''' is one and a is two;
(iv) R$^2$ is a beta amino acid;
(v) R$^2$ is a moiety of Formula A wherein m' is at least one and at least one b is two;
(vi) R$^2$ is a moiety of Formula A wherein c is two;
(vii) R$^2$ is a moiety of Formula A wherein R$^{2'}$ is a beta amino acid;
(viii) R$^3$ is a beta amino acid;
(ix) R$^3$ is a moiety of Formula B wherein m" is at least one and at least one d is two; and
(x) R$^3$ is a moiety of Formula B wherein R$^{3'}$ is a beta amino acid.

Amino acid side chains according to this and all aspects of the present invention can be any amino acid side chain from natural or nonnatural amino acids, including from alpha amino acids, beta amino acids, gamma amino acids, L-amino acids, and D-amino acids.

As used herein, the term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon—carbon double bond and which may be straight or branched having about 2 to about 6 carbon atoms in the chain. Preferred alkenyl groups have 2 to about 4 carbon atoms in the chain. Exemplary alkenyl groups include ethenyl, propenyl, n-butenyl, and i-butenyl.

The term "alkynyl" means an aliphatic hydrocarbon group containing a carbon—carbon triple bond and which may be straight or branched having about 2 to about 6 carbon atoms in the chain. Preferred alkynyl groups have 2 to about 4 carbon atoms in the chain. Exemplary alkynyl groups include ethynyl, propynyl, n-butynyl, 2-butynyl, 3-methylbutynyl, and n-pentynyl.

As used herein, the term "cycloalkyl" refers to a non-aromatic saturated or unsaturated mono- or polycyclic ring system which may contain 3 to 6 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, the term "heterocyclyl" refers to a stable 3- to 18-membered ring system that consists of carbon atoms and from one to five heteroatoms selected from the group consisting of nitrogen, oxygen, and sulfur. The heterocyclyl may be a monocyclic or a polycyclic ring system, which may include fused, bridged, or spiro ring systems; and the nitrogen, carbon, or sulfur atoms in the heterocyclyl may be optionally oxidized; the nitrogen atom may be optionally quaternized; and the ring may be partially or fully saturated. Representative monocyclic heterocyclyls include piperidine, piperazine, pyrimidine, morpholine, thiomorpholine, pyrrolidine, tetrahydrofuran, pyran, tetrahydropyran, oxetane, and the like. Representative polycyclic heterocyclyls include indole, isoindole, indolizine, quinoline, isoquinoline, purine, carbazole, dibenzofuran, chromene, xanthene, and the like.

As used herein, the term "aryl" refers to an aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, "heteroaryl" refers to an aromatic ring system that consists of carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuryl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl.

The term "arylalkyl" refers to a moiety of the formula —$R^a R^b$ where $R^a$ is an alkyl or cycloalkyl as defined above and $R^b$ is an aryl or heteroaryl as defined above.

As used herein, the term "acyl" means a moiety of formula R-carbonyl, where R is an alkyl, cycloalkyl, aryl, or heteroaryl as defined above. Exemplary acyl groups include formyl, acetyl, propanoyl, benzoyl, and propenoyl.

An amino acid according to this and all aspects of the present invention can be any natural or non-natural amino acid.

A "peptide" as used herein is any oligomer of two or more natural or non-natural amino acids, including alpha amino acids, beta amino acids, gamma amino acids, L-amino acids, D-amino acids, and combinations thereof. In preferred embodiments, the peptide is ~5 to ~30 (e.g., ~5 to ~10, ~5 to ~17, ~10 to ~17, ~10 to ~30, or ~18 to ~30) amino acids in length. Typically, the peptide is 10-17 amino acids in length. In a preferred embodiment, the peptide contains a mixture of alpha and beta amino acids in the pattern α3/β1 (this is particularly preferred for α-helix mimetics).

A "tag" as used herein includes any labeling moiety that facilitates the detection, quantitation, separation, and/or purification of the compounds of the present invention. Suitable tags include purification tags, radioactive or fluorescent labels, and enzymatic tags.

Purification tags, such as poly-histidine ($His_6$-), a glutathione-S-transferase (GST-), or maltose-binding protein (MBP-), can assist in compound purification or separation but can later be removed, i.e., cleaved from the compound following recovery. Protease-specific cleavage sites can be used to facilitate the removal of the purification tag. The desired product can be purified further to remove the cleaved purification tags.

Other suitable tags include radioactive labels, such as, $^{125}I$, $^{131}I$, $^{111}In$, or $^{99}TC$. Methods of radiolabeling compounds are known in the art and described in U.S. Pat. No. 5,830,431 to Srinivasan et al., which is hereby incorporated by reference in its entirety. Radioactivity is detected and quantified using a scintillation counter or autoradiography. Alternatively, the compound can be conjugated to a fluorescent tag. Suitable fluorescent tags include, without limitation, chelates (europium chelates), fluorescein and its derivatives, rhodamine and its derivatives, dansyl, Lissamine, phycoerythrin, and Texas Red. The fluorescent labels can be conjugated to the compounds using techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Enzymatic tags generally catalyze a chemical alteration of a chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Examples of suitable enzymatic tags include luciferases (e.g., firefly luciferase and bacterial luciferase; see e.g., U.S. Pat. No. 4,737,456 to Weng et al., which is hereby incorporated by reference in its entirety), luciferin, 2,3-dihydrophthalazinediones, malate dehydrogenase, urease, peroxidases (e.g., horseradish peroxidase), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase, and the like. Techniques for conjugating enzymes to proteins and peptides are described in O'Sullivan et al., *Methods for the Preparation of Enzyme—Antibody Conjugates for Use in Enzyme Immunoassay*, in METHODS IN ENZYMOLOGY 147-66 (Langone et al. eds., 1981), which is hereby incorporated by reference in its entirety.

A targeting moiety according to the present invention functions to (i) promote the cellular uptake of the compound, (ii) target the compound to a particular cell or tissue type (e.g., signaling peptide sequence), or (iii) target the compound to a specific sub-cellular localization after cellular uptake (e.g., transport peptide sequence).

To promote the cellular uptake of a compound of the present invention, the targeting moiety may be a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem.* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety.

Another suitable targeting moiety useful for enhancing the cellular uptake of a compound is an "importation competent" signal peptide as disclosed by U.S. Pat. No. 6,043,339 to Lin et al., which is hereby incorporated by reference in its entirety. An importation competent signal peptide is generally about 10 to about 50 amino acid residues in length—typically hydrophobic residues—that render the compound capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety).

Another suitable targeting moiety is a signal peptide sequence capable of targeting the compounds of the present invention to a particular tissue or cell type. The signaling peptide can include at least a portion of a ligand binding protein. Suitable ligand binding proteins include high-affinity antibody fragments (e.g., Fab, Fab' and $F(ab')_2$, single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified compound is delivered intravenously or otherwise introduced into blood or lymph, the compound will adsorb to the targeted cell, and the targeted cell will internalize the compound. For example, if the target cell is a cancer cell, the compound may be conjugated to an anti-C3B(I) antibody as disclosed by U.S. Pat. No. 6,572,856 to Taylor et al., which is hereby incorporated by reference in its entirety. Alternatively, the compound may be conjugated to an alphafeto protein receptor as disclosed by U.S. Pat. No. 6,514,685 to Moro, which is hereby incorporated by reference in its entirety, or to a monoclonal GAH antibody as disclosed by U.S. Pat. No. 5,837,845 to Hosokawa, which is hereby incorporated by reference in its entirety. For targeting a compound to a cardiac cell, the compound may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. For targeting a compound to a hepatic cell, the signaling peptide may include a ligand domain specific to the hepatocyte-specific asialoglycoprotein receptor. Methods of preparing such chimeric proteins and peptides are described in U.S. Pat. No. 5,817,789 to Heartlein et al., which is hereby incorporated by reference in its entirety.

Another suitable targeting moiety is a transport peptide that directs intracellular compartmentalization of the compound once it is internalized by a target cell or tissue. For transport to the endoplasmic reticulum (ER), for example, the compound can be conjugated to an ER transport peptide sequence. A number of such signal peptides are known in the art, including the signal peptide MMSFVSLLLVGILFYATE-AEQLTKCEVFQ (SEQ ID NO: 1). Other suitable ER signal peptides include the N-terminus endoplasmic reticulum targeting sequence of the enzyme 17β-hydroxysteroid dehydrogenase type 11 (Horiguchi et al., "Identification and Characterization of the ER/Lipid Droplet-Targeting Sequence in 17β-hydroxysteroid Dehydrogenase Type 11," *Arch. Biochem. Biophys.* 479(2):121-30 (2008), which is hereby incorporated by reference in its entirety), or any of the ER signaling peptides (including the nucleic acid sequences encoding the ER signal peptides) disclosed in U.S. Patent Application Publication No. 20080250515 to Reed et al., which is hereby incorporated by reference in its entirety. Additionally, the compound of the present invention can contain an ER retention signal, such as the retention signal KEDL (SEQ ID NO: 2). Methods of modifying the compounds of the present invention to incorporate transport peptides for localization of the compounds to the ER can be carried out as described in U.S. Patent Application Publication No. 20080250515 to Reed et al., which is hereby incorporated by reference in its entirety.

For transport to the nucleus, the compounds of the present invention can include a nuclear localization transport signal. Suitable nuclear transport peptide sequences are known in the art, including the nuclear transport peptide PPKKKRKV (SEQ ID NO:3). Other nuclear localization transport signals include, for example, the nuclear localization sequence of acidic fibroblast growth factor and the nuclear localization sequence of the transcription factor NF-KB p50 as disclosed by U.S. Pat. No. 6,043,339 to Lin et al., which is hereby incorporated by reference in its entirety. Other nuclear localization peptide sequences known in the art are also suitable for use in the compounds of the present invention.

Suitable transport peptide sequences for targeting to the mitochondria include MLSLRQSIRFFKPATRTLCSSRYLL (SEQ ID NO: 4). Other suitable transport peptide sequences suitable for selectively targeting the compounds of the present invention to the mitochondria are disclosed in U.S. Patent Application Publication No. 20070161544 to Wipf, which is hereby incorporated by reference in its entirety.

As will be apparent to those of ordinary skill in the art, when $R^2$ and/or $R^3$ are a moiety of the recited formulae, the overall size of the compounds of Formula I can be adjusted by varying the values of m' and/or m'', which are independently zero or any number. Typically, m' and m'' are independently from zero to about thirty (e.g., 0 to ~18, 0 to ~10, 0 to ~5, ~5 to ~30, ~5 to ~18, ~5 to ~10, ~8 to ~30, ~8 to ~18, ~8 to ~10, ~10 to ~18, or ~10 to ~30). In one embodiment, m' and m'' are independently 4-10. In another embodiment, m' and m'' are independently 5-6.

As will be apparent to the skilled artisan, compounds of Formula I include a diverse range of helical conformation, which depends on the number of atoms in the backbone of the helical macrocycle (which can be controlled by adjusting the values of m, n', n'', o, and p). For helical conformations that mimic $3_{10}$-helices, the compound of Formula I has a total of 9-12 atoms (preferably 11 atoms) in the backbone of the macrocycle. For helical conformations that mimic α-helices, the compound of Formula I has a total of 12-15 atoms (preferably 14 atoms) in the backbone of the macrocycle. For helical conformations that mimic i-helices, the compound of Formula I has a total of 15-18 atoms (preferably 17 atoms) in the backbone of the macrocycle. For helical conformations that mimic gramicidin helices, the compound of Formula I has a total of 20-24 atoms (preferably 22 atoms) in the backbone of the macrocycle.

In at least one embodiment, m is one, two, three, or four and at least one o is two. In at least one embodiment, p is two. In at least one embodiment, m''' is one and a is two. In at least one embodiment, $R^2$ is: a beta amino acid, a moiety of Formula A where m' is at least one and at least one b is two, a moiety of Formula A where c is two, or a moiety of Formula A where $R^{2'}$ is a beta amino acid. In at least one embodiment, $R^3$ is: a beta amino acid, a moiety of Formula B where m'' is at least one and at least one d is two, or a moiety of Formula B where $R^{3'}$ is a beta amino acid. Combinations of these embodiments are also contemplated.

When $R^2$ is a moiety of Formula A, m' is preferably any number from one to 19. When $R^3$ is a moiety of Formula B, m'' is preferably any number from one to nine.

In preferred embodiments, the compound of Formula I is a compound of Formula IA (i.e., a helix cyclized at the N-terminal), Formula IB (i.e., a helix cyclized mid-peptide), or Formula IC (i.e., a helix cyclized at the C-terminal):

IA

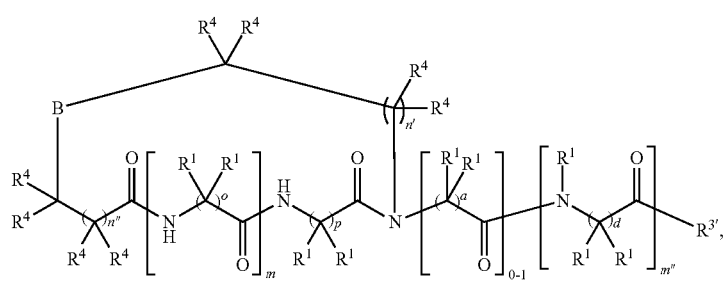

IB

IC

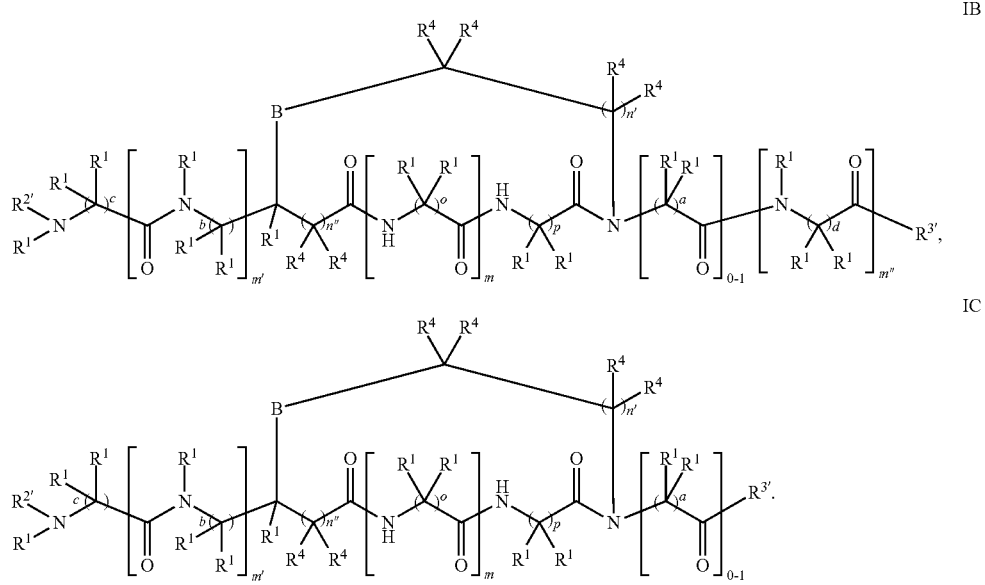

As will be apparent to the skilled artisan, the pattern of substitution in the peptidomimetics of Formula I can be controlled by adjusting the values for m and o, m'" and a, n', n", and p, as well as m', b, and c (when $R^2$ is a moiety of Formula A), and m" and d (when $R^3$ is a moiety of Formula B). Substitution in peptidomimetics of Formulae IA, IB, and IC can further be controlled as will be apparent to the skilled artisan. In a preferred embodiment, when the peptidomimetic contains an α-helical secondary structure, the peptidomimetic is of the formula α3/β1.

Another aspect of the present invention relates to compounds of Formula IIA (i.e., a β-sheet macrocycle) or Formula IIB (i.e., a β-hairpin):

IIA

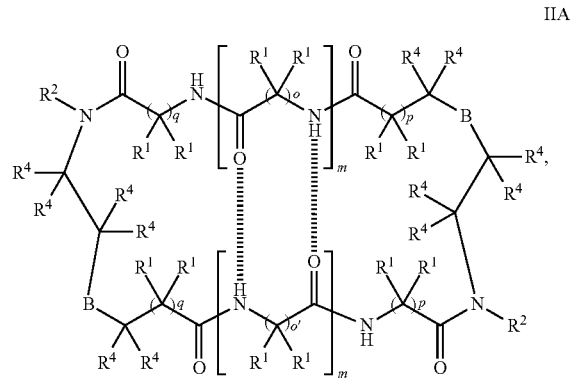

IIB

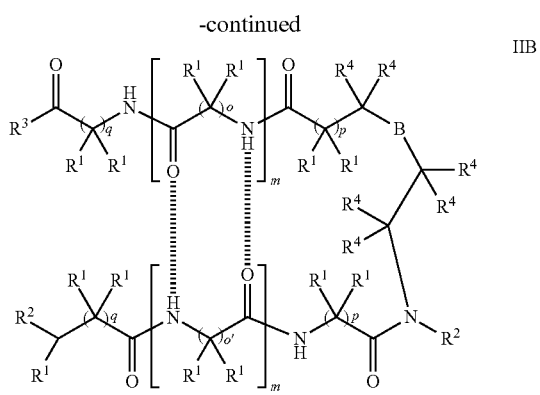

wherein:
each B is independently $C(R^1)_2$, O, S, or $NR^1$;
each $R^1$ is independently hydrogen, an amino acid side chain, an alkyl, an alkenyl, an alkynyl, a cycloalkyl, a heterocyclyl, an aryl, a heteroaryl, or an arylalkyl;
each $R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; $-OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; $-(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

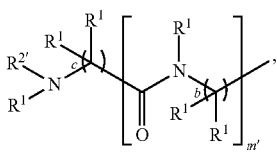

wherein:
R² is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH₂)₀₋₁N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m' is zero or any number;
each b is independently one or two; and
c is one or two;
R³ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

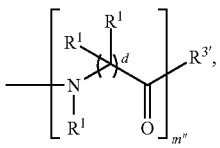

wherein:
R³' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —N(R⁵)₂ wherein alkenyl, an alkynyl, a cycloalkyl, a heterocyclyl, an aryl, a heteroaryl, an arylalkyl, an acyl, a peptide, a targeting moiety, or a tag;
m" is zero or any number; and
each d is independently one or two;
each R⁴ is independently hydrogen, an alkyl, an alkenyl, an alkynyl, a cycloalkyl, a heterocyclyl, an aryl, a heteroaryl, or an arylalkyl;
m is one, two, three, or four;
each o and each o' are independently one or two, with the proviso that each corresponding o and o' are the same;
p is one or two;
q is one or two; and
wherein at least one of the following conditions is met
(i) m is one, two, three, or four; at least one o is two; and at least one o' is two;
(ii) p is two;
(iii) q is two;
(iv) at least one R² is a beta amino acid;
(v) at least one R² is a moiety of Formula A wherein m' is at least one and at least one b is two;
(vi) at least one R² is a moiety of Formula A wherein c is two;
(vii) at least one R² is a moiety of Formula A wherein R²' is a beta amino acid;
(viii) R³ is a beta amino acid;
(ix) R³ is a moiety of Formula B wherein m" is at least one and at least one d is two; and
(x) R³ is a moiety of Formula B wherein R³' is a beta amino acid.

In at least one embodiment of this aspect of the present invention, m is one, two, three, or four; at least one o is two; and at least one o' is two. It at least one embodiment of this aspect of the present invention, p is two. It at least one embodiment of this aspect of the present invention, q is two.

In at least one embodiment, the compound is a compound of Formula IIA and R² is: a beta amino acid, a moiety of Formula A where m' is at least one and at least one b is two, a moiety of Formula A where c is two, or a moiety of Formula A where R²' is a beta amino acid.

In at least one embodiment in which the compound is a compound of Formula IIB, R² is: a beta amino acid, a moiety of Formula A where m' is at least one and at least one b is two, a moiety of Formula A where c is two, or a moiety of Formula A where R²' is a beta amino acid. In at least one embodiment in which the compound is a compound of Formula IIB, R³ is: a beta amino acid, a moiety of Formula B where m" is at least one and at least one d is two, or a moiety of Formula B where R³' is a beta amino acid. Combinations of these embodiments are also contemplated.

As will be apparent to the skilled artisan, the pattern of 13 substitution in the peptidomimetics of Formulae IIA and IIB can be controlled by adjusting the values for m and o, p, and q, as well as m', b, and c (when R² is a moiety of Formula A) and m" and d (when R³ is a moiety of Formula B).

The compounds according to all aspects of the present invention can be prepared using the methods disclosed in U.S. Pat. No. 7,202,332 to Arora & Chapman (when B is carbon) and U.S. Provisional Patent Application No. 61/529,414 to Arora & Mahon (when B is S, O, or N), each of which is hereby incorporated by reference in its entirety), but using beta amino acids in place of alpha amino acids, as appropriate.

Yet another aspect of the present invention relates to a method for promoting cell death. This method involves contacting a cell with one or more compounds of Formula I that inhibit p53/hDM2, under conditions effective for the one or more compounds to promote cell death.

Suitable p53/hDM2 inhibitors include peptide 1, described infra.

The p53/hDM2 interaction is known to stop apoptosis and lead to uncontrolled growth (a characteristic of cancer). Peptide 1 mimics a portion of p53 protein that binds to hDM2; peptides that mimic a portion of p53 protein that binds to hDM2 are expected to block p53/hDM2 interaction and induce apoptotic activity in cancer cells (Chene, P, "Inhibiting the p53-MDM2 Interaction: An Important Target For Cancer Therapy," *Nat. Rev. Cancer* 3:102-109 (2003); Chene et al., "Study of the Cytotoxic Effect of a Peptidic Inhibitor of the p53-HDN2 Interaction in Tumor Cells," *FEBS Lett.* 529:293-297 (2002); Garcia-Echeverria et al., "Discovery of Potent Antagonists of the Interaction between Human Double Mminute 2 and Tumor Suppressor p53," *J. Medicinal Chemistry* 43:3205-3208 (2000); Kritzer et al., "Helical β-Peptide Inhibitors of the p53-hDM2 Interaction," *J. Am. Chem. Soc.* 126:9468-9469 (2004); Kussie et al, "Structure of the MDM2 Oncoprotein Bound to the p53 Tumor Suppressor Transactivation Domain," *Science* 274: 948-953 (1996); Vassilev et al. "In Vivo Activation of the p53 Pathway by Small-molecule Antagonists of MDM2," *Science* 303:844-848 (2004); Yin et al., "Terphenyl-based Helical Mimetics That Disrupt the p53/HDM2 Interaction," *Angew Chem. Int. Ed.* 44:2704-2707 (2005), which are hereby incorporated by reference in their entirety).

Contacting a cell with one or more compounds according to this aspect of the present invention may be carried out in vitro or in vivo.

When contacting is carried out in vivo, contacting may comprise administering to a subject a compound that includes one or more compounds of the present invention. The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When using this method to treat a subject, the above-mentioned modes and forms of administering are used to contact the cell with the one or more compounds of Formula I.

The present invention may be further illustrated by reference to the following examples.

EXAMPLES

Example 1

General

Commercial-grade reagents and solvents were used without further purification except as indicated. Dichloroethane was distilled before use in the metathesis reactions. All reactions were stirred magnetically or mechanically shaken; moisture-sensitive reactions were performed under nitrogen or argon atmosphere. Reverse-phase HPLC experiments were conducted with 0.1% aqueous trifluoroacetic acid and 0.1% trifluoroacetic acid in acetonitrile buffers as eluents on $C_{18}$ reversed-phase columns using a Beckman Coulter HPLC equipped with a System Gold 168 Diode array detector. ESIMS data was obtained on an Agilent 1100 series LC/MSD (XCT) electrospray trap. The microwave reactions were performed in the CEM Discover single-mode reactor with controlled power, temperature, and time settings. Proton NMR spectra of HBS peptides were recorded on a Bruker AVANCE 900 MHz spectrometer.

Example 2

Synthesis of HBS Helices with β-Amino Acid(s) in the Macrocycle

HBS peptides 1, 2, 5, and Flu-1 were synthesized as shown in Scheme 1 and as described in U.S. Pat. No. 7,202,332 to Arora & Chapman; Chapman & Arora, *Org. Lett.* 8:5825-28 (2006); Dimartino et al., *Org. Lett.* 7:2389-92 (2005); Patgiri et al., *Nat. Protoc.* 5:1857-65 (2010); and Patgiri et al., *Org. Biomol. Chem.* 8:1773-76 (2010), each of which is hereby incorporated by reference in its entirety.

peptide (Patgiri et al., *Nat. Protoc.* 5:1857 (2010), which is hereby incorporated by reference in its entirety). Resin containing peptide 12 was washed with DMF (×3), methanol

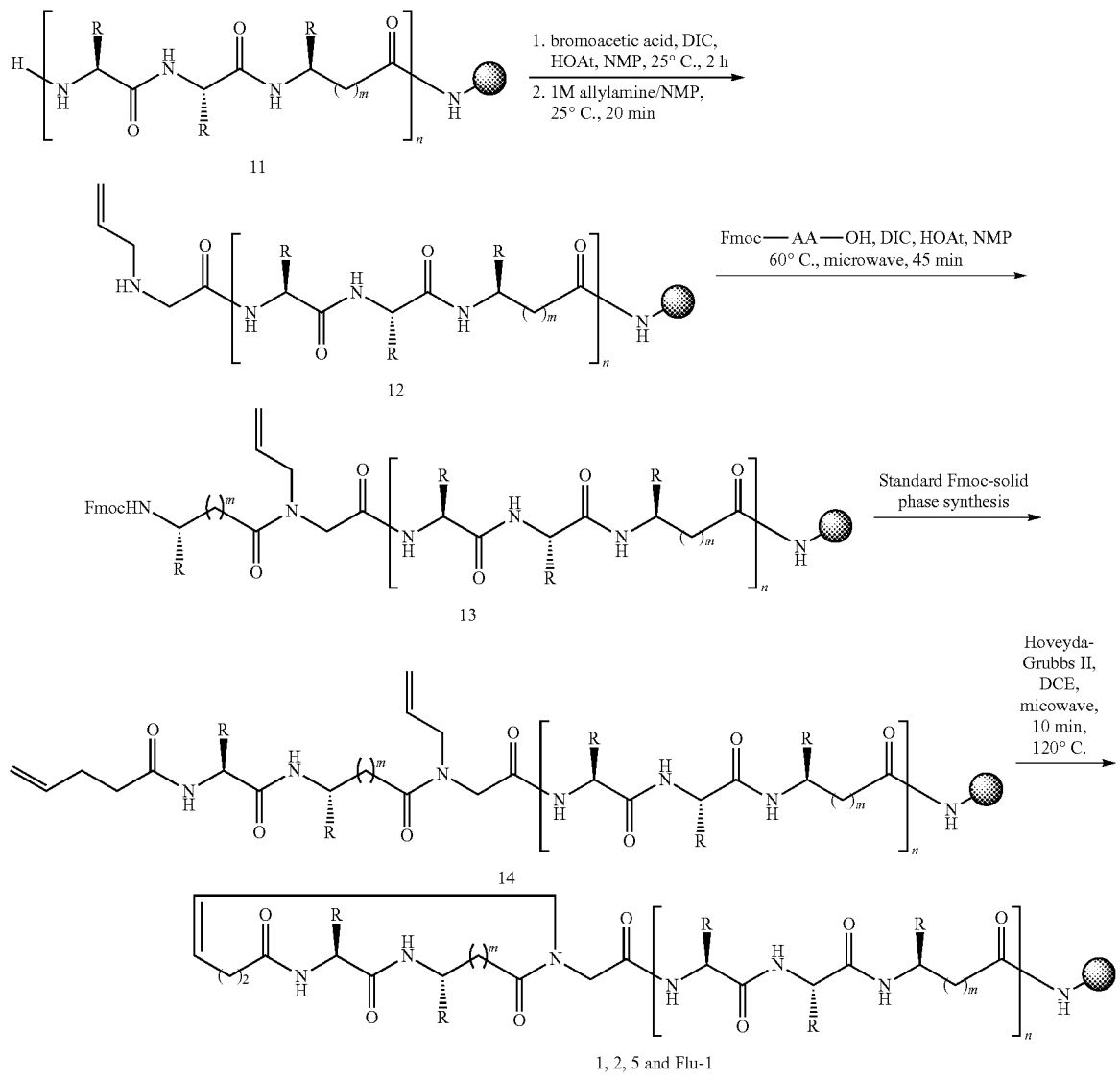

m = 0 for α-amino acid residues and 1 for β³-amino acid residues

Briefly, peptide sequences up to the i+5$^{th}$ residue of the putative helix (peptide 11 in Scheme 1) were synthesized using Fmoc solid-phase chemistry on Rink amide resin on a CEM Liberty Series microwave peptide synthesizer.

N-allylation of the i+4$^{th}$ residue (peptide 12 in Scheme 1) was achieved over two steps by coupling of bromoacetic acid followed by an allylamine displacement reaction. Resin bound peptide 11 was treated with a solution of bromoacetic acid (20 eq), DIC (20 eq), and HOAt (10 eq) in DMF, and the mixture shaken for 2 hours at room temperature. Resin was washed sequentially with DMF (×3), DCM (×3), and DMF (×3), suspended in 1 M allylamine (20 eq) in DMF, and shaken for 20 minutes.

Coupling of the next two Fmoc-amino acid residues, followed by addition of 4-pentenoic acid, afforded the bis-olefin (×3), and DCM (×3), and treated with the desired Fmoc amino acid (20 eq), DIC (20 eq), and HOAt (10 eq) in DMF under microwave irradiation for 45 minutes at 60° C. Resin containing peptide 13 was then washed with DMF (×3), DCM (×3), and DMF (×3), and coupled to the desired Fmoc amino acid residue (5 eq) and 4-pentenoic acid (5 eq) with HBTU (4.95 eq) and DIEA (10 eq) in NMP.

Ring-closing metathesis of the bis-olefin peptide 14 was performed with Hoveyda-Grubbs II catalyst (20 mol %) in dichloroethane under microwave irradiation at 120° C. for 10 minutes (U.S. Pat. No. 7,202,332 to Arora & Chapman; Chapman & Arora, *Org. Lett.* 8:5825-28 (2006); Patgiri et al., *Nat. Protoc.* 5:1857-65 (2010); Patgiri et al., *Org. Biomol. Chem.* 8:1773-76 (2010), each of which is hereby incorporated by reference in its entirety). Metathesized peptides were cleaved from the resin using TFA:TIS:water (95:2.5:2.5).

Linear peptides were prepared as described in Coin et al., *Nat. Protocols* 2:3247-56 (2007), and FMOC SOLID PHASE PEPTIDE SYNTHESIS: A PRACTICAL APPROACH (W. C. Chan & P. D. White eds., 2000), each of which is hereby incorporated by reference in its entirety.

Figure 3:
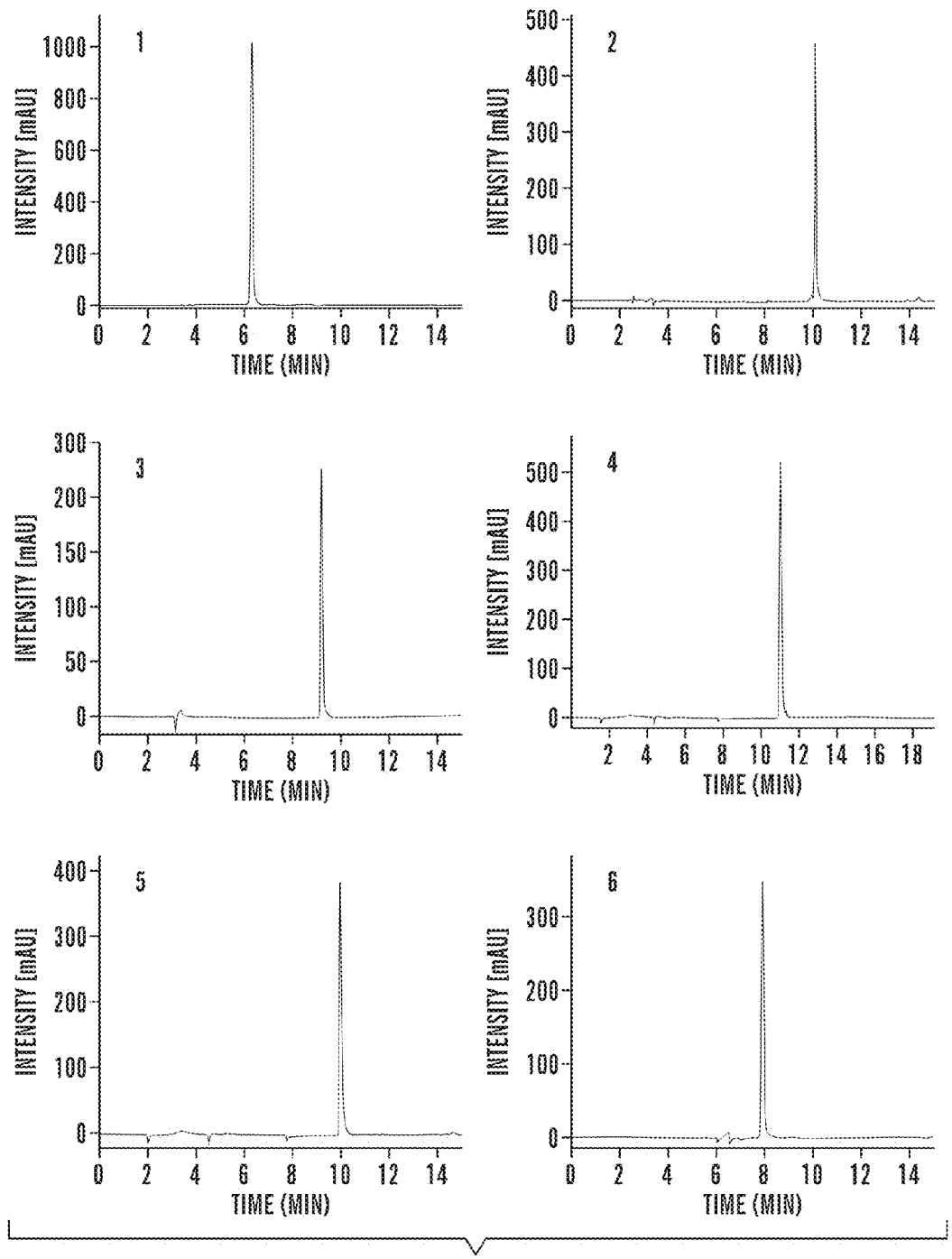
FIG. 3 is a series of analytical HPLC traces of peptides 1 ($\alpha 3/\beta$-HBS peptide, top left), 2 ($\alpha$-HBS, top right), 3 (unconstrained $\alpha 3/\beta$, center left), 4 (unconstrained $\alpha 3/\beta_{cyclo}$, center right), 5 ($\alpha 3/\beta$-HBS$_{mut}$, bottom left), and 6 (unconstrained $\alpha$, bottom right).

All peptides were purified by reversed-phase HPLC($C_{18}$ column) (FIG. 3) and characterized by ESI-MS (Table 1).

TABLE 1

Mass spectroscopic characterization of HBS helices and unconstrained peptides.

| Peptide | Sequence[a] | Calculated [M+H]+ | Observed [M+H]+ |
|---|---|---|---|
| 1 | XQeG*FSdLWKILS-NH$_2$ (SEQ ID NO: 5) | 1557.8 | 1558.7 |
| 2 | XQEG*FSDLWKLLS-NH$_2$ (SEQ ID NO: 6) | 1514.7 | 1515.0 |
| 3 | Ac-QeGFSdLWKILS-NH$_2$ (SEQ ID NO: 7) | 1505.7 | 1505.2 |
| 4 | Ac-Q(ACPC)GFS(ACPC)LWK(ACPC)LS-NH$_2$ (SEQ ID NO: 8) | 1438.8 | 1439.9 |
| 5 | XQeG*ASdLWKIAS-NH$_2$ (SEQ ID NO: 9) | 1438.8 | 1439.0 |
| 6 | Ac-QEGFSDLWKLLS-NH$_2$ (SEQ ID NO: 10) | 1462.8 | 1463.0 |
| Flu-1XQeG*FSdLWKILSC$^{Flu}$-NH$_2$ (SEQ ID NO: 11) | | 2048.2 | 2048.8 |
| Flu-3Ac-QeGFSdLWKILSC$^{Flu}$-NH$_2$ (SEQ ID NO: 12) | | 1996.2 | 1996.7 |
| Flu- Ac-EAFSDLWKLLPENNVC$^{Flu}$-NH$_2$ p53 (SEQ ID NO: 13) | | 2305.0 | 1153.0* |

[a]Lower-case bold letters denote $\beta^3$-residues; X is pentenoic acid; G* is N-allyl glycine; ACPC is cyclic β residue (1S,2S)-2-aminocyclopentane carboxylic acid; Flu is 5-acetamidofluorescein. *(M+2)$^{2+}$ Example 3

Synthesis of 5-Carboxyfluorescein Labeled Peptides

Figure 4:
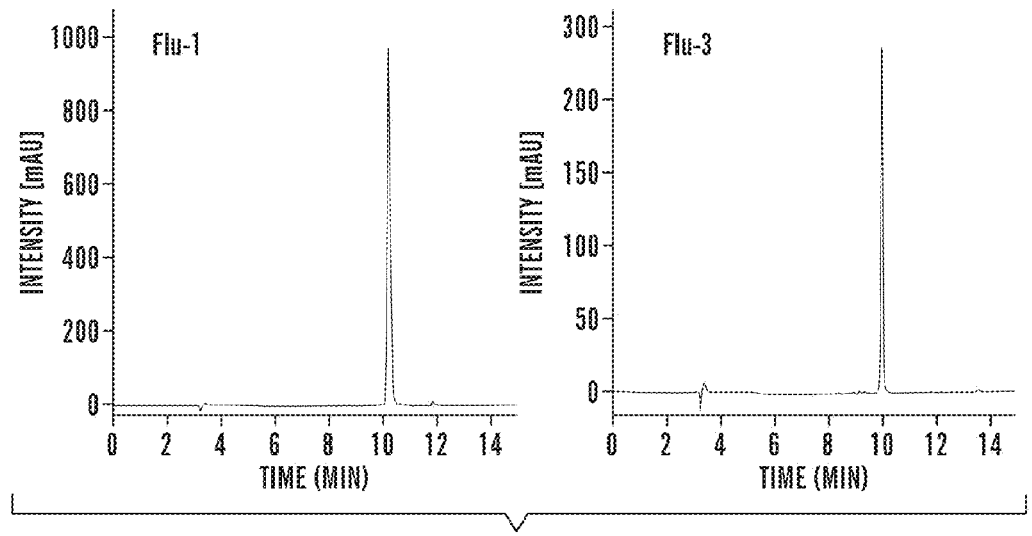
FIG. 4 is a pair of analytical HPLC traces of peptides Flu-1 (left) and Flu-3 (right).

HBS helices and unconstrained peptides containing C-terminal Cys residues were synthesized as described in Example 2 supra. After cleavage and purification, peptides were treated with 5-Iodoacetamidofluorescein (5-IAF, 5 eq) in 10 mM PBS (pH 7.4) for 2 hours at room temperature. The fluorescein conjugates were purified by reversed-phase HPLC ($C_{18}$ column) (FIG. 4). The identity and the purity of the peptides were confirmed by ESI-MS (Table 1, supra).

Example 4

Circular Dichroism Spectroscopy

Figure 5:
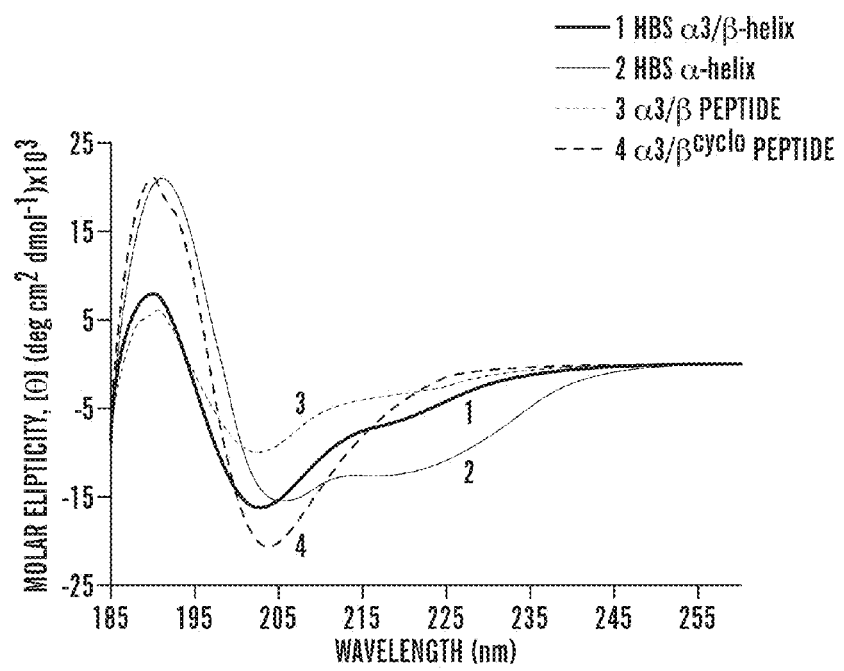
FIG. 5 is the circular dichroism spectra of peptides 1-4. The CD spectra were obtained in 10% TFE/PBS.
Figure 6:
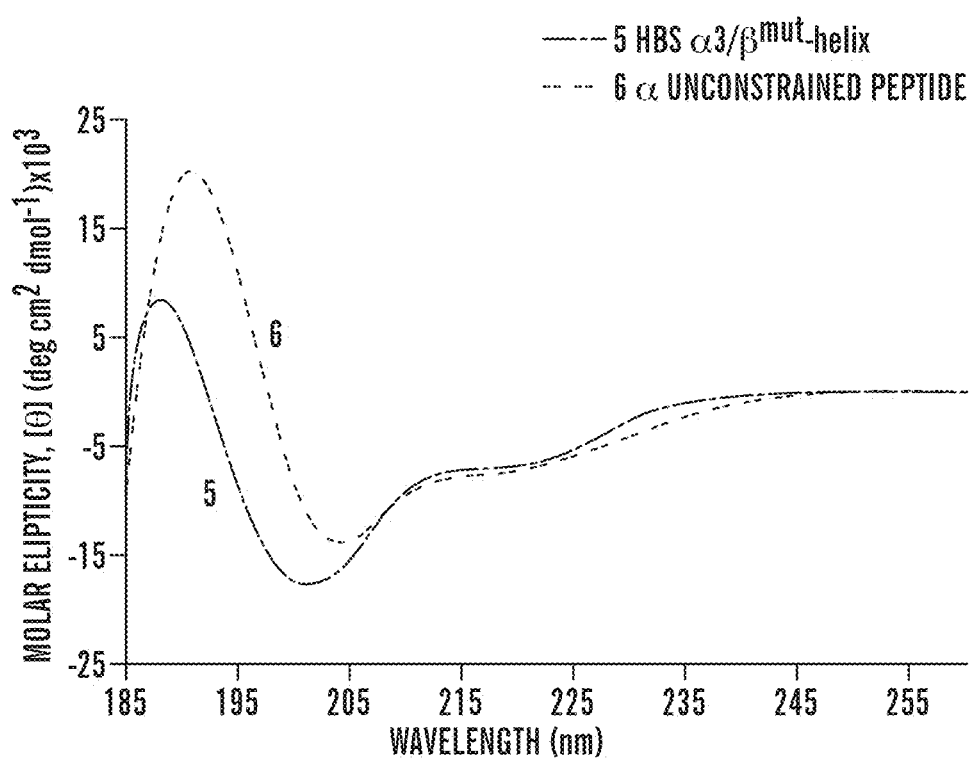
FIG. 6 is the circular dichroism spectrum of peptide 5 and peptide 6 in 10% TFE in PBS.
Figure 7:
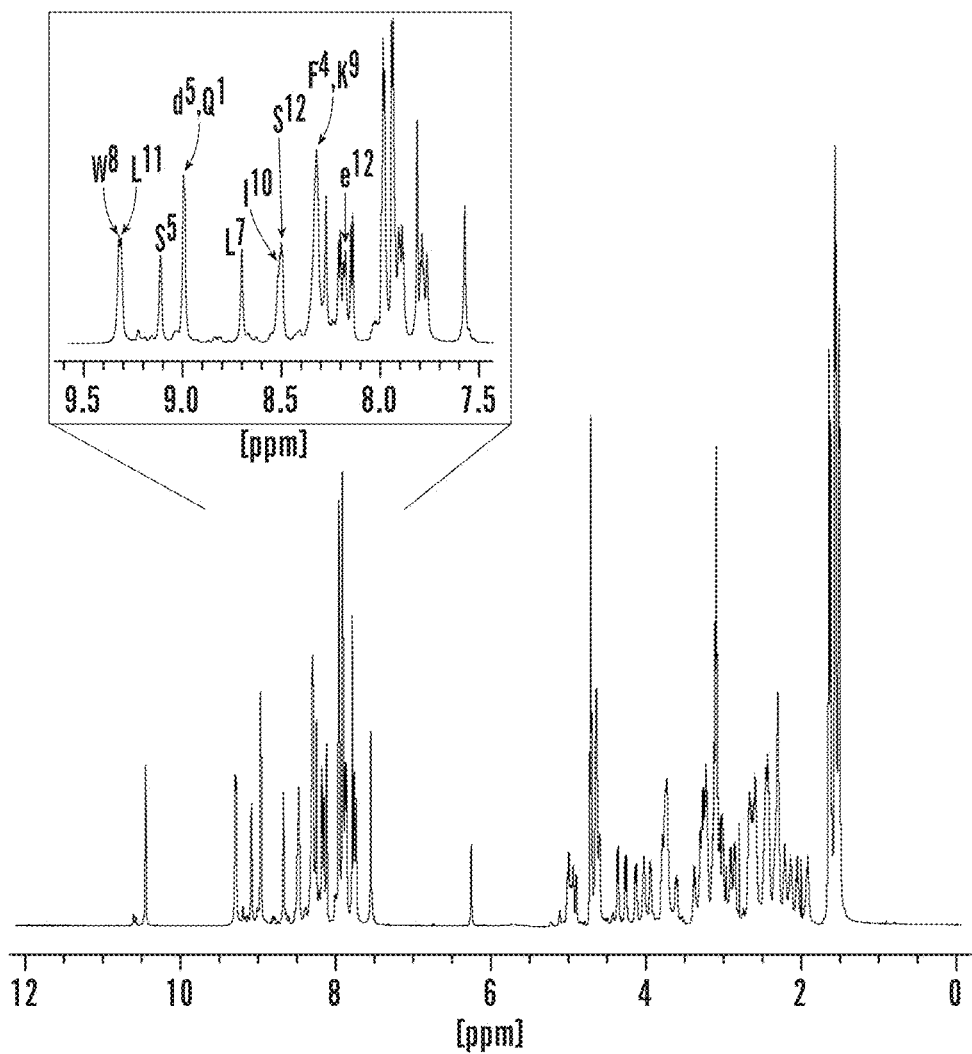
FIG. 7 is the $^1$H NMR of peptide 1 in 20% TFE-d3 in PBS at 293 K on a 900 MHz NMR spectrometer. Assignments of the NH protons are shown in the inset. The $\beta^3$-amino acid residues are shown in lower-case blue letters.
Figure 8:
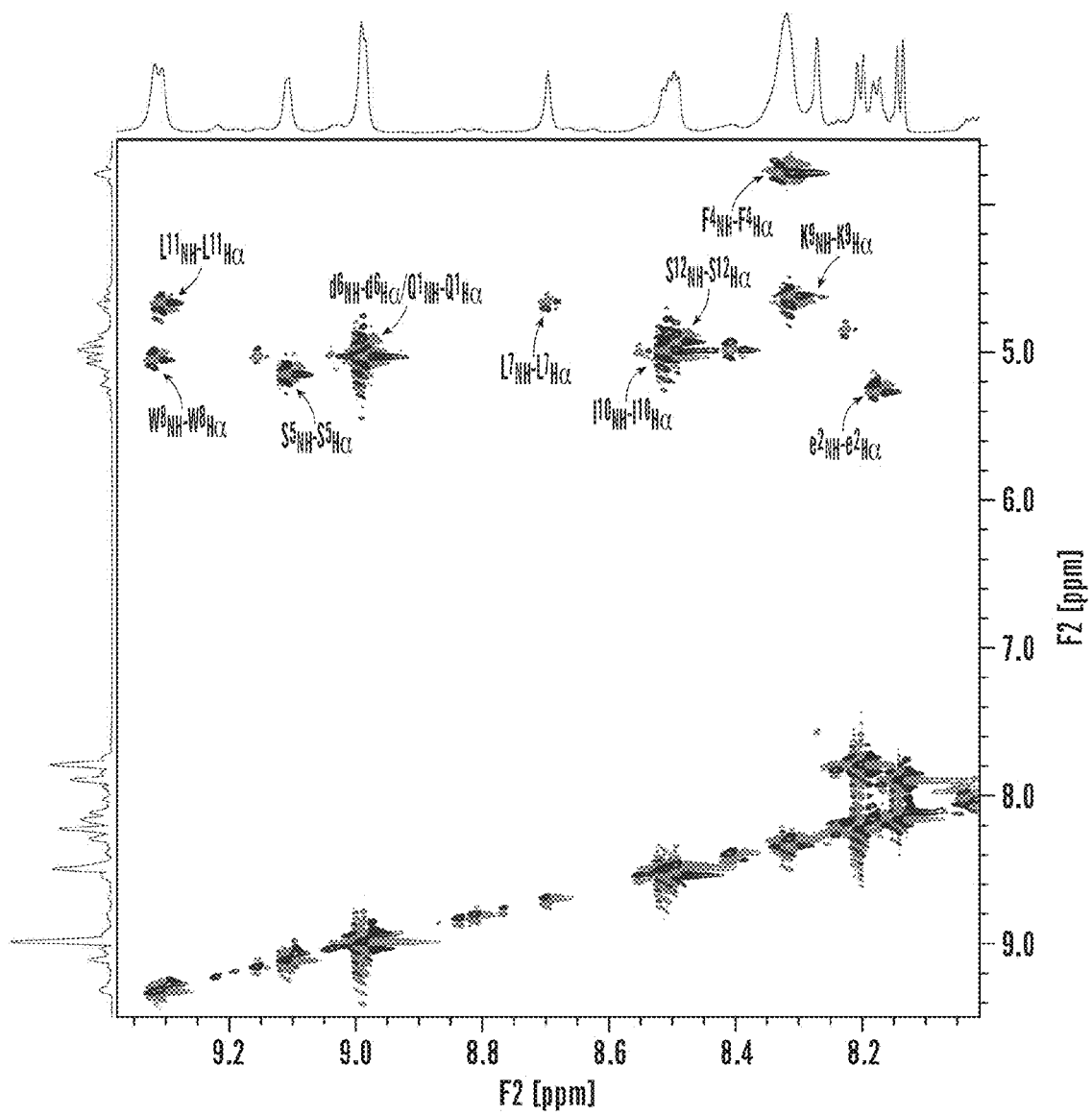
FIG. 8 is the fingerprint region of the 900 MHz DQF-COSY spectrum (293 K) of peptide 1 in 20% TFE-d3 in PBS. The connections of the backbone amide protons and C$\alpha$ protons are shown by arrows. The $\beta^3$-amino acid residues are shown in lower-case blue letters.
Figure 9:
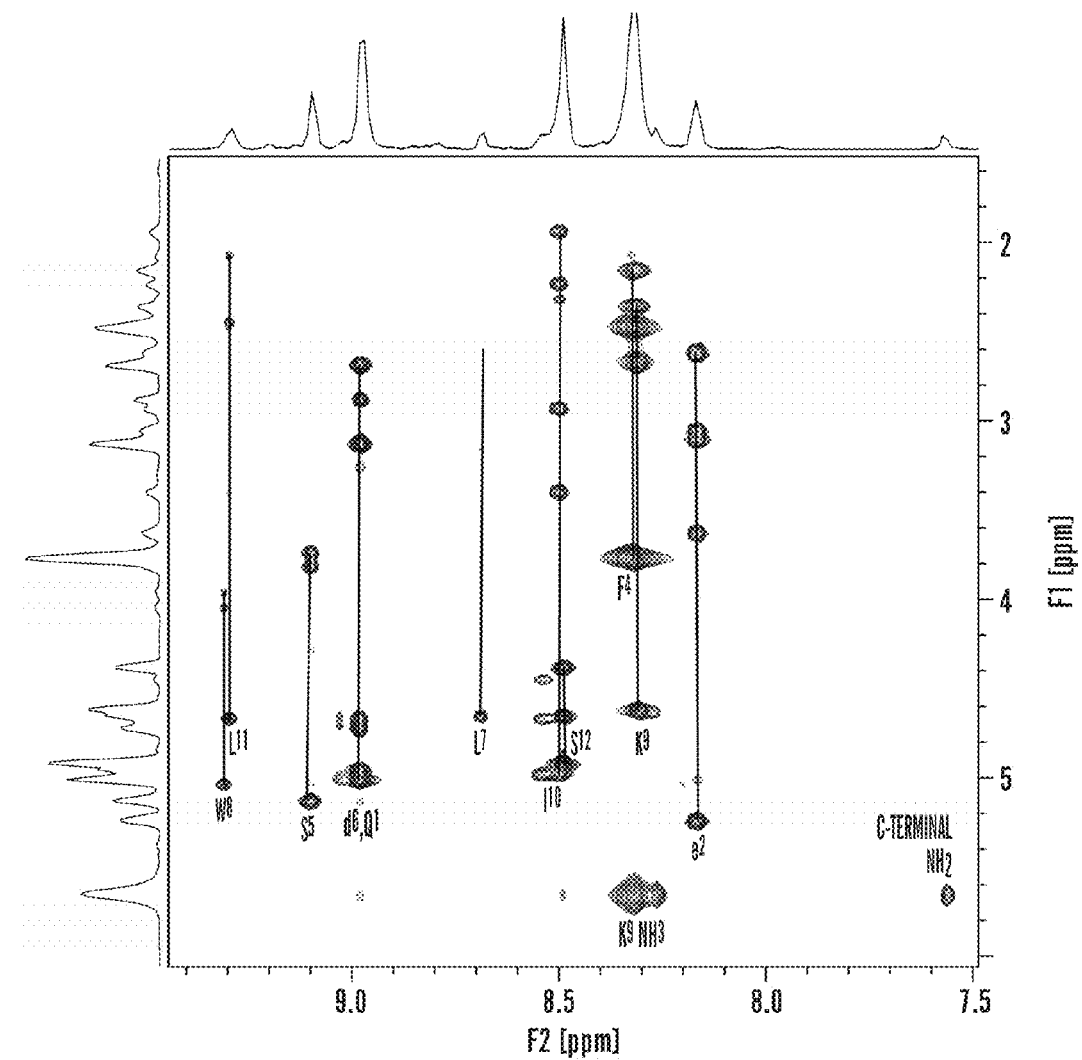
FIG. 9 is the NH—C$\alpha$ region of the 900 MHz TOCSY spectrum (293 K) of peptide 1 in 20% TFE-d3 in PBS. $\beta^3$-amino acid residues are denoted with lower-case blue letters.
Figure 10:
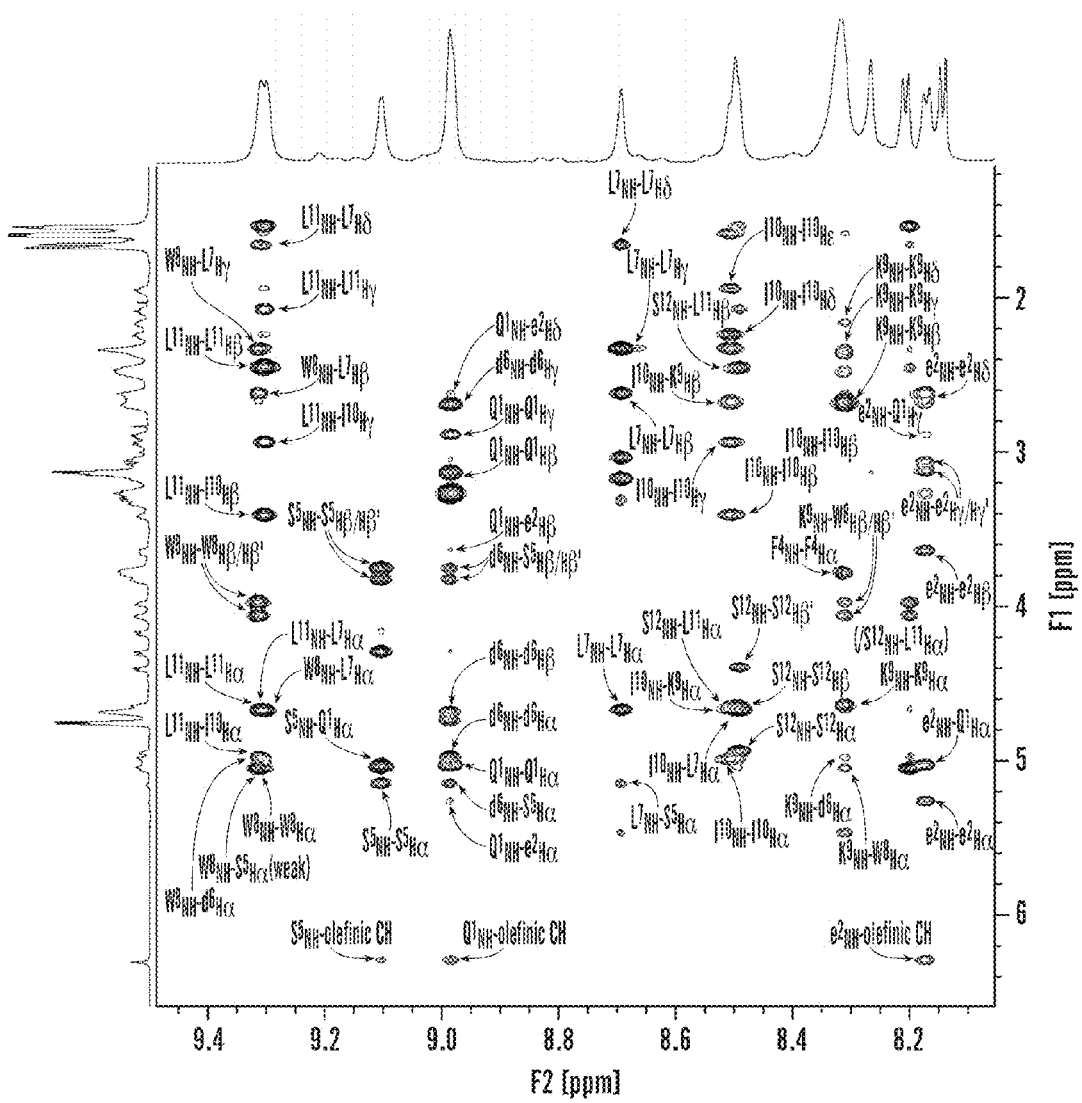
FIG. 10 is a region of the NOESY spectrum (900 MHz, 293 K) of peptide 1 in 20% TFE-d3 in PBS. $\beta^3$-Amino acid residues are shown in lower-case blue letters.
Figure 11:
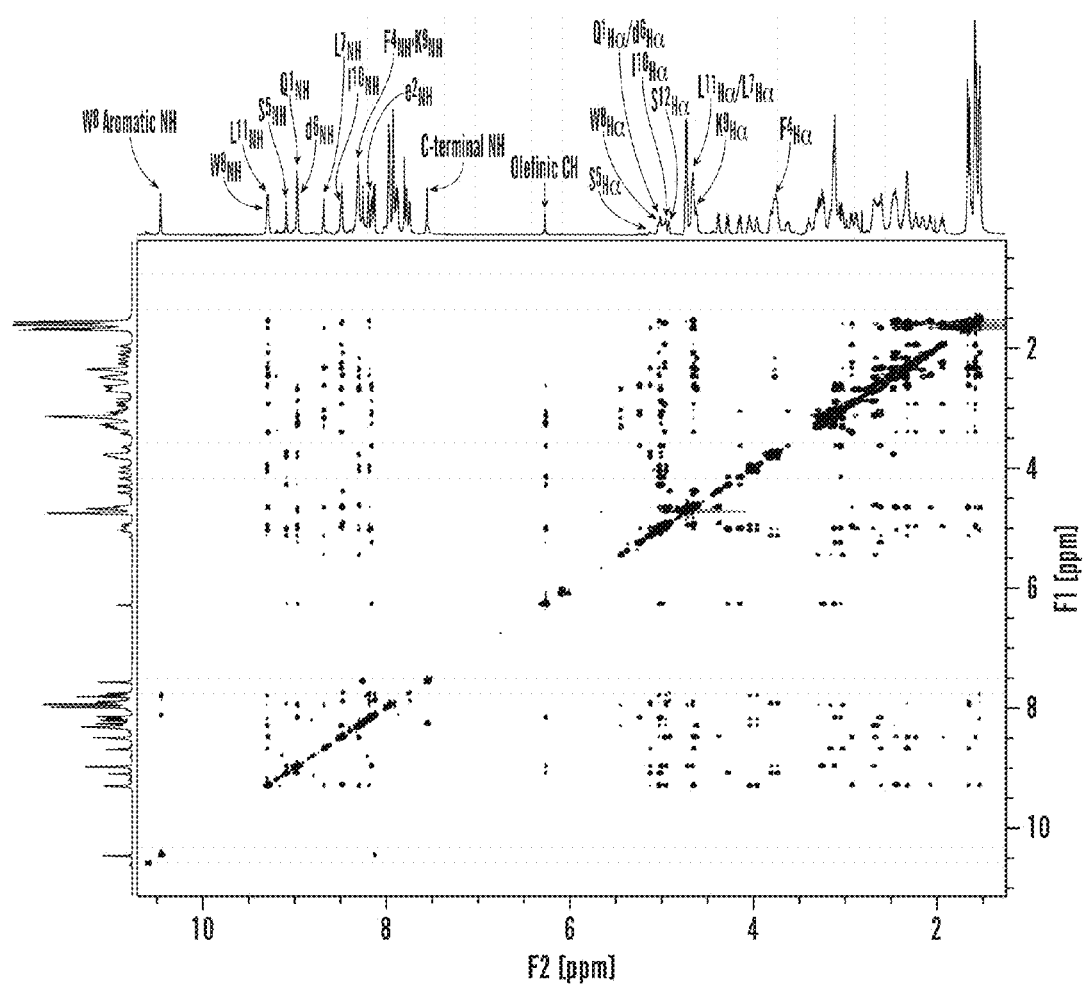
FIG. 11 is the NOESY spectrum (900 MHz, 293 K) of peptide 1 in 20% TFE-d3 in PBS. $\beta^3$-Amino acid residues are shown in lower-case blue letters.

CD spectra were recorded on AVIV 202SF CD spectrometer equipped with a temperature controller using 1 mm length cells and a scan speed of 0.5 nm/min. The spectra were averaged over 10 scans with the baseline subtracted from analogous conditions as that for the samples. The samples were prepared in 0.1× phosphate buffered saline (13.7 mM NaCl, 1 mM phosphate, 0.27 mM KCl, pH 7.4), containing 10% trifluoroethanol, with the final peptide concentration of 100 μM. The concentrations of peptides were determined by the UV absorption of tryptophan residue at 280 nm. The helix content of each α-peptide was determined from the mean residue CD at 222 nm, $[\theta]_{222}$ (deg cm$^2$ dmol$^{-1}$) corrected for the number of amino acids. Percent helicity was calculated from the ratio $[\theta]222/[\theta]max$, where $[\theta]max=(-44000+$ 250T)(1−k/n), with k=4.0 and n=number of residues (Wang et al., *J. Am. Chem. Soc'y* 128:9248-56 (2006), which is hereby incorporated by reference in its entirety). FIG. 5 shows the CD spectra of peptide 1, peptide 2, and linear an peptides 3 and 4. The CD spectra of peptide 5 and peptide 6 are shown in FIG. 6.

Example 5

Temperature Dependence of Amide Proton Chemical Shift

All experiments were carried out on a Bruker AVANCE 900 MHz spectrometer equipped with a cryoprobe and 3D gradient control. Samples were prepared by dissolving 2 mg of peptide in 450 μL of PBS buffer (137 mM NaCl, 10 mM phosphate, 2.7 mM KCl, pH 7.4) and 120 μL, of TFE-d3, The 1D proton spectra or 2D TOCSY spectra (when overlapping was severe) were employed to discern the chemical shifts of the amide protons. Solvent suppression was achieved with a 3919 Watergate pulse sequence. At each temperature, the sample was allowed to equilibrate for 15 minutes.

Example 6

2D NMR Spectroscopy

Spectra of peptide 1 (samples prepared as described above) were recorded on a Bruker AVANCE 900 at 20° C. All 2D spectra were recorded by collecting 4092 complex data points in the t2 domain by averaging 64 scans and 128 increments in the 11 domain with the States-TPPI mode. All TOCSY experiments were performed with a mixing time of 80 ms, and NOESY with the mixing time of 200 ms. The data were processed and analyzed using the Bruker TOPSPIN program. The original free induction decays (FIDs) were zero-filled to give a final matrix of 2048 by 2048 real data points. A 90° sine-square window function was applied in both dimensions.

The $^1$H NMR assignments and chemical shifts (δ, ppm) for peptide 1 (293 K) in 20% TFE-d3 in PBS are shown in Table 2. See FIGS. 7-11.

TABLE 2

$^1$H NMR assignments and chemical shifts for peptide 1.

| Residue[a] | NH | Hα | Hβ | Hγ | Hδ | Hε |
|---|---|---|---|---|---|---|
| Q1 | 8.983 | 5.012 | 3.118 | 2.881 | NA | NA |
| e2 | 8.176 | 5.249 | 3.623 | 3.107 3.053 | 2.612 | NA |
| G3 | NA | NA | NA | NA | NA | NA |
| F4 | 8.316 | 3.774 | 2.472 | NA | NA | NA |
| S5 | 9.102 | 5.130 | 3.817 3.742 | NA | NA | NA |
| d6 | 8.983 | 4.958 | 4.667 | 2.687 | NA | NA |
| L7 | 8.693 | 4.657 | 2.612 | 2.321 | — | NA |
| W8 | 9.317 | 5.033 | 4.043 3.957 | NA | NA | NA |
| K9 | 8.305 | 4.624 | 2.676 | 2.354 | 2.159 | — |
| I10 | 8.499 | 4.969 | 3.398 | 2.924 | 2.321 | 1.235 1.934 |
| L11 | 9.306 | 4.657 | 2.44 | 2.074 | — | NA |
| S12 | 8.488 | 4.915 | 4.657 4.377 | NA | NA | NA |

[a]Lower-case bold letters denote $\beta^3$-residues.

Example 7

Amide Hydrogen—Deuterium Exchange Experiment

Lyophilized samples of peptide 1 from the above experiments were dissolved in 600 μL of a D₂O/TFE-d3 mixture (80/20) to initiate the H/D exchange. The pH of the solution was confirmed. Spectra were recorded on a pre-shimmed Bruker AVANCE 900 MHz spectrometer. The recorded temperature was 20° C. both inside and outside the probe. The dead time was circa 2 minutes. The intensity changes for each amide proton were determined by monitoring either the HN peaks on 1D spectra or the cross-peaks between FIN and HR on 2D TOCSY spectra when overlapping was severe. The peak height data were fit into one phase exponential equation to get the exchange rate constants using GraphPa 1 Prism 4.0 program.

Example 8

His₆-Mdm2 Expression and Purification

Competent BL21 DE3 pLySS *E. coli* cells were transformed by heat shocking the bacteria at 42° C. for 1 minute in media containing a pET-14B vector containing a His6-tagged Mdm2 (25-117) fusion protein. Cells were grown on ampicillin-containing agar plates (50 mg/mL), and a single culture was used to inoculate a 100 mL overnight culture of LB media containing ampicillin (50 mg/mL). 500 mL of terrific broth (4 L flask) was seeded with 50 mL of overnight culture and incubated at 30° C. until the optical density of the media was 1 at 600 nm. Induction of protein expression with 0.4 mM IPTG (Novagen) was done by incubating the flask at 30° C. for an additional 4.5 hours. The cells were harvested by centrifugation at 6000 g for 20 minutes and the supernatant was discarded. The cells were resuspended in 10 mL binding buffer (50 mM NaH₂PO₄ (pH 8), 300 mM NaCl, 10 mM imidazole, 2 mM β-mercaptoethanol, and protease inhibitors (Roche)), and lysed by sonication in ice (15×7 seconds pulses). The cells were again centrifuged at 15,000 g for 20 minutes, and the resulting supernatant containing the desired Mdm2 fusion protein was incubated with Ni-NTA beads (Novagen) at 4° C. for 2 hours. Beads were washed five times with 10 ml washing buffer (50 mM NaH₂PO₄ (pH 8), 300 mM NaCl, 25 mM imidazole, 2 mM β-mercaptoethanol) and the protein was eluted with elution buffer (50 mM NaH₂PO₄, 300 mM NaCl, 250 mM imidazole, 2 mM β-mercaptoethanol, pH 8). The resulting protein was dialyzed in 10 mM PBS (pH 7.5) with 5 mM EDTA and 0.5 mM DTT and concentrated with 3 kD MW cut-off Amicon concentrator tubes (Millipore). Purified Mdm2 was characterized by SDS-PAGE analysis, snap-frozen in liquid N₂, and stored at −80° C. until further use.

Example 9

His₆-Mdm2 Binding Studies

The relative affinities of peptides for N-terminal His₆-tagged Mdm2 (25-117) were determined using fluorescence polarization-based competitive binding assay with fluorescein labeled p53 peptide (Flu-p53). The polarization experiments were performed with a DTX 880 Multimode Detector (Beckman) at 25° C., with excitation and emission wavelengths at 485 nm and 535 nm, respectively. All samples were prepared in 96 well plates in 0.1% pluronic F-68 (Sigma). The binding affinity ($K_D$) values reported for each peptide are the averages of 3 to 5 individual experiments, and were determined by fitting the experimental data to a sigmoidal dose-response nonlinear regression model on GraphPad Prism 4.0. The concentration of the Mdm2 protein was determined by a Bradford Assay (BioRad).

Figure 12:
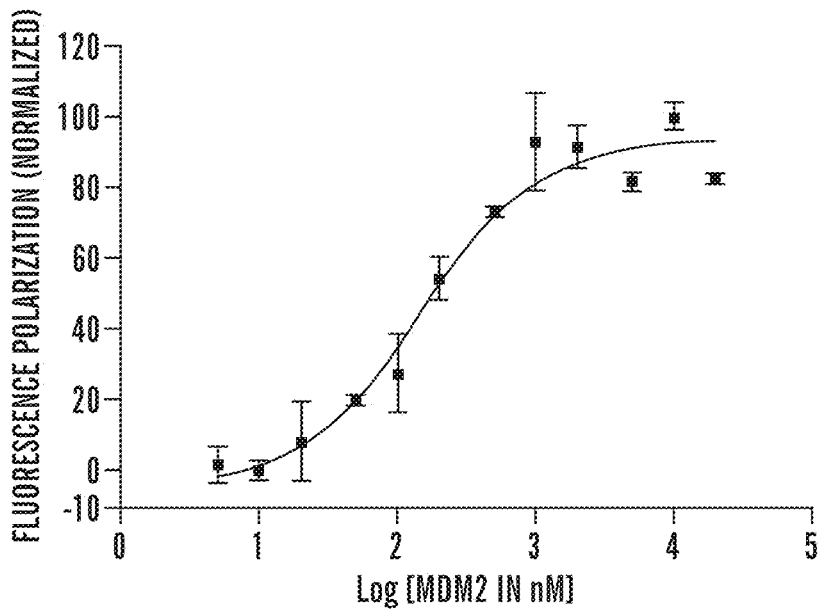
FIG. 12 is the saturation binding curve of Flu-p53 with Mdm2 in PBS buffer at 25° C. $K_D$=137±57 nM.

Prior to the competition experiments, the affinity of peptide Flu-p53 for Mdm2 (25-117) was determined by monitoring polarization of the fluorescent probe upon binding Mdm2 (25-117). Addition of an increasing concentration (0 nm to 50 μM) of Mdm2 (25-117) protein to a 15 nM solution of Flu-p53 in Mdm2 (25-117) dialysis buffer (10 mM PBS (pH 7.4), 5 mM EDTA, and 0.5 mM DTT) and 0.1% pluronic acid afforded the saturation-binding curve shown in FIG. 12. The $IC_{50}$ value obtained from this binding curve was fit into equation (1) to calculate the dissociation constant ($K_{D1}$) for the p53/Mdm2 complex (Roehrl et al., *Biochemistry* 43:16056-66 (2004), which is hereby incorporated by reference in its entirety). The $K_{D1}$ of peptide Flu-p53 was determined to be 137±57 nM.

$$K_{D1} = (R_T^*(1-F_{SB}) + L_{ST}^* F_{SB}^2)/F_{SB} - L_{ST} \tag{1}$$

where:
$R_T$=Total concentration of Mdm2 protein
$L_{ST}$=Total concentration of p53 fluorescent peptide
$F_{SB}$=Fraction of bound p53 fluorescent peptide For competition binding experiments, a solution of 300 nM Mdm2 and 15 nM Flu-p53 in Mdm2 dialysis buffer (1×PBS (pH 7.4), 5 mM EDTA, and 0.5 mM DTT) and 0.1% pluronic acid was incubated at 25° C. in a 96 well plate. After 1 hour appropriate concentrations of the HBS or linear peptides (1 nm to 100 μM) were added to the Mdm2-Flu-p53 solution and the resulting mixtures were incubated at 25° C. for 1 hour before measuring the degree of dissociation of Flu-p53 by polarization. The $IC_{50}$ was fit into equation (2) to calculate the $K_{D2}$ value of the HBS or linear peptides.

$$K_{D2} = K_{D1}^* F_{SB}^* ((L_T/L_{ST}^* F_{SB}^2 - (K_{D1}+L_{ST}+R_T)^* F_{SB} + R_T)) - 1/(1-F_{SD})) \tag{2}$$

where:
$K_{D1}$=$K_D$ of fluorescent probe Flu-p53
$R_T$=Total concentration of Mdm2 protein
$L_T$=Total concentration of HBS or linear peptide
$L_{ST}$=Total concentration of p53 fluorescent peptide
$F_{SB}$=Fraction of bound p53 fluorescent peptide The binding affinity ($K_D$) values reported for each peptide (Table 3) are the averages of 3-5 individual experiments, and were determined by fitting the experimental data to a sigmoidal dose-response nonlinear regression model on GraphPad Prism 4.0 (Roehrl et al., *Biochemistry* 43:16056 (2004), which is hereby incorporated by reference in its entirety).

TABLE 3

Affinity of p53 analogs for Mdm2.

| | Peptide Sequence[a] | Backbone | $K_D$ (nM)[b] |
|---|---|---|---|
| 1 | XQeG*FSdLWKILS-NH₂ (SEQ. ID NO: 5) | HBS α3/β | 80 ± 21 |
| 2 | XQEG*FSDLWKLLS-NH₂ (SEQ. ID NO: 6) | HBS α | 71 ± 16 |
| 3 | Ac-QeGFSdLWKILS-NH₂ (SEQ. ID NO: 7) | Unconstrained α3/β | 102 ± 39 |

TABLE 3-continued

Affinity of p53 analogs for Mdm2.

| | Peptide Sequence[a] | Backbone | $K_D$ (nM)[b] |
|---|---|---|---|
| 4 | Ac-Q(ACPC)GFS(ACPC)LWK(ACPC)LS-NH$_2$ (SEQ. ID NO: 8) | α3/cyclic β | 430 ± 86 |
| 5 | XQeG*ASdLWKIAS-NH$_2$ (SEQ. ID NO: 9) | HBS α3/β | >>1,000,000 |

[a]Lower-case bold letters denote β$^3$-residues; X is pentenoic acid; G* is N-allyl glycine; ACPC is cyclic β residue (1S,2S)-2-aminocyclopentane carboxylic acid.
[b]Binding constant for His$_6$-Mdm2

Example 10

Trypsin Digestion Assay

A solution containing 500 µM of tryptophan, 1 ng/µL of trypsin, and 500 µM of peptide in PBS was incubated at 4° C. At the indicated time intervals, 100 µL of this solution was quenched with 100 µL of 2% aqueous TFA, and then injected into reversed-phase HPLC to analyze the change in the area of the peptide peak compared to the area of an internal control (tryptophan).

Example 11

Serum Stability Assay

Peptides and 50% human serum (Sigma, St Louis, Mo., USA; product number S7023) in RPMI were temperature-equilibrated to 37° C. for 15 minutes prior to the experiments. 150 µl of peptides (500 µM) were added to 150 µl of 50% aqueous human serum (25% final serum concentration) at 37° C. for 0-24 hours. After 0, 2, 5, 10, and 24 hours, three samples of each peptide (50 µl) were taken, and were precipitated by the addition of 100 µl of 6% aqueous trichloroacetic acid. The samples were cooled to 4° C. for 20 minutes and centrifuged (14000 rpm for 5 minutes). The supernatants were immediately frozen on dry ice and 100 µl of each were analyzed on an Agilent LCMS using 0.1% formic acid in water (eluent A) and 0.1% formic acid in acetonitrile (eluent B). The level of intact peptide was determined by comparing the LC % area of the peptide peak at different time points to the % area of the 0-hour peak.

Example 12

Cellular Uptake Assays

HeLa cells were cultured to sub-confluence in DMEM (Invitrogen) supplemented with 10% (v/v) fetal bovine serum (FBS) at 37° C. in a humidified incubator containing 5% CO$_2$. Cells (~1×10$^4$ cells/ml) in DMEM supplemented with 10% FBS were plated onto a 24-well culture plate containing microscope cover slides. After overnight incubation, cells were washed three times with 1 ml HBSS (Invitrogen) and supplemented with 15 µM fluorescein-tagged peptides in 1 mM PBS (pH 7.4) to a total volume of 500 µl. Peptide treated cells were incubated for another 2 hours at 37° C., washed five times with 500 µl HBSS, and imaged directly on a Leica TSC SP 2 laser scanning confocal microscope. Twenty serial 1 µm Z-section images through the middle of the cells were collected and analyzed.

Results and Discussion of Examples 1-12

A new generation of HBS helices that resist proteolytic degradation have been developed by judicious incorporation of β$^3$-amino acid residues in an α-peptide. A 3:1 ratio of α:β residues was chosen such that every turn of the α-helix mimic features one β-residue. The key advantage of the HBS approach is its ability to provide conformational rigidity without utilizing side chain functionality. This study shows that the HBS method compares favorably with previous approaches in stabilizing oligomers composed of α- and β-residues (Home & Gellman, *Acc. Chem. Res.* 41:1399 (2008); Arvidsson et al., *Chem. Commun.* 649 (2001); Kritzer et al., *J. Am. Chem. Soc'y* 127:167 (2005); Hart et al., *J. Am. Chem. Soc'y* 125:4022 (2003); Cheng & DeGrado, *J. Am. Chem. Soc'y* 123:5162 (2001); Appella et al., *Nature* 387:381 (1997); Vaz et al., *ChemBioChem* 9:2254 (2008), each of which is hereby incorporated by reference in its entirety). The α3/β-HBS p53 helix mimetic (peptide 1) was found to target its cognate protein receptor with high affinity. Microscopy studies suggest that the constrained fluorescein conjugate can enter HeLa cells whereas the unconstrained derivative displays low cell permeability. Studies to evaluate the potential of this p53 mimetic to reactivate the p53 pathway are underway. Given the importance of α-helical domains in a plethora of protein—protein interactions (Bullock et al., *J. Am. Chem. Soc'y* 133:14220 (2011); Jochim & Arora, *ACS Chem. Biol.* 5:919 (2010); Jochim & Arora, *Mol. BioSyst.* 5:924 (2009), each of which is hereby incorporated by reference in its entirety), these proteolytically and conformationally stable, cell permeable molecules are expected to be attractive as reagents for biological studies and as leads for drug discovery.

Peptide Design

Design of chimeric HBS α/β helices was begun by examining suitable ratios of α to β residues such that the resulting compound would be a close mimic of a canonical α-helix. Modeling studies indicated that an α:β ratio of 3:1 would offer a close match, while a 2:1 ratio would lead to a slightly larger helical pitch than that observed with α-helices (FIG. 2A). An α:β ratio of 4:1 was not tested, because it was thought that insertion of at least one β-residue per helical turn would afford the highest protection against proteases. The ratio of 3:1 for α/β chimeric helices is consistent with those used by Gellman et al. for α-helix mimicry (Home et al., *Proc. Nat'l Acad. Sci. USA* 106:14751 (2009); Home et al., *Proc. Nat'l Acad. Sci. USA* 105:9151 (2008), each of which is hereby incorporated by reference in its entirety).

An HBS α3/β sequence (peptide 1) that mimics the p53 activation domain was designed (Table 4). Interaction of the p53 activation helix with Mdm2 is critical for the regulation of apoptosis (Joerger & Fersht, *Annu. Rev. Biochem.* 77:557 (2008), which is hereby incorporated by reference in its entirety). This complex has been targeted with several different types of synthetic inhibitors (Lee et al., *J. Am. Chem. Soc'y* 133:676 (2011); Murray & Gellman, *Biopolymers* 88:657 (2007); Gemperli et al., *J. Am. Chem. Soc'y* 127:1596 (2005); Bernal et al., *J. Am. Chem. Soc'y* 129:2456 (2007); Shangary & Wang, *Clin. Cancer Res.* 14:5318 (2008); Campbell et al., *Org. Biomol. Chem.* 8:2344 (2010); Yin et al., *Angew. Chem. Int'l Ed.* 44:2704 (2005); Bernal et al., *Cancer Cell* 18:411 (2010), each of which is hereby incorporated by reference in its entirety), making it a model protein—protein interaction for inhibitor design. Protein binding properties of an HBS α-helix mimic of the p53 sequence (peptide 2) has previously been reported (Henchey et al., *ChemBioChem* 11:2104 (2010), which is hereby incorporated by reference in its entirety). Comparison of peptides 1 (α3/β-HBS) and 2 (α-HBS) in binding assays provides direct assessment of the α/β helix design. Two unconstrained α3/β-peptide analogs (peptides 3 and 4) were also designed to evaluate the effect of the HBS constraint. Peptide 4 contains cyclic β-residues (trans-2-aminocyclopentanecarboxylic acid (ACPC) residues) in place of acyclic β-residues in peptide 3. ACPC residues have been previously shown to stabilize helical conformations in β- and α/β-peptides (Home & Gellman, *Acc. Chem. Res.* 41:1399 (2008); Appella et al., *Nature* 387:381 (1997), each of which is hereby incorporated by reference in its entirety).

TABLE 4

Design of α- and α3/β-peptides.

| Peptide | Sequence[a] | Backbone |
|---|---|---|
| 1 | XQeG*FSdLWKILS-NH$_2$ (SEQ ID NO: 5) | α3/β |
| 2 | XQEG*FSDLWKLLS-NH$_2$ (SEQ ID NO: 6) | α |
| 3 | AcQeGFSdLWKILS-NH$_2$ (SEQ ID NO: 7) | α3/β |
| 4 | AcQ(ACPC)GFS(ACPC)LWK(ACPC)LS-NH$_2$ (SEQ ID NO: 8) | α3/β$^{cyclo}$ |

[a]Lower-case bold letters denote β$^3$-residues; X is pentenoic acid; G* is N-allyl glycine; ACPC is cyclic β residue (1S,2S)-2-aminocyclopentane carboxylic acid.

Synthesis

HBS helices contain a carbon—carbon bond in place of a main chain i→i+4 hydrogen bond. The hydrocarbon bridge is inserted using a ring-closing metathesis reaction between two appropriately-placed alkene groups (FIG. 1) (Grubbs, *Angew. Chem. Int'l Ed.* 45:3760 (2006), which is hereby incorporated by reference in its entirety). Detailed protocols for the synthesis of FIBS helices have been reported previously (U.S. Pat. No. 7,202,332 to Arora & Chapman; Chapman & Arora, *Org. Lett.* 8:5825 (2006); Dimartino et al., *Org. Lett.* 7:2389 (2005); Patgiri et al., *Nat. Protoc.* 5:1857 (2010); Patgiri et al., *Org. Biomol. Chem.* 8:1773 (2010), each of which is hereby incorporated by reference in its entirety).

Structural Characterization by Circular Dichroism

The helicities of the peptides were examined by circular dichroism spectroscopy. CD studies were performed in 10% trifluoroethanol (TFE) in phosphate buffered saline (PBS) to obtain a measure of their helical content. As shown in FIG. 5, Peptide 2 affords a CD signature typical of a canonical α-helix, with double minima near 206 and 222 nm and a maximum at 190 nm (Henchey et al., *ChemBioChem* 11:2104 (2010), which is hereby incorporated by reference in its entirety). The trace obtained for peptide 1 is similar to those observed for α-helices, except with a weaker 222 nm band. The unconstrained peptide 3 provides a weaker signal as compared to peptide 1, highlighting the conformational rigidity endowed by the HBS constraint. The CD spectrum of peptide 4 is consistent with the previously reported spectrum of β- and chimeric α/β-peptides (Sawada & Gellman, *J. Am. Chem. Soc'y* 133:7336 (2011); Price et al., *J. Am. Chem. Soc'y* 132:12378 (2010), each of which is hereby incorporated by reference in its entirety). Comparison of CD spectra of peptides 1 and 4 suggests that these molecules are potentially adopting different conformations in solution.

Thermal Stability of HBS 1

Figure 13:
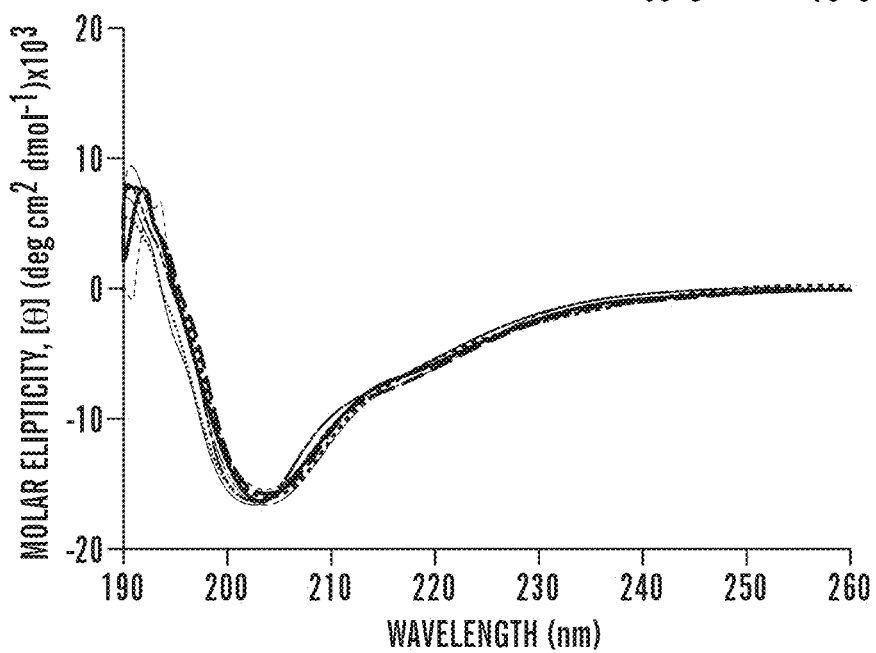
FIG. 13 is the circular dichroism spectra of peptide 1 showing the effect of temperature on the stability of peptide 1. The CD spectra were obtained in 10% TFE/PBS.

The thermal stability of peptide 1 was next investigated by monitoring the temperature-dependent change in its CD spectrum (FIG. 13). This study highlights the conformational stability of peptide 1, as a negligible difference was observed between spectra obtained at different temperatures (Wang et al., *Org. Biomolec. Chem.* 4:4074 (2006), which is hereby incorporated by reference in its entirety).

Structural Characterization by NMR

A combination of 1D and 2D NMR experiments were utilized to further establish the conformation of peptide 1. NMR studies were performed in 20% d$_3$-TFE in PBS (pH 3.5) on a Bruker 900 MHz spectrometer. Key medium- and long-range NOEs, supporting a helical conformation, were observed. Analysis of this data suggests existence of a single major helical conformation in peptide 1 (Schmitt et al., *J. Am. Chem. Soc'y* 128:4538 (2006); Hayen et al., *Angew. Chem. Int'l Ed. Engl.* 43:505 (2004), each of which is hereby incorporated by reference in its entirety).

To evaluate the conformational stability and dynamics of peptide 1, amide proton temperature coefficients and rates of amide proton H/D exchange were obtained. A combination of these experiments provides a convincing measure of the extent to which a particular main-chain proton is involved in intramolecular hydrogen bonding. Together the NMR studies provide persuasive evidence of a stable helical conformation in this constrained oligomer.

2D NMR Spectroscopy

Figure 14A:
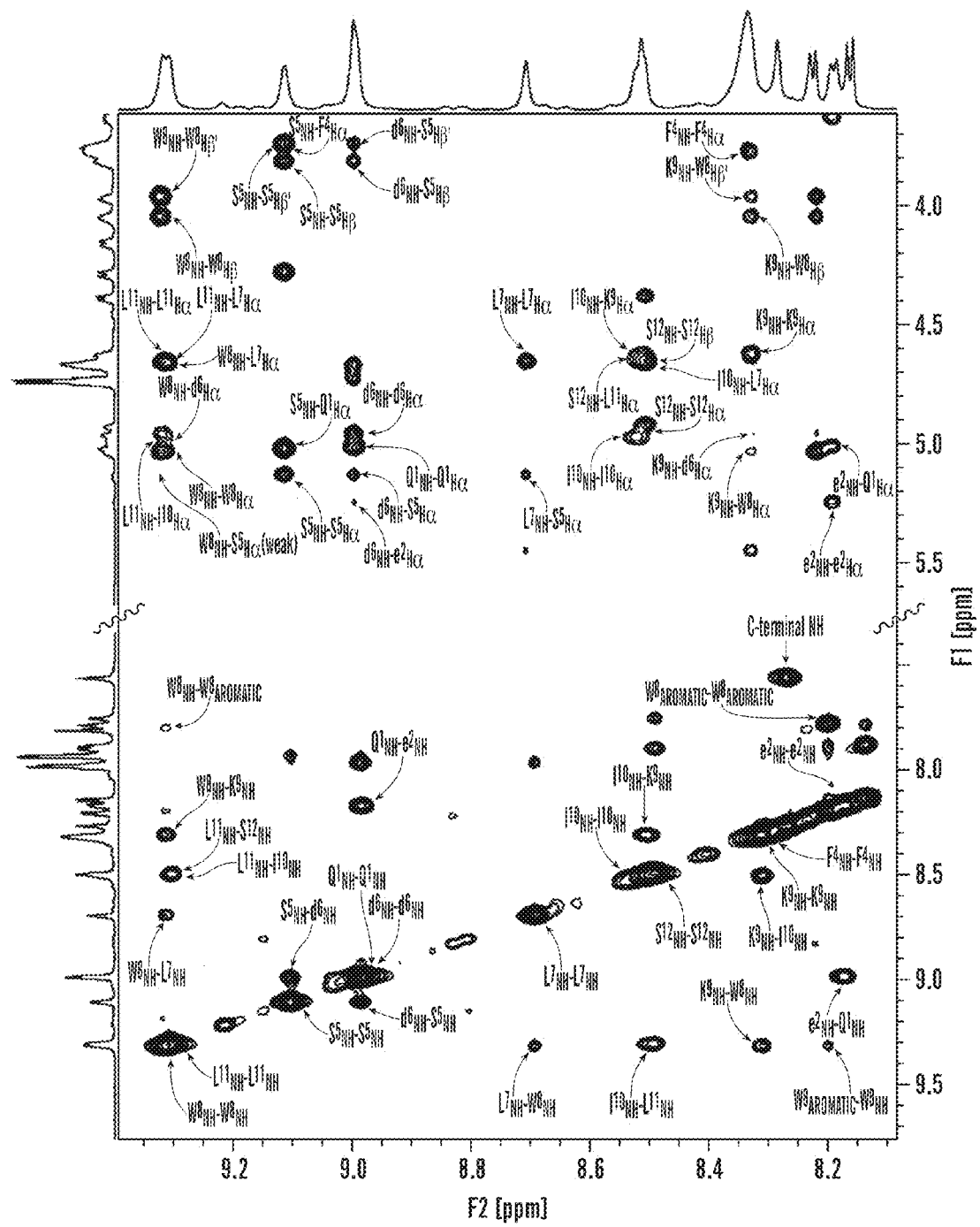
FIGS. 14A-B are the cross-section of NOESY spectra (FIG. 14A) and the NOESY correlation chart (FIG. 14B) for peptide 1. The NMR spectra were obtained in 20% TFE/PBS. Lower case letters denote $\beta^3$-residues.
Figure 14B:
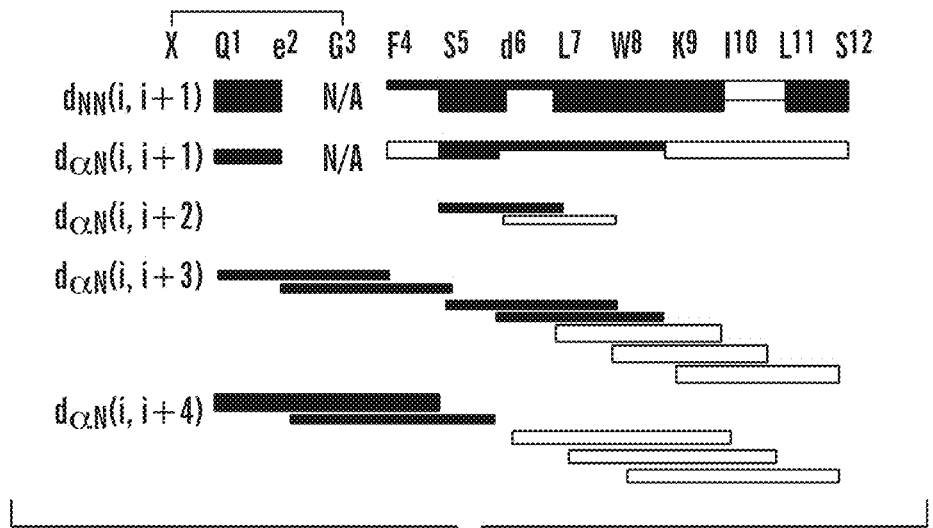

A set of 2D TOCSY, DQF-COSY, and NOESY spectroscopies were used to assign $^1$H NMR resonances for peptide 1. As shown in FIG. 14A, Sequential NH—NH (i and i+1) NOESY cross-peaks, a signature of helical structure, were observed for peptide 1, as shown in the NOE correlation chart (FIG. 14B). The NOESY spectrum further reveals several medium to weak (i, i+3) and (i, i+4) NH—CHa cross peaks that support an α-helix-like conformation in peptide 1.

Amide Proton Temperature Coefficients

Figure 15A:
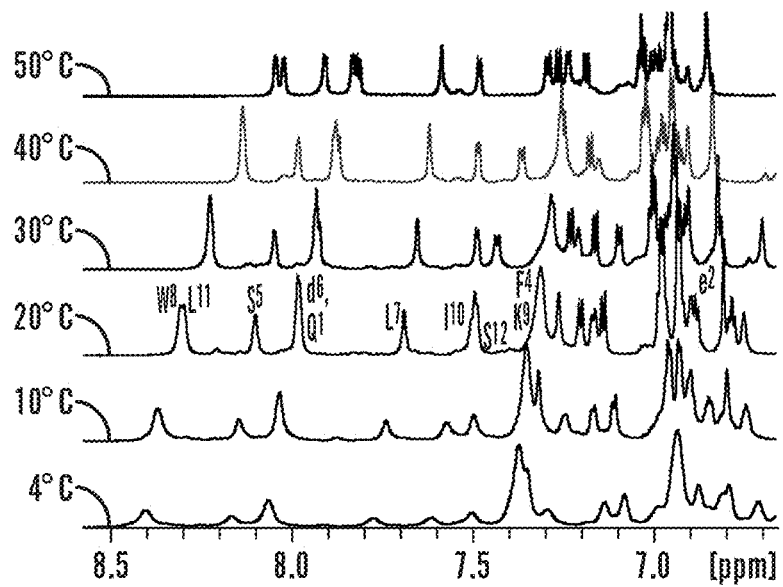
FIGS. 15A-B are spectra (FIG. 15A) and plots (FIG. 15B) showing the temperature dependence of backbone amide proton chemical shifts in peptide 1. The NMR spectra were obtained in 20% TFE/PBS. Lower case letters denote $\beta^3$-residues.
Figure 15B:
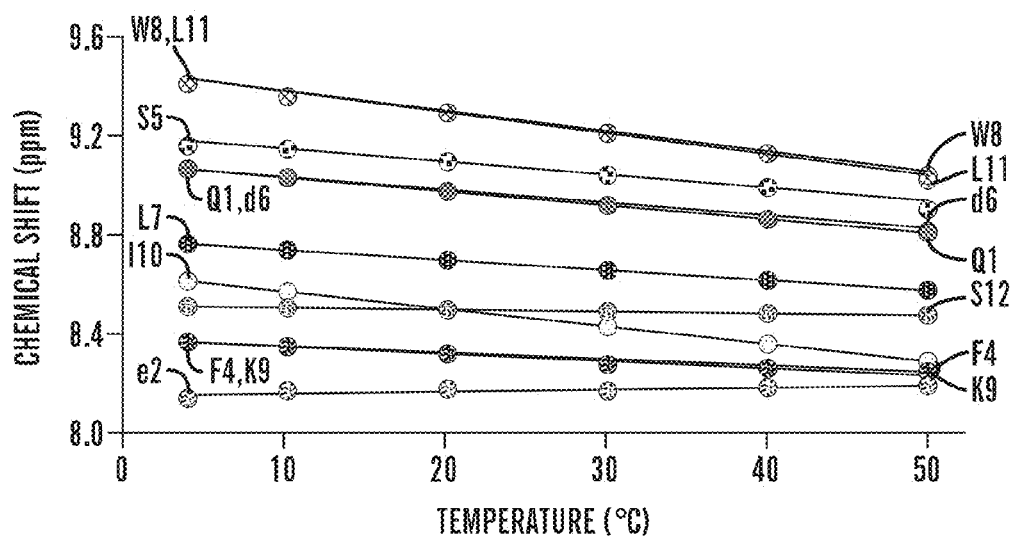

The amide protons show temperature-dependent shifts of resonances, which is a measure of the extent to which a particular amide proton is hydrogen-bonded. Any amide proton that exchanges slowly with a temperature coefficient more positive than −4.5 ppb/K is considered to be strongly hydrogen-bonded, although variations in helical curvature complicate analysis (Baxter & Williamson, *J. Biomol. NMR* 9:359 (1997); Cierpicki & Otlewski, *J. Biomol. NMR* 21:249 (2001), each of which is hereby incorporated by reference in its entirety). FIGS. 15A-B show the temperature-dependent chemical shifts for main-chain amide protons in peptide 1. Table 5 lists the temperature coefficients for peptide 1. For most NHs these temperature coefficients are in the range that is considered to be indicative of hydrogen-bonded amide protons. The major exception is e2, which resides within the macrocycle at the N-terminus of the helix and is not expected to participate in intramolecular hydrogen bonding.

TABLE 5

Summary of amide proton temperature coefficients and deuterium exchange data for peptide 1.

| | Residues[a] | | | | | | | | | | |
|---|---|---|---|---|---|---|---|---|---|---|---|
| | Q1 | e2 | F4 | S5 | d6 | L7 | W8 | K9 | I10 | L11 | S12 |
| Temp. coefficient (ppb/ΔK) | −5.4 | 0.8 | −2.9 | −5.5 | −5.0 | −4.0 | −7.8 | −3.1 | −6.9 | −8.1 | −0.4 |
| H/D rate constant × $10^{-5}$ ($s^{-1}$) | 14.0 | 16.6 | 1.1 | 27.6 | 14.0 | 1.7 | 4.1 | 1.1 | 2.5 | 7.5 | 8.8 |
| Protection factor (log $k_{ch}/k_{ex}$) | 1.0 | 1.45 | 2.16 | 1.26 | 2.01 | 1.96 | 1.06 | 2.07 | 1.42 | −0.3 | 1.81 |
| Stabilization, −ΔG (kcal/mol) | 1.28 | 1.93 | 2.89 | 1.66 | 2.69 | 2.62 | 1.37 | 2.77 | 1.88 | — | 2.42 |

[a]Lower-case bold letters denote $β^3$-residues;
X is pentenoic acid;
G* is N-allyl glycine;
ACPC is cyclic β residue (1S,2S)-2-aminocyclopentane carboxylic acid.

Amide H/D Exchange Rates

Figure 16A:
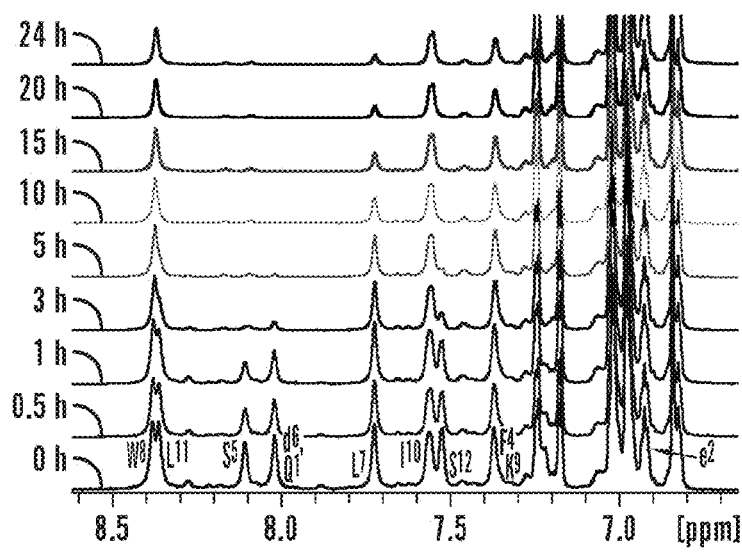
FIGS. 16A-B are hydrogen—deuterium exchange spectra (FIG. 16A) and plots (FIG. 16B) for backbone amide protons in peptide 1. The NMR spectra were obtained in 20% TFE/PBS. Lower case letters denote $\beta^3$-residues.
Figure 16B:
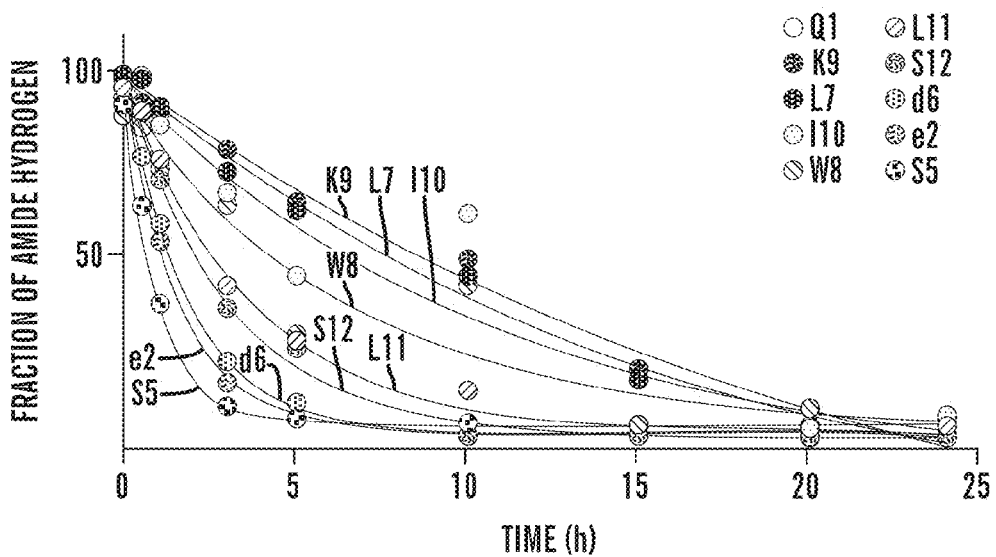

Main-chain amide hydrogen—deuterium exchange rates offer a sensitive measure of the structural stability and dynamics of proteins (Connelly et al., Proteins 17:87 (1993); Bai et al., Proteins 17:75 (1993); Englander & Kallenbach, Quart. Rev. Biophys. 16:521 (1983), each of which is hereby incorporated by reference in its entirety). Structured protein amide protons are involved in backbone hydrogen bonding and are shielded from solvents resulting in their slow H/D exchange kinetics compared to unstructured protein amide protons. FIGS. 16A-B show the rates of H/D exchange for peptide 1; the tabulated exchange values are shown in Table 5 supra. The individual hydrogen—deuterium exchange rates in this helix can be determined precisely, which is typically not possible for short peptides, indicating the conformational stability of this oligomer. The measured exchange rates, $k_{ex}$, were compared to the predicted intrinsic chemical exchange rate, $k_{ch}$, for an unstructured α-peptide of the same sequence, to assess individual protection factors (log $k_{ch}/k_{ex}$) and the corresponding free energies of protection (−ΔG) (Bai et al., Methods Enzymol. 259:344 (1995), which is hereby incorporated by reference in its entirety). The predicted intrinsic chemical exchange rates, protection factors, and the free energy of protection were calculated using the spreadsheet at http://hx2.med.upenn.edu, and are also shown in Table 5 supra. (This worksheet was developed for α-peptides and not for heterogeneous sequences; however, its use is thought to offer critical insights.) The data indicate that peptide 1 contains a highly stable hydrogen-bonded network with significant protection factors and associated free energies of protection (1.3-2.9 kcal/mol). Such a degree of stabilization is typically observed for buried amide protons in proteins but not in short peptides (Wang et al., J. Am. Chem. Soc'y 128: 9248-56 (2006); Zhou et al., J. Am. Chem. Soc'y 116:6482 (1994), each of which is hereby incorporated by reference in its entirety).

Potential to Target Protein Receptors that Recognize α-Helices

Figure 17:
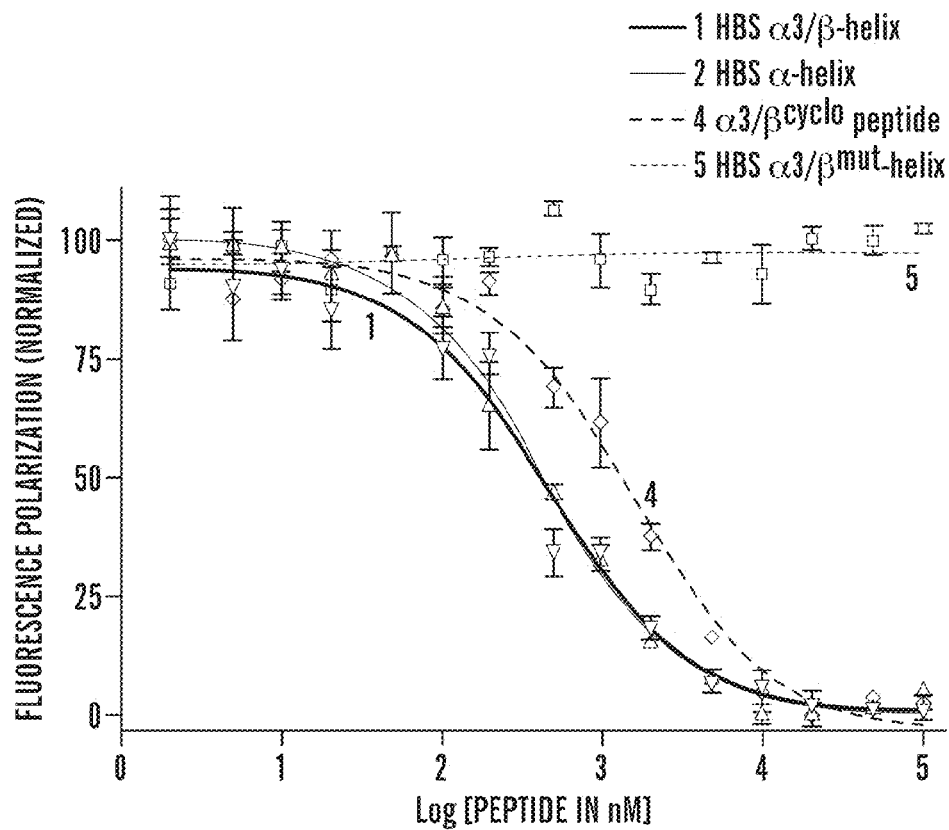
FIG. 17 is a graph of peptide binding to His$_6$-tagged Mdm2 determined by a fluorescence-polarization assay.

The circular dichroism and NMR studies provide compelling evidence that peptide 1 adopts a configuration similar to that of an α-helix. To evaluate the potential of HBS α3/β helices to target proteins that recognize α-helices, the affinity of peptides 1, 2, and 4 for Mdm2 were measured. Fluorescence polarization-based competition binding experiments were performed and it was found that peptide 1 binds to Mdm2 with high affinity ($K_D$=80±21 nM) comparable to that previously reported for the optimized HBS p53 α-helix analog peptide 2 (FIG. 17 and Table 3 supra) (Henchey et al., ChemBioChem 11:2104 (2010), which is hereby incorporated by reference in its entirety). This result unequivocally demonstrates that substitution of α-residues with β-residues in HBS helices does not introduce structural perturbations that compromise their binding affinities. To evaluate the specificity of peptide 1 for Mdm2, a negative control (peptide 5 (XQeG*ASdLWK1AS—NH$_2$)) was designed by mutating Phe 19 and Leu 26 (two of the residues in peptide 1 important for binding) to alanines. As shown in FIG. 17, as expected, peptide 5 does not bind to Mdm2 with measurable affinity. Peptide 4 binds Mdm2 with roughly five-fold lower affinity ($K_D$=430±86 nM) as compared to peptide 1.

Proteolytic Stability of HBS α3/β Helices

To assess whether incorporation of β-amino acid residues in peptide 1 enhances its proteolytic stability, the rates of its degradation in the presence of trypsin and serum were measured and compared to that of peptides 2, 3, and 6. Both of these experiments provide unambiguous evidence that α3/β peptides are resistant to both hydrolytic and serum proteases.

Figure 18A:
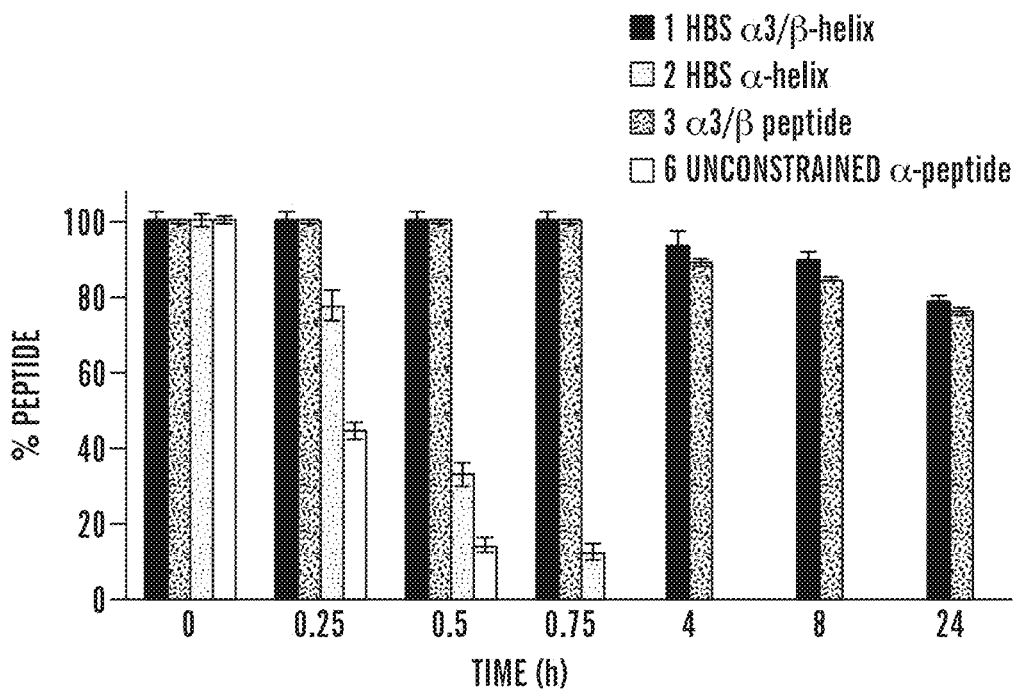
FIGS. 18A-B are graphs of the proteolytic degradation of $\alpha$-peptides 2 and 6 and $\alpha/\beta$-peptides 1 and 3 in the presence of trypsin (FIG. 18A) and serum (FIG. 18B). Initial rates for proteolytic digestion were measured using LCMS assays.

Trypsin was chosen as the model proteolytic enzyme because the p53 activation domain contains a lysine group near the C-terminus, providing a cleavage site for this enzyme. Importantly, the lysine residue is more than one helical turn away from the HBS constraints in peptides 1 and 2, allowing evaluation of their proteolytic stability without potential interference from the macrocycle. The rate of peptide digestion was measured using an LCMS assay with tryptophan as an internal control. It was found that roughly 20% of peptide 1 is cleaved after 24 hours (FIG. 18A). In contrast, peptide 2 was completely degraded in 1 hour, indicating that incorporation of β-residues in HBS peptides significantly improves their proteolytic stability. The linear α3/β peptide 3 is also stable toward degradation, in keeping with the previously reported observations (Hook et al., Chem. Biodivers. 2:591 (2005); Seebach & Gardiner, Acc. Chem. Res. 41:1366 (2008); Home & Gellman, Acc. Chem. Res. 41:1399 (2008); Sadowsky et al., ChemBioChem 8:903 (2007), each of which is hereby incorporated by reference in its entirety).

Figure 18B:
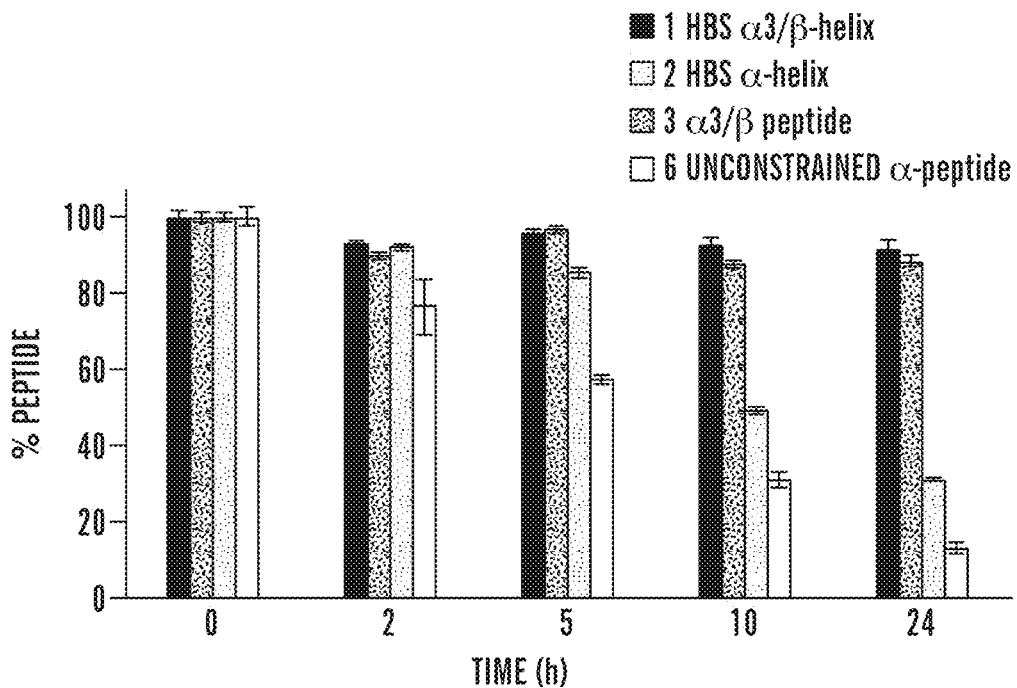

The trypsin digestion assay gives compelling evidence that α3/β-peptides are stable towards digestive proteases. The stability of these peptides was further evaluated in the presence of serum proteases (FIG. 18B). Human serum contains a myriad of proteases and provides a gauge for the stability of compounds under physiological conditions. Peptides were incubated in 25% human serum in RPMI medium at 37° C. and monitored by LCMS. A majority of peptide 2 was degraded under the assay conditions after 24 hours, while peptide 1 remained unperturbed, corroborating the results from the trypsin digestion assay.

Cellular Uptake

Figure 19:
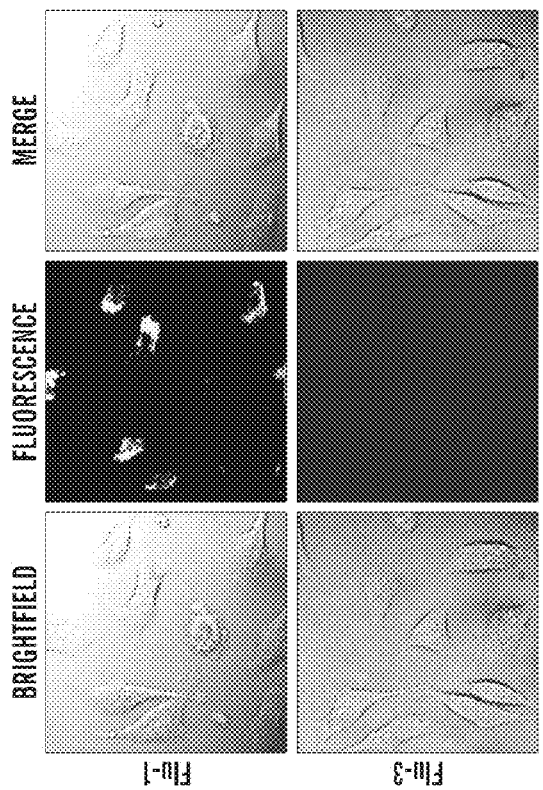
FIG. 19 is a series of images showing the cellular uptake of fluorescein-labeled $\alpha 3/\beta$-HBS peptide 1 (Flu-1) and unconstrained peptide 3 (Flu-3) into live HeLa cells visualized by confocal microscopy after a 2-hour incubation with the indicated peptide.

A noteworthy feature of stabilized helices is their ability to enter cells and modulate intracellular protein—protein interactions (Moellering et al., *Nature* 462:182 (2009); (Patgiri et al., *Nat. Chem. Biol.* 7:585 (2011); Henchey et al., *J. Am. Chem. Soc'y* 132:941 (2010); Bernal et al., *J. Am. Chem. Soc'y* 129:2456 (2007); Bernal et al., *Cancer Cell* 18:411 (2010); Walensky et al., *Science* 305:1466 (2004), each of which is hereby incorporated by reference in its entirety). To test whether the HBS constraint can permeabilize α3/β-peptides, HeLa cells were incubated with fluorescently labeled analogs of α3/β-peptides 1 and 3 (Flu-1 and Flu-3, respectively) for 2 hours and live cells were imaged with a confocal microscope. As shown in FIG. 19, Flu-1 showed intense intracellular fluorescence, as compared to the unconstrained analog Flu-3. The mechanism by which HBS peptides are internalized into the cells is currently under investigation, although previous studies have suggested an energy-dependent uptake mechanism for the constrained peptides (Patgiri et al., *Nat. Chem. Biol.* 7:585 (2011); Walensky et al., *Science* 305:1466 (2004), each of which is hereby incorporated by reference in its entirety). It is likely that cellular uptake of HBS helices will have sequence dependence; however, it is noteworthy that peptides with an overall negative charge are internalized (Patgiri et al., *Nat. Chem. Biol.* 7:585 (2011), which is hereby incorporated by reference in its entirety), as positive charge is often associated with enhanced cellular uptake of peptides (Henchey et al., *J. Am. Chem. Soc'y* 132: 941 (2010); Bernal et al., *J. Am. Chem. Soc'y* 129:2456 (2007); Wender et al., *Proc. Nat'l Acad. Sci. USA* 97:13003 (2000), each of which is hereby incorporated by reference in its entirety).

Example 13

General

Commercial-grade reagents and solvents were used without further purification except as indicated. Dichloroethane was distilled before use in the metathesis reactions. All reactions were stirred magnetically or mechanically shaken; moisture-sensitive reactions were performed under nitrogen or argon atmosphere. Reverse-phase HPLC experiments were conducted with 0.1% aqueous trifluoroacetic acid and 0.1% trifluoroacetic acid in acetonitrile buffers as eluents on $C_{18}$ reversed-phase columns using a Beckman Coulter HPLC equipped with a System Gold 168 Diode array detector. ESIMS data was obtained on an Agilent 1100 series LC/MSD (XCT) electrospray trap. The microwave reactions were performed in the CEM Discover single-mode reactor with controlled power, temperature, and time settings. Proton NMR spectra of HBS peptides were recorded on a Bruker AVANCE 900 MHz spectrometer.

Example 14

Synthesis of HBS Helices with β-Amino Acid(s) in the Attached Peptide

Peptides 4-7 (see FIG. 20) and 4-9 were synthesized as shown in Scheme 2 and described in U.S. Pat. No. 7,202,332 to Arora & Chapman; Chapman & Arora, *Org. Lett.* 8:5825-28 (2006); Dimartino et al., *Org. Lett.* 7:2389-92 (2005); Patgiri et al., *Nat. Protoc.* 5:1857-65 (2010); and Patgiri et al., *Org. Biomol. Chem.* 8:1773-76 (2010), each of which is hereby incorporated by reference in its entirety.

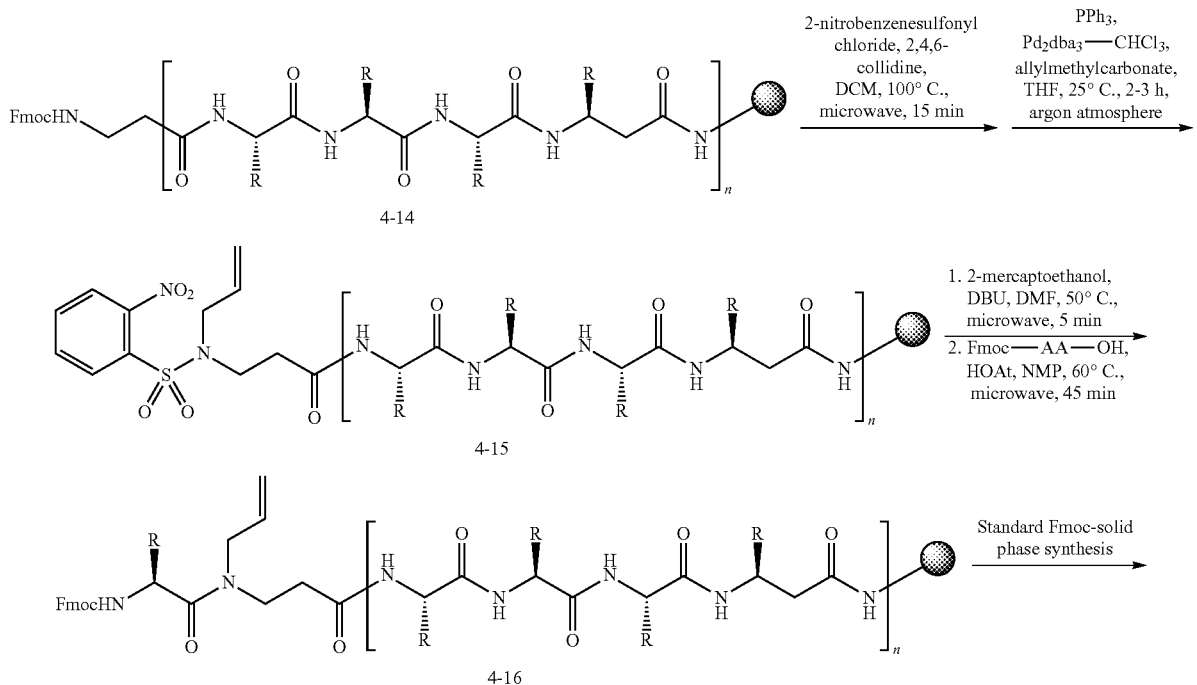

-continued

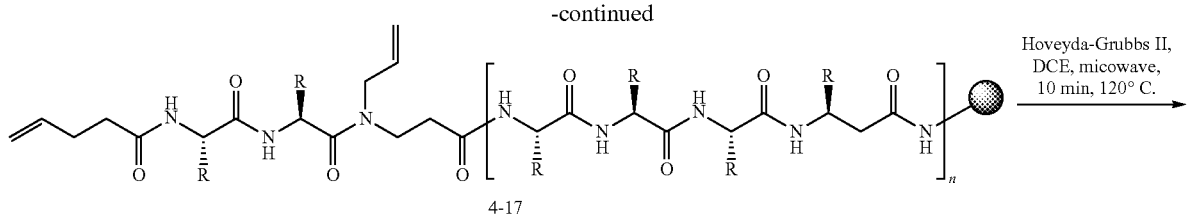

4-17

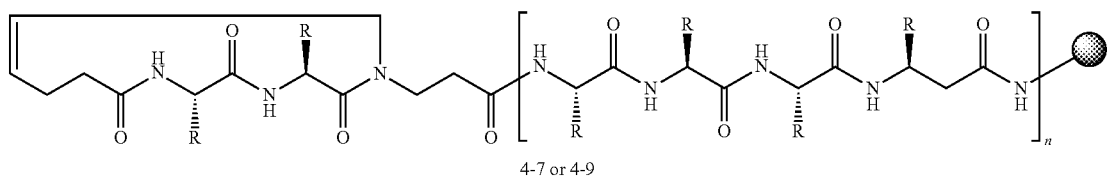

4-7 or 4-9

Briefly, peptide sequences up to the i+4$^{th}$ residue of the putative helix (4-14 in Scheme 2) were synthesized on solid phase on a CEM Liberty Series microwave peptide synthesizer. A solution of 2-nitrobenzenesulfonylchloride (3 eq) in DCM and 2,4,6-collidine (5 eq) were added to the pre-swelled resin, and the mixture was irradiated under microwaves (CEM discover) for 15 minutes at 100° C. The resin was then washed with DMF (×3) and DCM (×3), and dried under vacuum. Next, triphenylphosphine (0.8 eq) was added to the resin and flushed with argon for 30 minutes. Anhydrous THF was then added to the resin and the resin was swelled for 2 minutes before adding Pd$_2$ dba$_3$-CHCl$_3$ (0.1 eq) and allylmethylcarbonate (15 eq). The resulting reaction mixture was shaken for 2-3 hours at room temperature under argon atmosphere to yield 4-15.

To produce 4-16, resin containing 4-15 was washed with DCM (×3), DMF (×3), 0.02 M Sodiumdiethyldithiocarbamate/NMP (×3), DMF (×3), DCM (×3), and dried under vacuum. DBU (5 eq) and 2-mercaptoethanol (10 eq) were added to pre-swelled resin-bound 4-15 in DMF under nitrogen atmosphere. The reaction mixture was then subjected to microwave irradiation at 50° C. for 5 minutes. Resin (containing 4-15) was washed with DMF (×3) and DCM (×3), dried under vacuum, and treated with the desired Fmoc amino acid (20 eq), DIC (20 eq), and HOAt (10 eq) in NMP under microwave irradiation for 45 minutes at 60° C.

To produce 4-17, resin containing 4-16 was washed with DMF (×3), DCM (×3), and DMF (×3), and the Fmoc group was removed with 20% piperidine in NMP. The desired Fmoc amino acid residue (5 eq) and 4-pentenoic acid (5 eq) were then coupled to resin containing 4-16 using standard peptide synthesis methodology using HBTU (4.95 eq) and DIEA (10 eq) in NMP.

Ring-closing metathesis on bis-olefin 4-17 was performed with Hoveyda-Grubbs II catalyst (20 mol %) in dichloroethane under microwave irradiation at 120° C. for 10 minutes as described in U.S. Pat. No. 7,202,332 to Arora & Chapman; Chapman & Arora, *Org. Lett.* 8:5825-28 (2006); Dimartino et al., *Org. Lett.* 7:2389-92 (2005); Patgiri et al., *Nat. Protoc.* 5:1857-65 (2010); and Patgiri et al., *Org. Biomol. Chem.* 8:1773-76 (2010), each of which is hereby incorporated by reference in its entirety. Metathesized peptides were cleaved from the resin using TFA:TIS:water (95:2.5:2.5).

Linear peptides were prepared as described in Coin et al., *Nat. Protocols* 2:3247-56 (2007), and F$_{MOC}$ S$_{OLID}$ P$_{HASE}$ P$_{EP-}$ TIDE S$_{YNTHESIS}$: A P$_{RACTICAL}$ A$_{PPROACH}$ (W. C. Chan & P. D. White eds., 2000), each of which is hereby incorporated by reference in its entirety.

Figure 21:
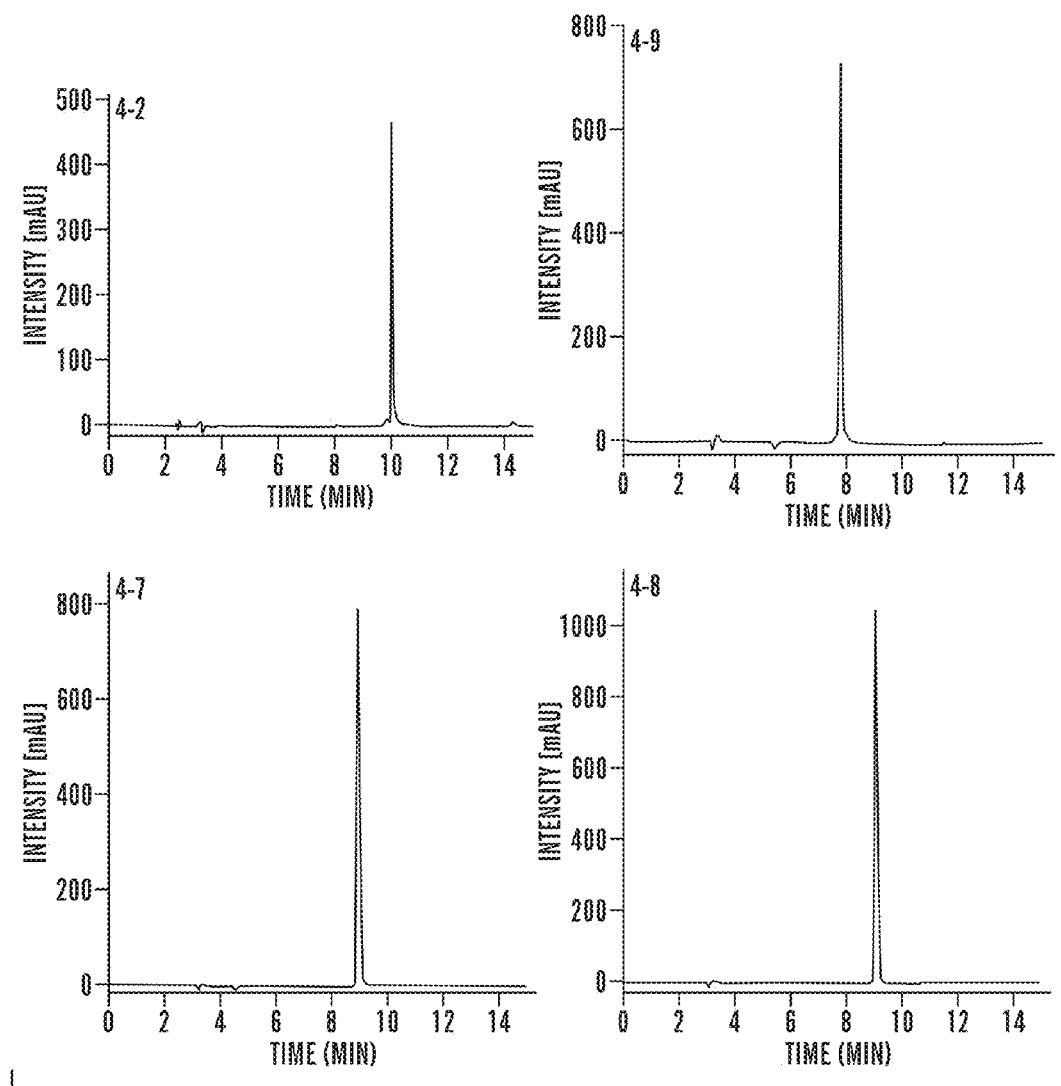
FIG. 21 shows analytical HPLC traces for peptides 4-7 and 4-9.

All peptides were purified by reversed-phase HPLC (C$_{18}$ column) (FIG. 21) and characterized by ESI-MS (Table 6).

TABLE 6

Mass spectroscopic characterization of peptides 4-2, 4-7, 4-8, 4-9, and Flu-p53.

| Peptide | Sequence$^a$ | Calculated [M+H]+ | Observed [M+H]+ |
|---|---|---|---|
| 4-2 | XQEG*FSDLWKLLS-NH$_2$ (SEQ ID NO: 6) | 1514.7 | 1515.0 |
| 4-7 | XQEg\*FSDIWKLIS-NH$_2$ (SEQ ID NO: 14) | 1557.7 | 1558.6 |
| 4-8 | AcQEg\*FSDIWKLIS-NH$_2$ (SEQ ID NO: 15) | 1505.7 | 1506.4 |
| 4-9 | XQEg\*ASDIWKLaS-NH$_2$ (SEQ ID NO: 16) | 1439.6 | 1440.1 |
| Flu-p53 | Ac-EAFSDLWKLLPENNVC$^{Flu}$-NH$_2$ (SEQ ID NO: 13) | 2305.0 | 1153.0* |

$^a$Lower-case bold letters denote β$^3$-residues; X is pentenoic acid; G* is N-allyl glycine; Flu is 5-acetamidofluorescein.
*(M+2)$^{2+}$ Example 15

Synthesis of 5-Carboxyfluorescein Labeled Peptides

5-Carboxyfluorscein labeled peptides were prepared as described in Example 3 supra.

Example 16

Circular Dichroism Spectroscopy

Figure 22:
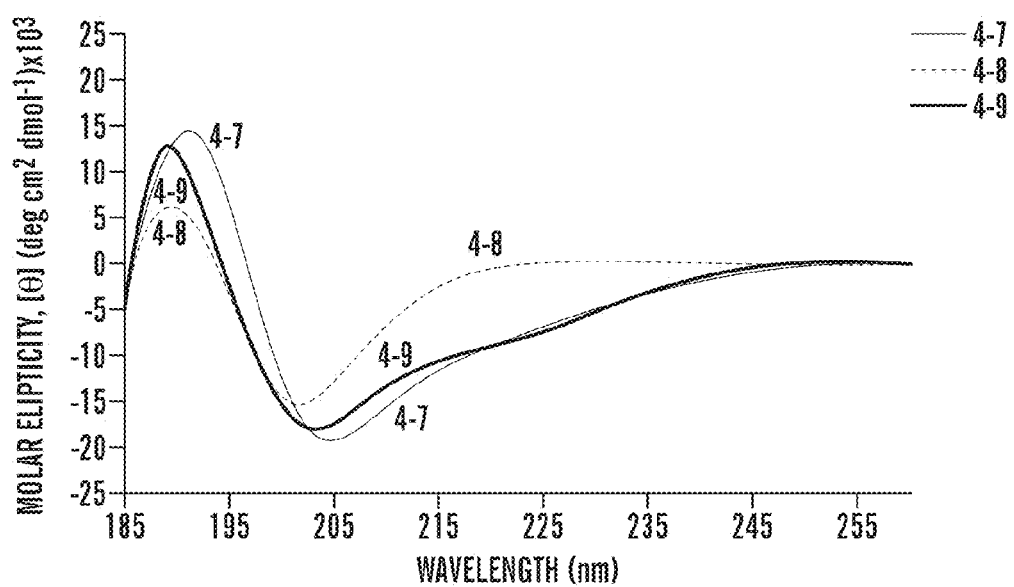
FIG. 22 are the circular dichroism spectra of peptide 4-7, peptide 4-8 (the unconstrained analog of 4-7), and peptide 4-9 (a negative control of peptide 4-7 having alanines in place of F4 and L11) in 10% TFE in PBS.
Figure 23:
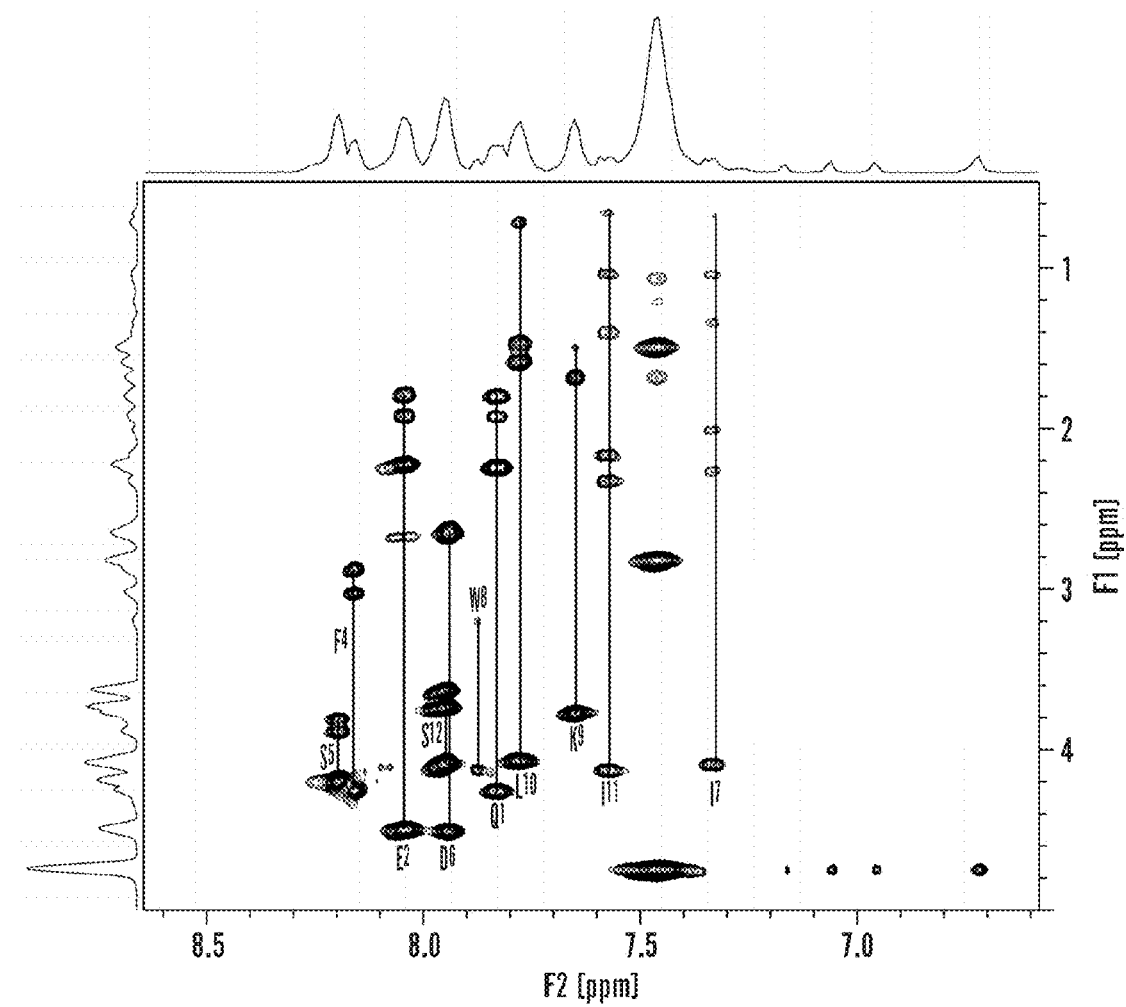
FIG. 23 is the NH—C$\alpha$ region of the 500 MHz TOCSY spectrum (293 K) of peptide 4-7 in 20% TFE-d3 in PBS. $\beta^3$-amino acid residues (7 and 11) are denoted with lower-case blue letters.
Figure 24:
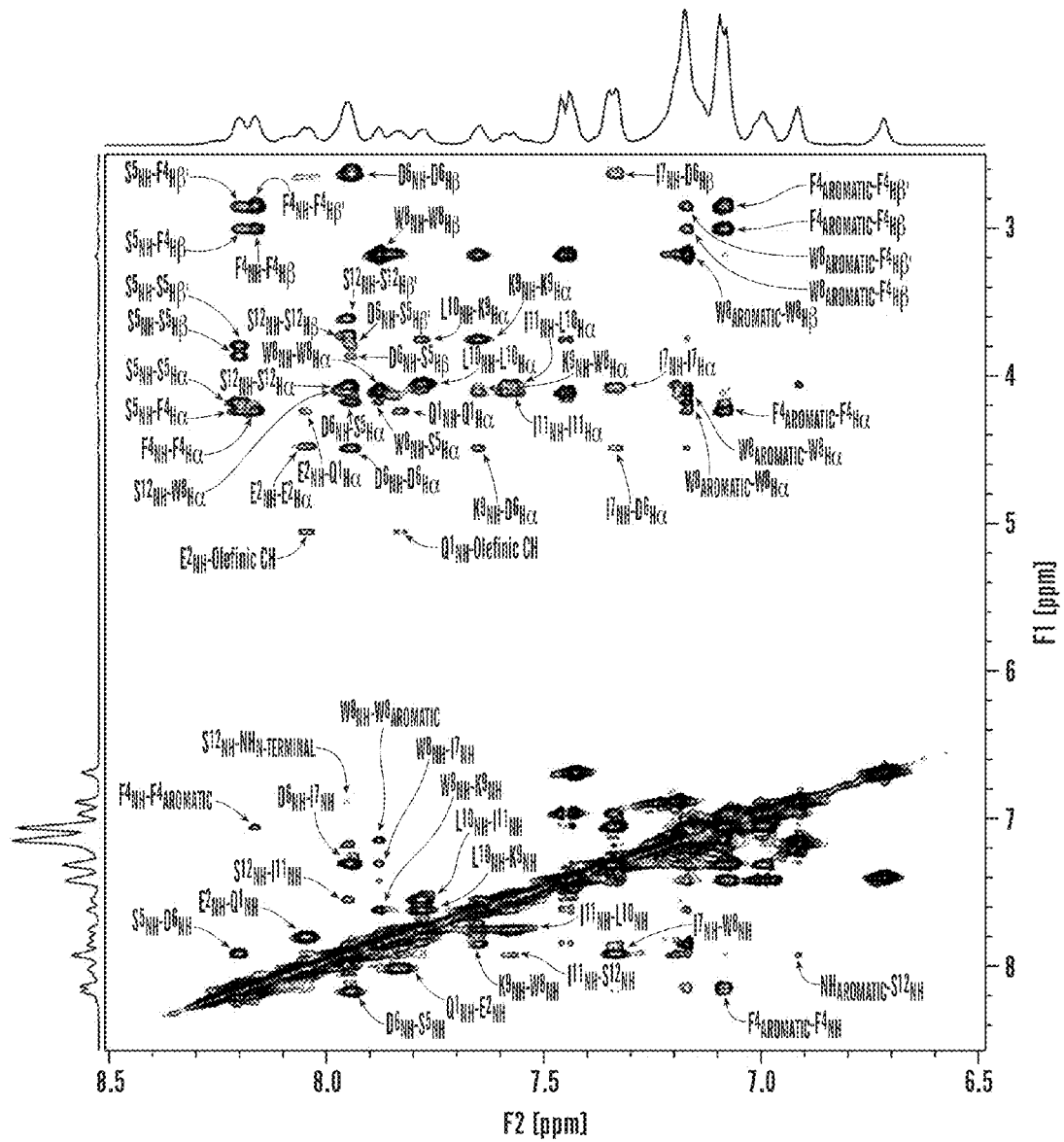
FIG. 24 is a cross-section of the NOESY spectrum (500 MHz, 293 K) of peptide 4-7 in 20% TFE-d3 in PBS. $\beta^3$-Amino acid residues (7 and 11) are shown in lower-case blue letters.
Figure 25:
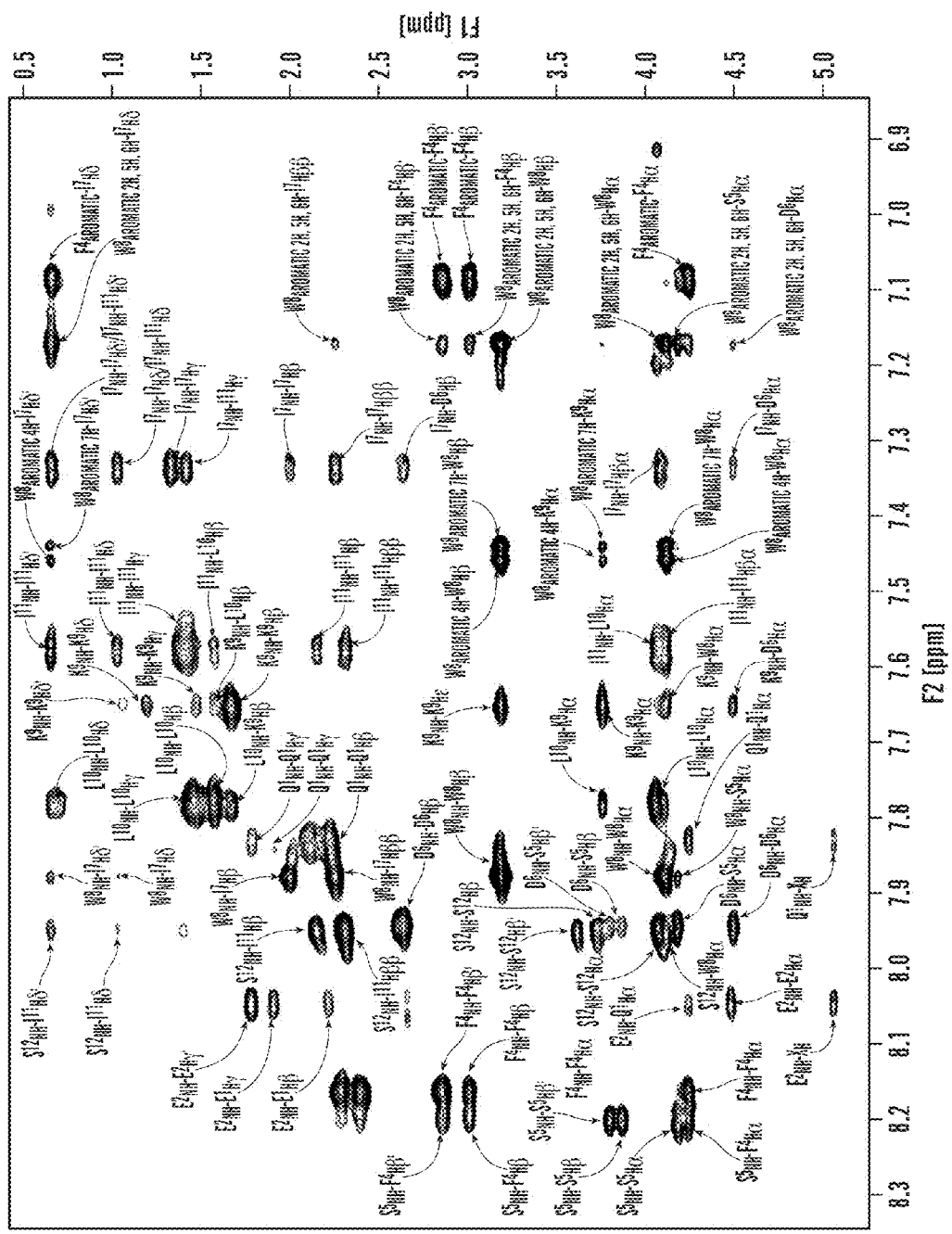
FIG. 25 is a cross-section of the NOESY spectrum (500 MHz, 293 K) of peptide 4-7 in 20% TFE-d3 in PBS. $\beta^3$-Amino acid residues (7 and 11) are shown in lower-case blue letters.
Figure 26:
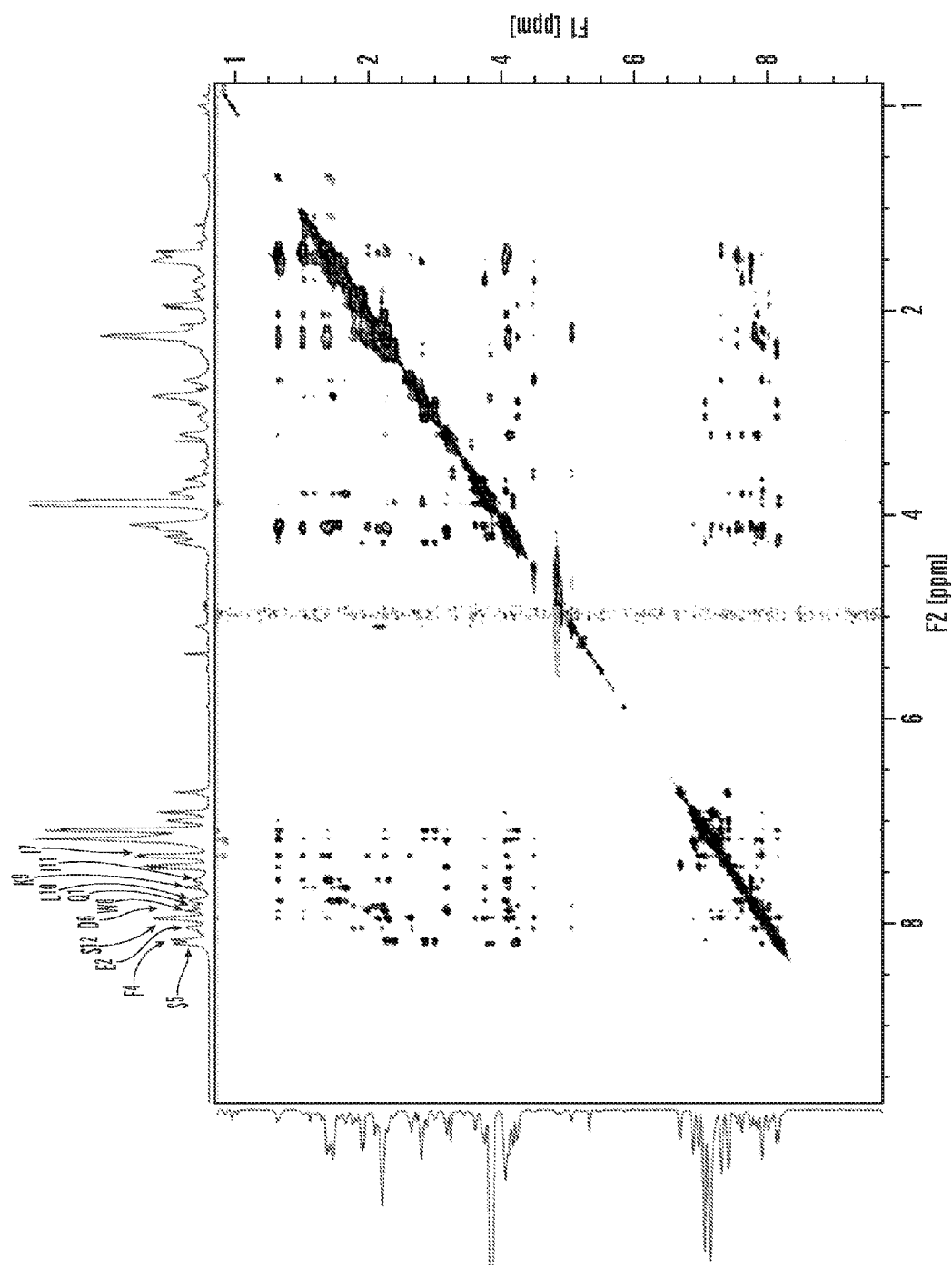
FIG. 26 is the NOESY spectrum (500 MHz, 293 K) of peptide 4-7 in 20% TFE-d3 in PBS. $\beta^3$-Amino acid residues (7 and 11) are shown in lower-case blue letters.

CD spectroscopy was carried out as described in Example 4 supra. FIG. 22 shows the CD spectra of peptide 4-7, peptide 44, and peptide 4-9.

Example 17

2D NMR Spectroscopy

2D NMR spectroscopy was carried out as described in Example 6 supra. The $^1$H NMR assignments and chemical shifts (δ, ppm) for peptide 4-7 (293 K) in 20% TFE-d3 in PBS are shown in Table 7. See FIGS. 23-26.

TABLE 7

$^1$H NMR assignments and chemical shifts for peptide 4-7.

| Residue[a] | NH | Hα | Hβ | Hγ | Hδ | Hε |
|---|---|---|---|---|---|---|
| Q1 | 7.838 | 4.238 | 2.217 | 1.906 | NA | NA |
|  |  |  |  | 1.777 |  |  |
| E2 | 8.048 | 4.477 | 2.209 | 1.899 | NA | NA |
|  |  |  |  | 1.775 |  |  |
| g3 | NA | NA | NA | NA | NA | NA |
| F4 | 8.164 | 4.238 | 2.848 | NA | NA | NA |
|  |  |  | 3.001 |  |  |  |
| S5 | 8.202 | 4.18 | 3.860 | NA | NA | NA |
|  |  |  | 3.792 |  |  |  |
| D6 | 7.946 | 4.173 | 2.632 | NA | NA | NA |
| I7 | 7.331 | 4.076 | 2.247 | 1.991 | 1.319 | 1.02 |
|  | 7.343 |  |  |  |  | 0.648 |
| W8 | 7.88 | 4.176 | 3.179 | NA | NA | NA |
| K9 | 7.649 | 3.751 | 1.66 | 1.465 | 1.182 | 3.179 |
|  |  |  |  |  | 1.046 |  |
| L10 | 7.777 | 4.05 | 1.561 | 1.45 | 0.664 | NA |
| l11 | 7.57 | 4.105 | 2.303 | 2.142 | 1.402 | 1.019 |
|  | 7.588 |  |  |  |  | 0.645 |
| S12 | 7.951 | 4.07 | 3.717 | NA | NA | NA |
|  |  |  | 3.612 |  |  |  |

[a]Lower-case bold letters denote β$^3$-residues.

Example 18

His$_6$-Mdm2 Expression and Purification

His$_6$-Mdm2 expression and purification was carried out as described in Example 8 supra.

Example 19

His$_6$-Mdm2 Binding Studies

The relative affinities of peptides for N-terminal His$_6$-tagged Mdm2 (25-117) were determined using fluorescence polarization-based competitive binding assay with fluorescein labeled p53 peptide (Flu-p53) as described in Example 9 supra. The binding affinity (K$_D$) values reported for each peptide (Table 8) are the averages of 3-5 individual experiments, and were determined by fitting the experimental data to a sigmoidal dose-response nonlinear regression model on GraphPad Prism 4.0 (Roehrl et al., *Biochemistry* 43:16056 (2004), which is hereby incorporated by reference in its entirety).

TABLE 8

Affinity of p53 analogs for Mdm2.

| Peptide | Sequence[a] | Backbone | K$_D$ (μM)[b] |
|---|---|---|---|
| 4-7 | XQEg\*FSDIWKLIS-NH$_2$ (SEQ ID NO: 14) | HBS | 12.6 ± 4.4 |
| 4-8 | Ac-QEgFSDIWKLIS-NH$_2$ (SEQ. ID NO: 15) | Unconstrained | 82.7 ± 58.8 |
| 4-9 | XQEg\*ASDIWKLaS-NH$_2$ (SEQ. ID NO: 16) | HBS | >>1000 |

[a]Lower-case bold letters denote β$^3$-residues; X is pentenoic acid; G* is N-allyl glycine
[b]Binding constant for His$_6$-Mdm2

Results and Discussion of Examples 13-19

Figure 20:
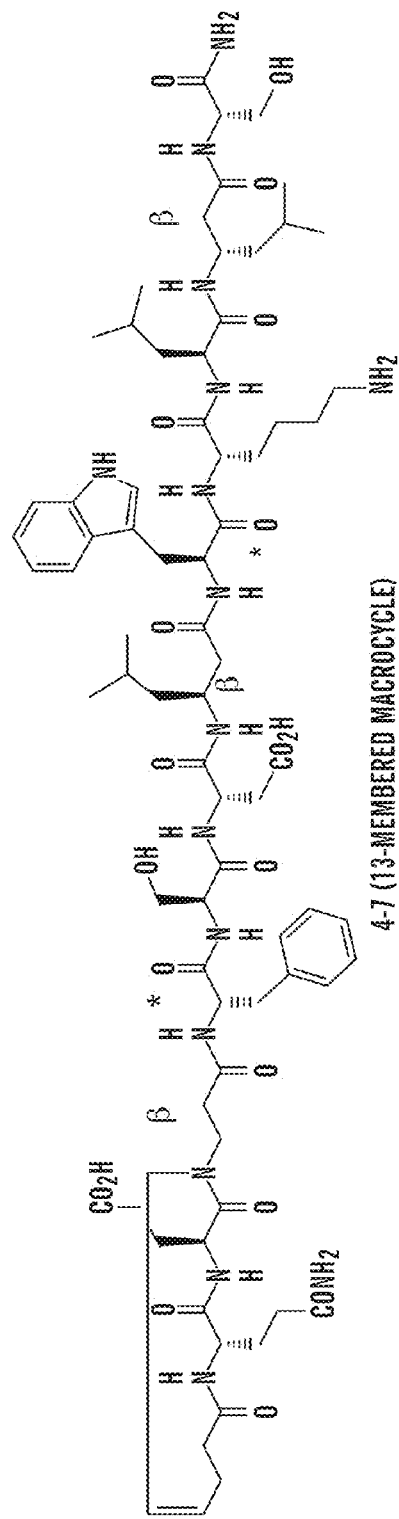
FIG. 20 depicts the sequences of peptide 4-2 (top) and peptide 4-7 (bottom). Important residues for binding are marked with an asterisk. $\beta^3$-homoamino acid residues are marked with "$\beta$".
Figure 27:
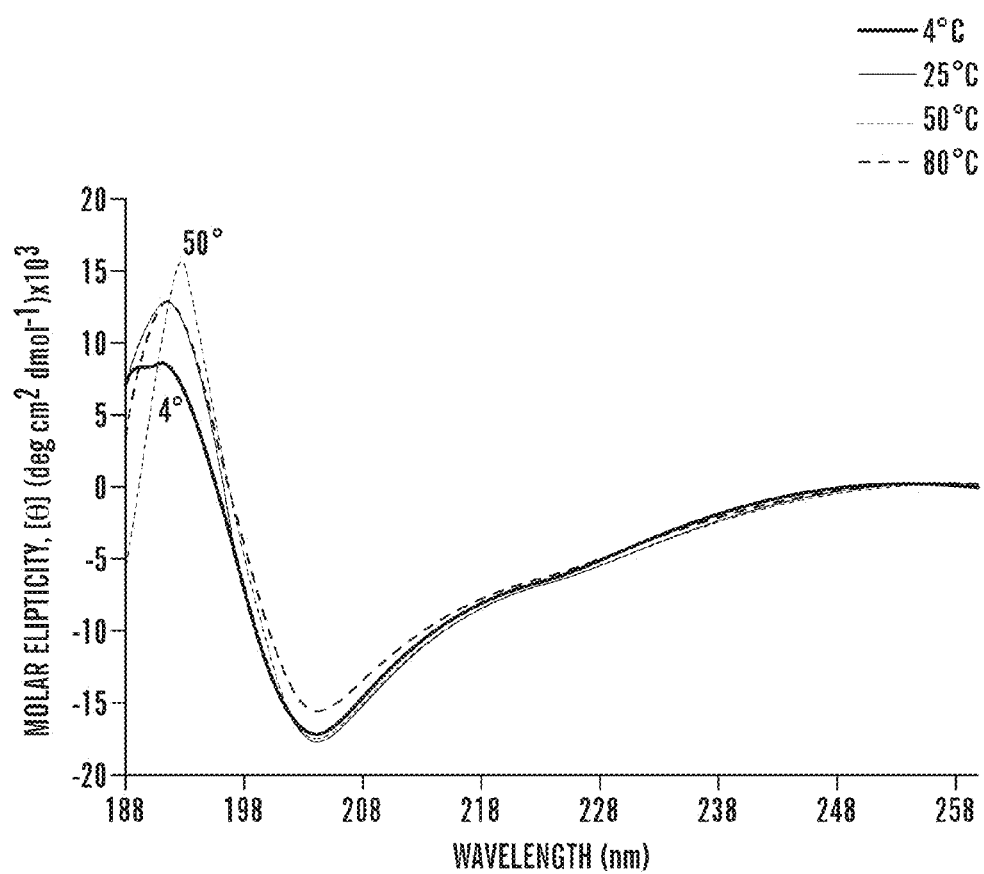
FIG. 27 are the circular dichroism spectra of peptide 4-7 at varying temperatures, showing the effect of temperature on the peptide's stability. The CD spectra were obtained in 10% TFE/PBS.

Whether a 13-membered HBS ring could induce discrete folding in an α3/β-peptide was investigated. Peptide 4-2 is a 13-membered HBS helix composed of α-amino acids (FIG. 20). Peptide 4-7 (FIG. 20), an analog of peptide 4-2 containing an attached α3/β peptide chain, and peptide 4-8, the unconstrained analog of peptide 4-7, were synthesized. The CD spectrum of peptide 4-7 shows a pattern similar to that of peptide 4-1 (a 14-membered HBS macrocycle that has structural features like those of an α-helix), whereas its unconstrained analog, peptide 4-8, shows a random structure (FIG. 22). CD thermal denaturation studies show that peptide 4-7 forms a stable structure in solution (FIG. 27).

Figure 28:
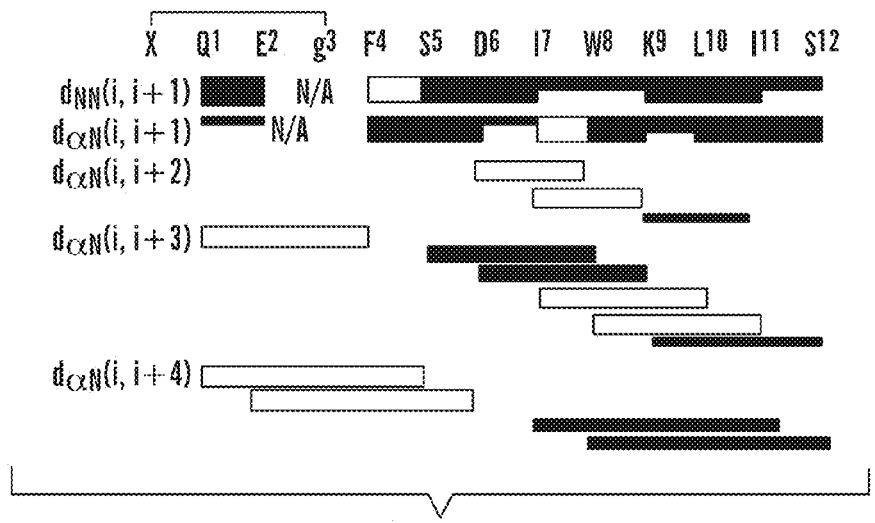
FIG. 28 is the NOESY correlation chart for peptide 4-7. The NMR spectra were obtained in 20% TFE/PBS. $\beta^3$-Amino acid residues (3, 7, and 11) are shown in lower-case blue letters.

2D NOESY and TOCSY experiments were next performed to get further insights into the solution structure of peptide 4-7 (FIGS. 23-26). The assignments and chemical shifts (293 K in 20% TFE-d3 in PBS) are shown in Table 7 supra. The NOESY spectrum shows sequential NH—NH (i and i+1) NOESY cross-peaks, a signature of helical structure, as shown in the NOE correlation chart (FIG. 28). The NOESY spectrum further reveals several medium to weak (i, i+3) and (i, i+4) NH—CHα cross peaks that support an α-helix like conformation in peptide 4-7. These studies suggest that HBS α3/β helices could be nucleated with an appropriately-placed 13-membered macrocycle to give rise to similar structures.

Figure 29:
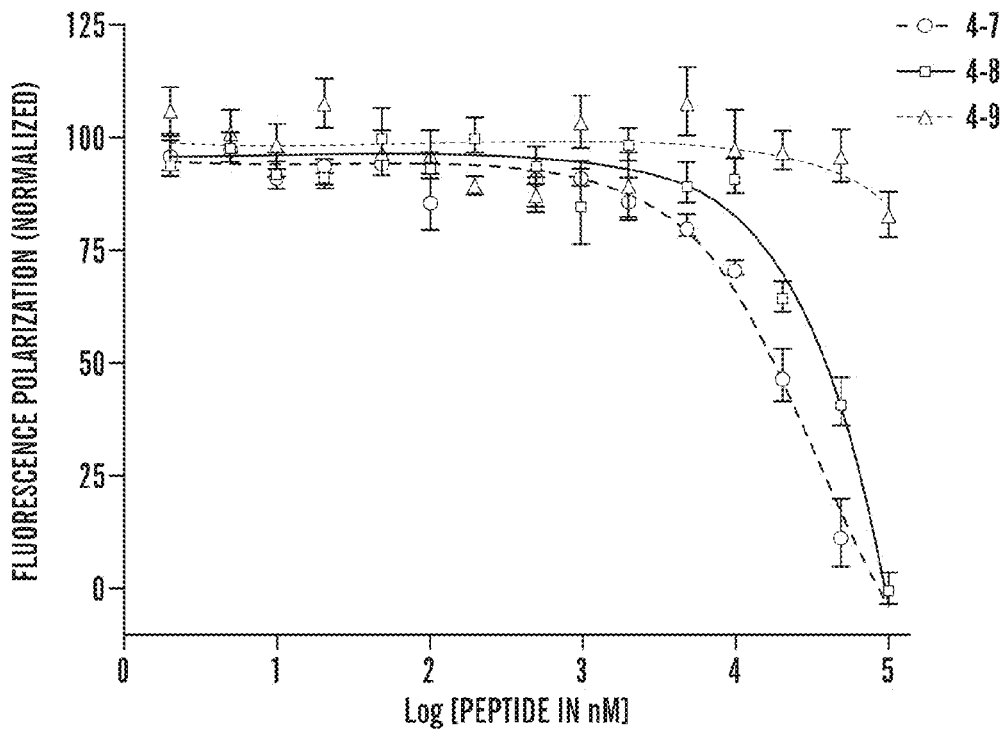
FIG. 29 is a graph showing the determination of binding of peptides 4-7, 4-8, and 4-9 to His$_6$-tagged Mdm2 by a fluorescence-polarization assay.

Whether peptide 4-7 binds to Mdm2 was next investigated, using a fluorescence polarization based binding assay. As shown in FIG. 29, peptide 4-7 was found to bind to Mdm2 (K$_D$=12.6±4.4 μM). The unconstrained peptide 4-8 binds to Mdm2 with K$_D$=82.7±58.8 μM. Peptide 4-9, a negative control of peptide 4-7 in which two of the important amino acid residues (F4 and L11) have been mutated with alanines, does not bind with any appreciable binding affinity (see Table 8 supra). It is expected that the weak binding affinity of peptide 4-7 is due to the mutation of its important residue L11 with a β$^3$-Leu and mutations of G3 and L7, which are located adjacent to important residues F4 and W8, with β$^3$-Gly and β$^3$-Leu (see FIG. 20). Thus, it is predicted that HBS peptides having β-amino acids in place of non-critical amino acid residues would not exhibit a loss in binding affinity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A peptidomimetic having a stable, internally constrained protein secondary structure, wherein the peptidomimetic is a compound of Formula I:

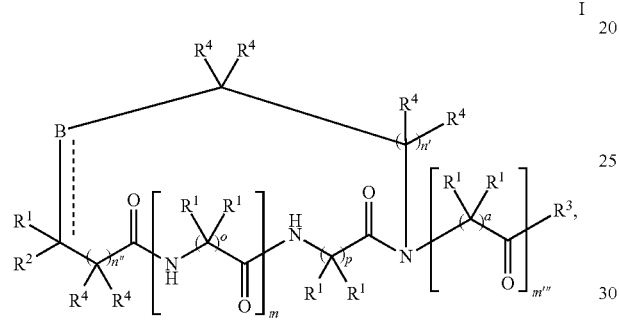

wherein:

B is $C(R^1)(R^{1'})$, O, S, or $NR^1$;

===== is a double bond and each $R^{1'}$ is absent; or ===== is a single bond and each $R^{1'}$ is independently hydrogen, an amino acid side chain, an alkyl, an alkenyl, an alkynyl, a cycloalkyl, a heterocyclyl, an aryl, a heteroaryl, or an arylalkyl;

each $R^1$ is independently hydrogen, an amino acid side chain, an alkyl, an alkenyl, an alkynyl, a cycloalkyl, a heterocyclyl, an aryl, a heteroaryl, or an arylalkyl;

$R^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

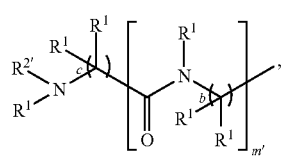

wherein:

$R^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$(CH_2)_{0-1}N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m' is zero or any number;

each b is independently one or two; and c is one or two;

$R^3$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

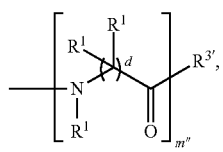

wherein:

$R^{3'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —$OR^5$ wherein $R^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —$N(R^5)_2$ wherein each $R^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;

m" is zero or any number; and each d is independently one or two;

each $R^4$ is independently hydrogen, an alkyl, an alkenyl, an alkynyl, a cycloalkyl, a heterocyclyl, an aryl, a heteroaryl, or an arylalkyl;

m, n', and n" are each independently zero, one, two, three, or four, wherein the sum of m, n', and n" is from two to six;

m'" is zero or one;

a is one or two;

each o is independently one or two;

p is one or two; and wherein at least one of the following conditions is met
(i) m is one, two, three, or four and at least one o is two;
(ii) p is two;
(iii) m''' is one and a is two;
(iv) $R^2$ is a beta amino acid;
(v) $R^2$ is a moiety of Formula A wherein m' is at least one and at least one b is two;
(vi) $R^2$ is a moiety of Formula A wherein c is two;
(vii) $R^2$ is a moiety of Formula A wherein $R^{2'}$ is a beta amino acid;
(viii) $R^3$ is a beta amino acid;
(ix) $R^3$ is a moiety of Formula B wherein m'' is at least one and at least one d is two; and
(x) $R^3$ is a moiety of Formula B wherein $R^{3'}$ is a beta amino acid.

2. The peptidomimetic according to claim 1, wherein B is $C(R^1)(R^{1'})$.

3. The peptidomimetic according to claim 1, wherein B is O.

4. The peptidomimetic according to claim 1, wherein B is S.

5. The peptidomimetic according to claim 1, wherein B is $NR^1$.

6. The peptidomimetic according to claim 1, wherein there are 9 to 12 atoms in the macrocycle portion of the compound.

7. The peptidomimetic according to claim 6, wherein there are 11 atoms in the macrocycle portion of the compound.

8. The peptidomimetic according to claim 1, wherein there are 12 to 15 atoms in the backbone of the macrocycle portion of the compound.

9. The peptidomimetic according to claim 8, wherein there are 14 atoms in the backbone of the macrocycle portion of the compound.

10. The peptidomimetic according to claim 1, wherein there are 15 to 18 atoms in the backbone of the macrocycle portion of the compound.

11. The peptidomimetic according to claim 10, wherein there are 17 atoms in the backbone of the macrocycle portion of the compound.

12. The peptidomimetic according to claim 1, wherein there are 20 to 24 atoms in the backbone of the macrocycle portion of the compound.

13. The peptidomimetic according to claim 12, wherein there are 22 atoms in the backbone of the macrocycle portion of the compound.

14. The peptidomimetic according to claim 1, wherein the peptidomimetic is a compound of Formula IA:

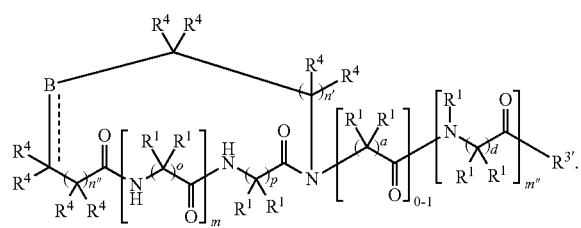

IA wherein:
===== is a double bond and $R^{1'}$ and $R^{4'}$ are both absent; or
===== is a single bond and $R^{1'}$ is hydrogen, an amino acid side chain, an alkyl, an alkenyl, an alkynyl, a cycloalkyl, a heterocyclyl, an aryl, a heteroaryl, or an arylalkyl and $R^{4'}$ is hydrogen, an alkyl, an alkenyl, an alkynyl, a cycloalkyl, a heterocyclyl, an aryl, a heteroaryl, or an arylalkyl.

15. The peptidomimetic according to claim 1, wherein the peptidomimetic is a compound of Formula IB:

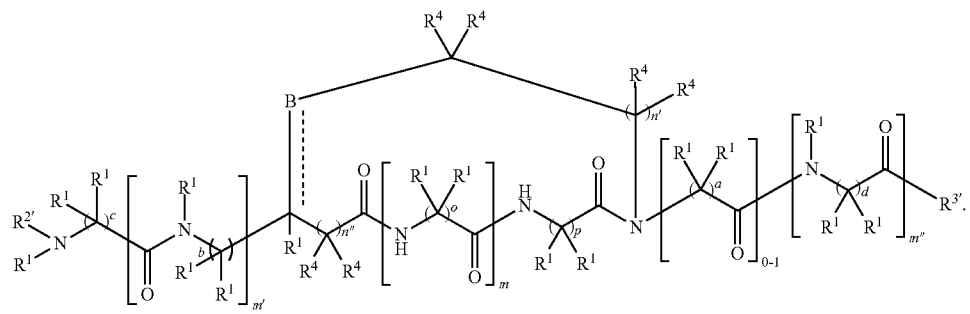

IB

16. The peptidomimetic according to claim 1, wherein the peptidomimetic is a compound of Formula IC:

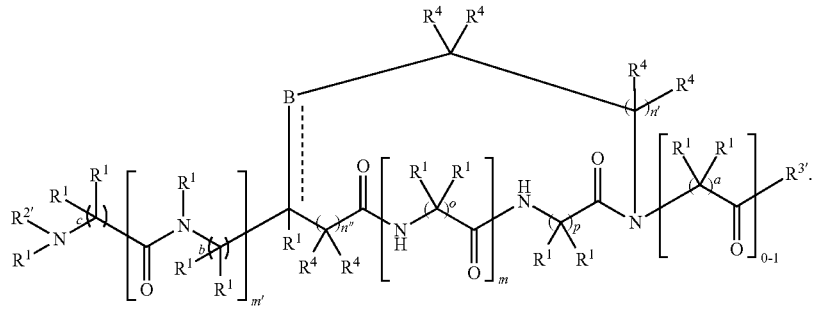

IC

17. A peptidomimetic having a stable, internally constrained protein secondary structure, wherein the peptidomimetic is a compound of Formula IIA:

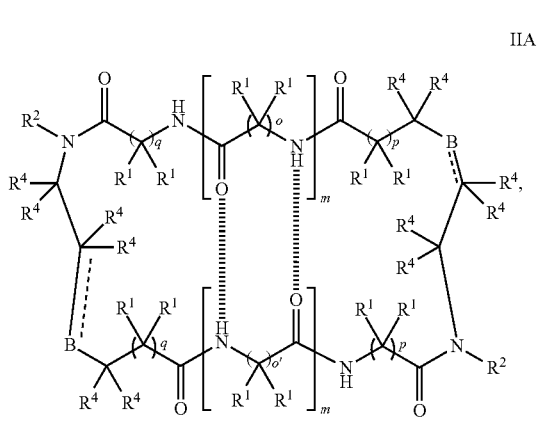

wherein:
each B is independently C(R$^1$)(R$^{1'}$), O, S, or NR$^1$;
each ===== is independently a single or double bond, wherein:
when ===== is a double bond, the R$^{1'}$ and R$^{4'}$ associated therewith are both absent; and
when ===== is a single bond, the R$^{1'}$ associated therewith is hydrogen, an amino acid side chain, an alkyl, an alkenyl, an alkynyl, a cycloalkyl, a heterocyclyl, an aryl, a heteroaryl, or an arylalkyl; and the R$^{4'}$ associated therewith is hydrogen, an alkyl, an alkenyl, an alkynyl, a cycloalkyl, a heterocyclyl, an aryl, a heteroaryl, or an arylalkyl;
each R$^1$ is independently hydrogen, an amino acid side chain, an alkyl, an alkenyl, an alkynyl, a cycloalkyl, a heterocyclyl, an aryl, a heteroaryl, or an arylalkyl;
each R$^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

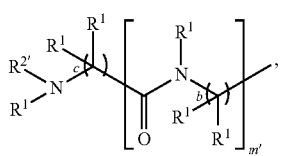

wherein:
R$^{2'}$ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR$^5$ wherein R$^5$ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH$_2$)$_{0-1}$N(R$^5$)$_2$ wherein each R$^5$ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m' is zero or any number;
each b is independently one or two; and
c is one or two;
each R$^4$ is independently hydrogen, an alkyl, an alkenyl, an alkynyl, a cycloalkyl, a heterocyclyl, an aryl, a heteroaryl, or an arylalkyl;
m is one, two, three, or four;
each o and each o' are independently one or two, with the proviso that each corresponding o and o' are the same;
p is one or two;
q is one or two; and
wherein at least one of the following conditions is met
(i) m is one, two, three, or four; at least one o is two; and at least one o' is two;
(ii) p is two;
(iii) q is two;
(iv) at least one R$^2$ is a beta amino acid;
(v) at least one R$^2$ is a moiety of Formula A wherein m' is at least one and at least one b is two;
(vi) at least one R$^2$ is a moiety of Formula A wherein c is two; and
(vii) at least one R$^2$ is a moiety of Formula A wherein R$^{2'}$ is a beta amino acid.

18. The peptidomimetic according to claim 17, wherein B is C(R$^1$)(R$^{1'}$).

19. The peptidomimetic according to claim 17, wherein B is O.

20. The peptidomimetic according to claim 17, wherein B is S.

21. The peptidomimetic according to claim 17, wherein B is NR$^1$.

22. A peptidomimetic having a stable, internally constrained protein secondary structure, wherein the peptidomimetic is a compound of Formula IIB:

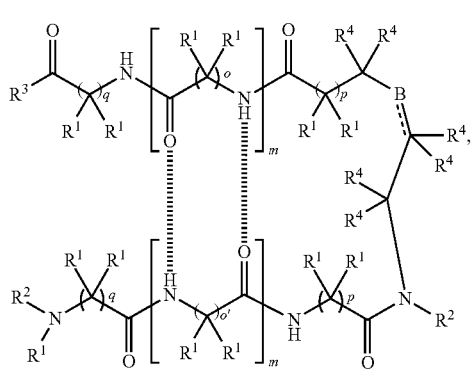

wherein:
B is C(R$^1$)(R$^{1'}$), O, S, or NR$^1$;
===== is a double bond and R$^{1'}$ and R$^{4'}$ are both absent; or
===== is a single bond and R$^{1'}$ is hydrogen, an amino acid side chain, an alkyl, an alkenyl, an alkynyl, a cycloalkyl, a heterocyclyl, an aryl, a heteroaryl, or an arylalkyl and R$^{4'}$ is hydrogen, an alkyl, an alkenyl, an alkynyl, a cycloalkyl, a heterocyclyl, an aryl, a heteroaryl, or an arylalkyl;
each R$^1$ is independently hydrogen, an amino acid side chain, an alkyl, an alkenyl, an alkynyl, a cycloalkyl, a heterocyclyl, an aryl, a heteroaryl, or an arylalkyl;
each R$^2$ is hydrogen; an alkyl; an alkenyl; an alkynyl; a cycloalkyl; a heterocyclyl; an aryl; a heteroaryl; an arylalkyl; an alpha amino acid; a beta amino acid; a peptide;

a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —(CH₂)₀₋₁N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula A:

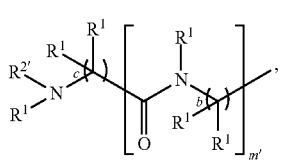

A wherein:
R²' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —(CH₂)₀₋₁N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m' is zero or any number;
each b is independently one or two; and
c is one or two;
R³ is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; —N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag; or a moiety of Formula B:

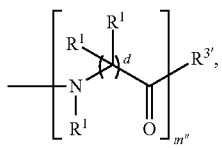

B wherein:
R³' is hydrogen; an alkyl; an alkenyl; an alkynyl; a cycloalkyl; a heterocyclyl; an aryl; a heteroaryl; an arylalkyl; an alpha amino acid; a beta amino acid; a peptide; a targeting moiety; a tag; —OR⁵ wherein R⁵ is hydrogen, an alkyl, an alkenyl, an alkynyl, a cycloalkyl, a heterocyclyl, an aryl, a heteroaryl, an arylalkyl, an acyl, a peptide, a targeting moiety, or a tag; or —N(R⁵)₂ wherein each R⁵ is independently hydrogen, an alkyl, an alkenyl, an alkynyl, a cycloalkyl, a heterocyclyl, an aryl, a heteroaryl, an arylalkyl, an acyl, a peptide, a targeting moiety, or a tag;
m" is zero or any number; and
each d is independently one or two;
each R⁴ is independently hydrogen, an alkyl, an alkenyl, an alkynyl, a cycloalkyl, a heterocyclyl, an aryl, a heteroaryl, or an arylalkyl;
m is one, two, three, or four;
each o and each o' are independently one or two, with the proviso that each corresponding o and o' are the same;
p is one or two;
q is one or two; and
wherein at least one of the following conditions is met
(i) m is one, two, three, or four; at least one o is two; and at least one o' is two;
(ii) p is two;
(iii) q is two;
(iv) at least one R² is a beta amino acid;
(v) at least one R² is a moiety of Formula A wherein m' is at least one and at least one b is two;
(vi) at least one R² is a moiety of Formula A wherein c is two;
(vii) at least one R² is a moiety of Formula A wherein R²' is a beta amino acid;
(viii) R³ is a beta amino acid;
(ix) R³ is a moiety of Formula B wherein m" is at least one and at least one d is two; and
(x) R³ is a moiety of Formula B wherein R³' is a beta amino acid.

23. The peptidomimetic according to claim 22, wherein B is C(R¹)(R¹').

24. The peptidomimetic according to claim 22, wherein B is O.

25. The peptidomimetic according to claim 22, wherein B is S.

26. The peptidomimetic according to claim 22, wherein B is NR¹.

27. A method for promoting cell death, said method comprising:
contacting the cell with one or more compounds according to claim 1 that inhibit p53/hDM2, under conditions effective for the one or more compounds to promote cell death.

* * * * *